United States Patent
Khurana et al.

(10) Patent No.: US 11,547,686 B2
(45) Date of Patent: *Jan. 10, 2023

(54) ACETAMINOPHEN PREGABALIN COMBINATIONS AND METHODS OF TREATING PAIN

(71) Applicant: NEVAKAR INJECTABLES INC., Bridgewater, NJ (US)

(72) Inventors: Varun Khurana, Raritan, NJ (US); Jack Martin Lipman, West Milford, NJ (US); Milan Patel, Edison, NJ (US); Iouri Ilitchev, Hillsborough, NJ (US); Tushar Hingorani, Bridgewater, NJ (US); Kumaresh Soppimath, Plainsboro, NJ (US); Navneet Puri, Lebanon, NJ (US)

(73) Assignee: NEVAKAR INJECTABLES INC., Bridgewater, NJ (US)

( * ) Notice: Subject to any disclaimer, the term of this patent is extended or adjusted under 35 U.S.C. 154(b) by 5 days.

This patent is subject to a terminal disclaimer.

(21) Appl. No.: 16/753,042

(22) PCT Filed: Oct. 2, 2018

(86) PCT No.: PCT/US2018/053864
§ 371 (c)(1),
(2) Date: Apr. 2, 2020

(87) PCT Pub. No.: WO2019/070641
PCT Pub. Date: Apr. 11, 2019

(65) Prior Publication Data
US 2020/0230091 A1    Jul. 23, 2020

Related U.S. Application Data

(60) Provisional application No. 62/567,384, filed on Oct. 3, 2017.

(51) Int. Cl.
| | | |
|---|---|---|
| *A61K 31/197* | (2006.01) | |
| *A61P 29/00* | (2006.01) | |
| *A61K 31/167* | (2006.01) | |
| *A61K 31/19* | (2006.01) | |
| *A61K 31/194* | (2006.01) | |
| *A61K 33/42* | (2006.01) | |

(52) U.S. Cl.
CPC .......... *A61K 31/197* (2013.01); *A61K 31/167* (2013.01); *A61K 31/19* (2013.01); *A61K 31/194* (2013.01); *A61K 33/42* (2013.01); *A61P 29/00* (2018.01)

(58) Field of Classification Search
CPC .... A61K 31/197; A61K 31/167; A61K 31/19; A61K 31/194; A61K 33/42; A61P 29/00
See application file for complete search history.

(56) References Cited

U.S. PATENT DOCUMENTS

| | | |
|---|---|---|
| 6,426,368 B2 | 7/2002 | Bueno et al. |
| 6,451,857 B1 | 9/2002 | Hurtt et al. |
| 10,052,296 B2 | 8/2018 | Khurana et al. |
| 2005/0004219 A1 | 1/2005 | Hildebrand et al. |
| 2006/0281816 A1 | 12/2006 | Hedvati et al. |
| 2008/0050352 A1 | 2/2008 | Webb et al. |
| 2010/0279984 A1* | 11/2010 | Bonke ............... A61P 29/00 514/86 |
| 2012/0245230 A1 | 9/2012 | Velez Ferreira et al. |
| 2017/0182162 A1 | 6/2017 | Rinaldi et al. |

FOREIGN PATENT DOCUMENTS

| | | | |
|---|---|---|---|
| EP | 2151237 A1 | 2/2010 | |
| WO | WO-9908670 A1 | 2/1999 | |
| WO | WO-2005044252 A1 | 5/2005 | |
| WO | WO-2015144825 A1 * | 10/2015 | ........... A61K 47/183 |
| WO | WO-2017134540 A1 | 8/2017 | |

OTHER PUBLICATIONS

Durmus et al. The post-operative analgesic effects of a combination of gabapentin and paracetamol in patients undergoing abdominal hysterectomy: a randomized clinical trial. Acta Anaesthesiol Scand. 2007;51:299-304.
http://compoundingtoday.com/Tunicity/Adjust/ available online Jul. 2007 and accompanying internet active page (Year 2007).
https://reference.medscape.com/drug/tylenol-acetaminophen-343346; available online Apr. 2011, and accompanying internet page (Year 2011).
https://www.accessdata.fda.gov/drugsatfda.docs/label/2011/021446s026,022488s005lbl.pdf, available online Oct. 2012 and accompanying internet active page (Year 2012).
International Search Report dated Feb. 7, 2019 for International Application Serial No. PCT/US2018/053864, 3 pages.
Kusunose et al., Molecular Bassis for the Dosing Time-Dependency of Anti-Allodynic Effects ofGabapentin in a Mouse Model of Neuropathic Pain. Molecular Pain, Biomed Central, 6.1 (Nov. 26, 2010): 1-8.
Hama Aldric T. et al: "Cannabinoid receptor-mediated antinociception with acetaminophen drug combinations in rats with neuropathic spinal cord injury pain", Neuropharmacology, vol. 58, No. 4-5, Mar. 1, 2010.
Mathiesen.et al: "Pregabalin and dexamethasone in combination with paracetamol for postoperative pain control after abdominal hysterectomy. A randomized clinical trial : Multimodal pain treatment for abdominal hysterectomy", Acta Anaesthesiologica Scandinavica., Dec. 8, 2008.
Mititelu Tartau Liliana et al: "Synergic Effects of Pregabalin-Acetaminophen Combination in Somatic and Visceral Nociceptive Reactivity", Pharmacology, vol. 93,No. 5-6, Sep. 9, 2014.
Supplementary European Search Report of European Patent Application No. EP18864043.7 dated Jun. 4, 2021.

* cited by examiner

*Primary Examiner* — Snigdha Maewall
(74) *Attorney, Agent, or Firm* — Umberg Zipser LLP

(57) ABSTRACT

Compositions and methods for an injectable liquid formulation for reducing consumption or need of a postoperative analgesic compound by a patient are presented. The pharmaceutical formulation can contain a non-opioid analgesic and a gabapentinoid, and can be administered prior to surgery to reduce postoperative pain.

36 Claims, 5 Drawing Sheets

ACETAMINOPHEN PREGABALIN COMBINATIONS AND METHODS OF TREATING PAIN

CROSS REFERENCE

This application claims the benefit of U.S. Provisional Application No. 62/567,384, filed Oct. 3, 2017, which is incorporated herein by reference in its entirety.

BACKGROUND

Postoperative pain management can involve the use of opioids or non-steroidal inflammatory drugs (NSAIDs) following surgery. However, the use of opioids or opioid-derived analgesics can lead to undesirable side effects including, for example, nausea, vomiting, constipation, and poor respiratory function. Thus, an analgesic that could be administered to a patient prior to surgery could obviate the need for postoperative administration of opioids and reduce the occurrence of unwanted side effects.

INCORPORATION BY REFERENCE

Each patent, publication, and non-patent literature cited in the application is hereby incorporated by reference in its entirety as if each was incorporated by reference individually.

SUMMARY

In some embodiments, the invention provides a pharmaceutical composition comprising, in a liquid unit dosage form: a) a gabapentinoid; b) acetaminophen; c) a pH-adjusting agent; and d) water.

In some embodiments, the invention provides a method of treating pain in a subject in need thereof, the method comprising administering to the subject a therapeutically-effective amount of a liquid unit dosage form, wherein the liquid unit dosage form comprises: a) a gabapentinoid; b) acetaminophen; c) a pH-adjusting agent; and d) water.

In some embodiments, the invention provides a method of manufacturing a pharmaceutical formulation, the method comprising: a) adding water to a manufacturing tank; b) deoxygenating the water in the manufacturing tank by sparging nitrogen to achieve a dissolved oxygen level of less than about 1 ppm; c) adding a buffer to the water in the manufacturing tank to provide a mixture; d) adding a pH-adjusting agent to the mixture in the manufacturing tank, wherein the adding the pH-adjusting agent to the mixture in the manufacturing tank adjusts a pH of the mixture to about pH 4 to about pH 7; e) disposing a gabapentinoid into the mixture in the manufacturing tank; and f) disposing acetaminophen into the mixture in the manufacturing tank.

DETAILED DESCRIPTION

Figure 1:
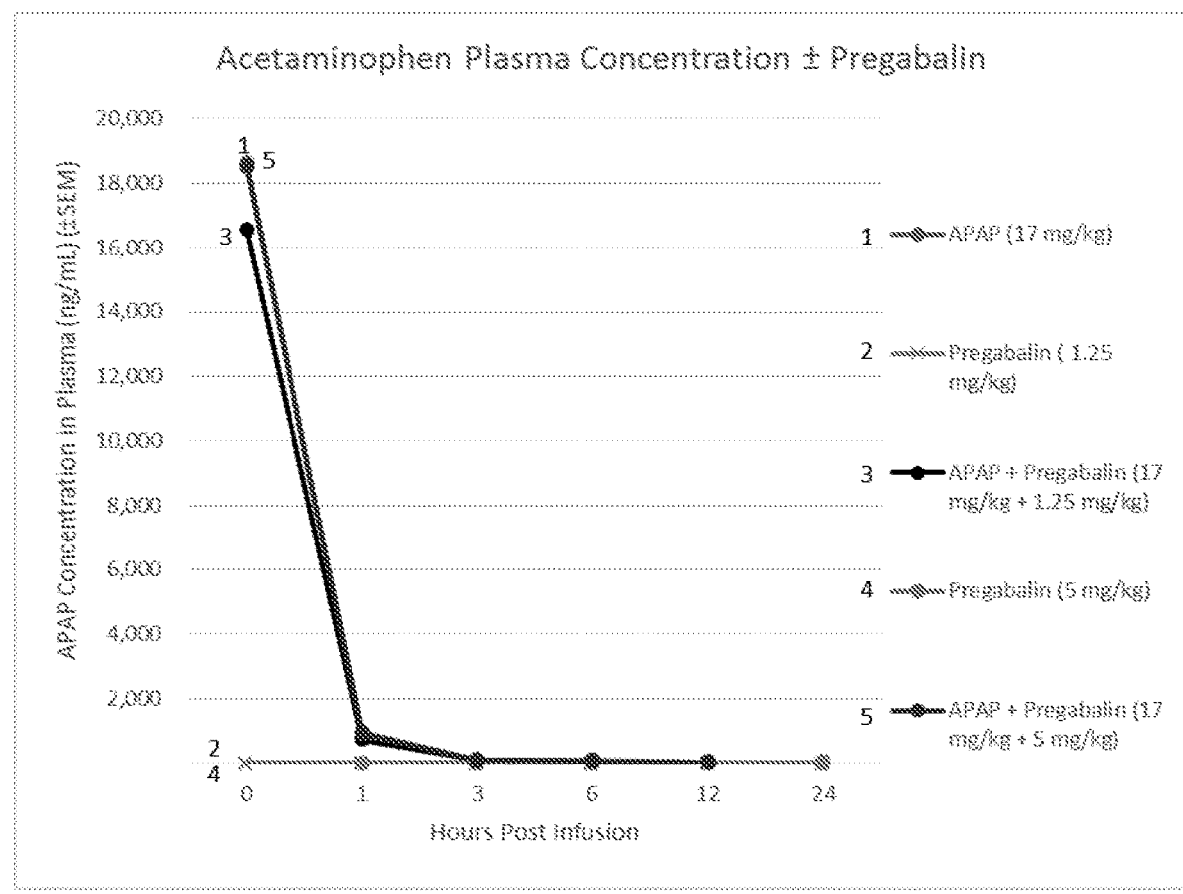
FIG. 1 shows a graph of plasma concentration of acetaminophen either administered alone or in combination with pregabalin after intravenous administration.

The present application relates to pharmaceutical formulations that can be used to relieve postoperative pain in a subject in need thereof. After surgery, patients can suffer from severe pain that can persist for days, weeks, or months. Postoperative pain can be managed by administering to the patient, for example, centrally-acting µ-opioid analgesics or NSAIDs. However, the occurrence of undesirable side effects can lead to reduced patient compliance and ineffective pain treatment. The present application describes a pharmaceutical formulation and methods of use thereof to alleviate postoperative pain by, for example, preoperatively administering the pharmaceutical formulation to the patient. A pharmaceutical formulation described herein can also reduce postoperative opioid consumption by a patient who has been administered the pharmaceutical formulation.

Pain.

The present disclosure provides pharmaceutical compositions for the treatment of pain. Pain can be, for example, mild, moderate, severe, or agonizing. The pain of a subject can be assessed using a numeric scale, in which a patient can self-report pain on a scale from 0-10, where 0 indicates no pain, 1-3 suggests mild pain, 4-6 indicates moderate pain, and 7-10 suggests severe and disabling pain.

Pain can include, for example, angina pain, bone injury pain, central pain, chronic lower back pain, cluster headaches, dental pain, genitourinary tract-related pain including cystitis and nociceptive pain, herpes neuralgia, migraine, neuropathic pain, pain during labor and delivery, pain resulting from burns, phantom limb pain, postoperative pain, postpartum pain, surgical pain, or visceral pain. In some embodiments, the pain is postoperative pain.

The pain can be chronic or acute. Postoperative pain can describe that occurs after a surgery, and can be a direct or indirect result of the surgery.

A pharmaceutical formulation described herein can be administered to the patient during or prior to surgery to treat, for example, acute postoperative pain. The postoperative pain can be reduced by at least about 10%, at least about 15%, at least about 20%, at least about 25%, at least about 30%, at least about 35%, at least about 40%, at least about 45%, at least about 50%, at least about 60%, at least about 70%, at least about 80%, at least about 90%, or at least about 99%. The reduction is postoperative pain can happen after about 10 minutes, about 20 minutes, about 30 minutes, about 40 minutes, about 50 minutes, about 1 hour, about 2 hours, about 3 hours, about 4 hours, about 5 hours, about 6 hours, about 8 hours, about 10 hours, or about 12 hours after the surgery.

Non-Opioid Analgesic.

The present disclosure provides pharmaceutical formulations containing, for example, a non-opioid analgesic. A non-opioid analgesic can include, for example, an NSAID, an anti-depressant, a gabapentinoid, an anti-convulsant, an anti-pyretic, acetylsalicylic acid, or acetaminophen (N-(4-hydroxyphenyl)acetamide); paracetamol; N-acetyl-para-aminophenol). Acetaminophen is an anti-pyretic agent, and can be used to treat mild to moderate pain in adults and children.

In some embodiments, a non-opioid analgesic in a pharmaceutical formulation described herein is acetaminophen. In some embodiments, a non-opioid analgesic in a pharmaceutical formulation described herein is a gabapentinoid. In some embodiments, a pharmaceutical formulation described herein contains acetaminophen and a gabapentinoid.

The non-opioid analgesic can be, for example, aceclofenac, acemetacin, acetaminophen, acetylsalicylic acid, amoxiprin, azapropazone, benorilate, bromfenac, carprofen, choline magnesium salicylate, diflunisal, diclofenac, etodolac, faislamine, fenbuprofen, flubiprofen, gabapentin, ibuprofen, indometacin, ketaprofen, ketorolac, lomoxicam, loxoprofen, magnesium salicylate, meclofenamic, mefenamic acid, meloxicam, metamizole, methyl salicylate, nabumetone, naproxen, oxyphenbutazone, piroxicam, phenylbutazone, pregabalin, sulfinprazone, sulindac, suprofen, tenoxicam, tolmetin, or a pharmaceutically acceptable salt of any of the foregoing, or any combination thereof.

Gabapentinoids.

Gabapentinoids are a class of compounds that are derivatives of γ-aminobutyric acid (GABA). Gabapentinoids can block the $\alpha_2\delta$ subunit (gabapentin receptor)-containing voltage-dependent calcium channels (VDCC). Upon binding of the gabapentinoid to the $\alpha_2\delta$ subunit-containing VDCCs, the gabapentinoid can inhibit the action of the VDCC. Gabapentinoids demonstrate similar affinity to the two subunits ($\alpha_2\delta$-1 and $\alpha_2\delta$-2) of the $\alpha_2\delta$ portion of the VDCC. A gabapentinoid can include, for example, gabapentin and pregabalin (3-isobutyl-γ-aminobutyric acid).

Pregabalin is (3S)-3-(Aminomethyl)-5-methylhexanoic acid, and is a γ-aminobutyric acid analogue, with anticonvulsant, anxiolytic, and sleep-modulating properties. Pregabalin can treat, for example, acute pain, chronic pain, neuropathic pain, incisional injury, and inflammatory injury. Additionally, pregabalin can be used to reduce acute postoperative pain when the pregabalin is administered to the patient preoperatively.

A pharmaceutical formulation described herein can contain, for example, pregabalin. The pharmaceutical formulation can further contain, for example, acetaminophen.

Pharmaceutically Acceptable Salts.

The present disclosure provides the use of pharmaceutically-acceptable salts of any compound described herein. Pharmaceutically-acceptable salts include, for example, acid-addition salts and base-addition salts. The acid that is added to the compound to form an acid-addition salt can be an organic acid or an inorganic acid. A base that is added to the compound to form a base-addition salt can be an organic base or an inorganic base. In some embodiments, a pharmaceutically-acceptable salt is a metal salt.

Metal salts can arise from the addition of an inorganic base to a compound described herein. The inorganic base consists of a metal cation paired with a basic counterion, such as, for example, hydroxide, carbonate, bicarbonate, or phosphate. The metal can be an alkali metal, alkaline earth metal, transition metal, or main group metal. In some embodiments, the metal is lithium, sodium, potassium, cesium, cerium, magnesium, manganese, iron, calcium, strontium, cobalt, titanium, aluminum, copper, cadmium, or zinc.

In some embodiments, a metal salt is a lithium salt, a sodium salt, a potassium salt, a cesium salt, a cerium salt, a magnesium salt, a manganese salt, an iron salt, a calcium salt, a strontium salt, a cobalt salt, a titanium salt, an aluminum salt, a copper salt, a cadmium salt, or a zinc salt.

Ammonium salts can arise from the addition of ammonia or an organic amine to a compound described herein. In some embodiments, the organic amine is triethyl amine, diisopropyl amine, ethanol amine, diethanol amine, triethanol amine, morpholine, N-methylmorpholine, piperidine, N-methylpiperidine, N-ethylpiperidine, dibenzylamine, piperazine, pyridine, pyrrazole, piprazole, imidazole, or pyrazine.

In some embodiments, an ammonium salt is a triethyl amine salt, a diisopropyl amine salt, an ethanol amine salt, a diethanol amine salt, a triethanol amine salt, a morpholine salt, an N-methylmorpholine salt, a piperidine salt, an N-methylpiperidine salt, an N-ethylpiperidine salt, a dibenzylamine salt, a piperazine salt, a pyridine salt, a pyrrazole salt, a piprazole salt, an imidazole salt, or a pyrazine salt.

Acid addition salts can arise from the addition of an acid to a compound described herein. In some embodiments, the acid is organic. In some embodiments, the acid is inorganic. In some embodiments, the acid is hydrochloric acid, hydrobromic acid, hydroiodic acid, nitric acid, nitrous acid, sulfuric acid, sulfurous acid, a phosphoric acid, isonicotinic acid, lactic acid, salicylic acid, tartaric acid, ascorbic acid, gentisinic acid, gluconic acid, glucaronic acid, saccaric acid, formic acid, benzoic acid, glutamic acid, pantothenic acid, acetic acid, propionic acid, butyric acid, fumaric acid, succinic acid, methanesulfonic acid, ethanesulfonic acid, benzenesulfonic acid, p-toluenesulfonic acid, citric acid, oxalic acid, or maleic acid.

In some embodiments, the salt is a hydrochloride salt, a hydrobromide salt, a hydroiodide salt, a nitrate salt, a nitrite salt, a sulfate salt, a sulfite salt, a phosphate salt, isonicotinate salt, a lactate salt, a salicylate salt, a tartrate salt, an ascorbate salt, a gentisinate salt, a gluconate salt, a glucaronate salt, a saccarate salt, a formate salt, a benzoate salt, a glutamate salt, a pantothenate salt, an acetate salt, a propionate salt, a butyrate salt, a fumarate salt, a succinate salt, a methanesulfonate salt, an ethanesulfonate salt, a benzenesulfonate salt, a p-toluenesulfonate salt, a citrate salt, an oxalate salt, or a maleate salt.

Formulations.

A pharmaceutical formulation of the disclosure can provide a therapeutically-effective amount of any compound disclosed herein. A pharmaceutical formulation of the disclosure can provide a therapeutically-effective amount of a gabapentinoid and an additional non-opioid analgesic. In some embodiments, the gabapentinoid is pregabalin. In some embodiments, the additional non-opioid analgesic is acetaminophen.

The disclosed formulations can contain one or more pharmaceutically-acceptable agents, which alone or in combination solubilize a compound herein or a pharmaceutically-acceptable salt thereof. In some embodiments, the pharmaceutically-acceptable agent is a buffer. In some embodiments, the pharmaceutically-acceptable agent is a citrate buffer. In some embodiments, the pharmaceutically-acceptable agent is a phosphate buffer. In some embodiments, the pharmaceutically-acceptable agent is an acetate buffer. A buffer as described herein can be formed from a solution containing, for example, an acid and a conjugate base of the acid, or a base and a conjugate acid of the base. The acid in a buffer described herein can be a weak acid. A base in a buffer described herein can be a weak base. Any formulation described herein can contain, for example, an acid, and a conjugate base of the acid, or a base, and a conjugate acid of the base.

A formulation described herein can contain an isotonicity inducing agent. The isotonicity inducing agent can be, for example, sodium chloride or mannitol.

In some embodiments, a compound disclosed herein or pharmaceutically-acceptable salt thereof is present in a formulation in an amount of from about 0.1 mg/mL to about 100 mg/mL, from about 0.1 mg/mL to about 1 mg/mL, from about 0.1 mg/mL to about 5 mg/mL, from about 5 mg/mL to about 10 mg/mL, from about 10 mg/mL to about 15 mg/mL, from about 15 mg/mL to about 20 mg/mL, from about 20 mg/mL to about 25 mg/mL, from about 25 mg/mL to about 30 mg/mL, from about 30 mg/mL to about 35 mg/mL, from about 35 mg/mL to about 40 mg/mL, from about 40 mg/mL to about 45 mg/mL, about 45 mg/mL to about 50 mg/mL, from about 50 mg/mL to about 55 mg/mL, from about 55 mg/mL to about 60 mg/mL, from about 60 mg/mL to about 65 mg/mL, from about 65 mg/mL to about 70 mg/mL, from about 70 mg/mL to about 75 mg/mL, about 75 mg/mL to about 80 mg/mL, from about 80 mg/mL to about 85 mg/mL, from about 85 mg/mL to about 90 mg/mL, from about 90 mg/mL to about 95 mg/mL, or from about 95 mg/mL to about 100 mg/mL. The compound can be, for example, acetaminophen or pregabalin.

In some embodiments, a compound disclosed herein or pharmaceutically-acceptable salt thereof is present in a formulation in an amount of about 1 mg/mL, about 2 mg/mL, about 3 mg/mL, about 4 mg/mL, about 5 mg/mL, about 6 mg/mL, about 7 mg/mL, about 8 mg/mL, about 9 mg/mL, about 10 mg/mL, about 11 mg/mL about 12 mg/mL, about 13 mg/mL, about 14 mg/mL, about 15 mg/mL, about 16 mg/mL, about 17 mg/mL, about 18 mg/mL, about 19 mg/mL, about 20 mg/mL, about 21 mg/mL about 22 mg/mL, about 23 mg/mL, about 24 mg/mL, about 25 mg/mL, about 26 mg/mL, about 27 mg/mL, about 28 mg/mL, about 29 mg/mL, about 30 mg/mL, about 31 mg/mL about 32 mg/mL, about 33 mg/mL, about 34 mg/mL, about 35 mg/mL, about 36 mg/mL, about 37 mg/mL, about 38 mg/mL, about 39 mg/mL, about 40 mg/mL, about 41 mg/mL about 42 mg/mL, about 43 mg/mL, about 44 mg/mL, about 45 mg/mL, about 46 mg/mL, about 47 mg/mL, about 48 mg/mL, about 49 mg/mL, about 50 mg/mL, about 51 mg/mL about 52 mg/mL, about 53 mg/mL, about 54 mg/mL, about 55 mg/mL, about 56 mg/mL, about 57 mg/mL, about 58 mg/mL, about 59 mg/mL, about 60 mg/mL, about 61 mg/mL about 62 mg/mL, about 63 mg/mL, about 64 mg/mL, about 65 mg/mL, about 66 mg/mL, about 67 mg/mL, about 68 mg/mL, about 69 mg/mL, about 70 mg/mL, about 71 mg/mL about 72 mg/mL, about 73 mg/mL, about 74 mg/mL, about 75 mg/mL, about 76 mg/mL, about 77 mg/mL, about 78 mg/mL, about 79 mg/mL, about 80 mg/mL, about 81 mg/mL about 82 mg/mL, about 83 mg/mL, about 84 mg/mL, about 85 mg/mL, about 86 mg/mL, about 87 mg/mL, about 88 mg/mL, about 89 mg/mL, about 90 mg/mL, about 91 mg/mL about 92 mg/mL, about 93 mg/mL, about 94 mg/mL, about 95 mg/mL, about 96 mg/mL, about 97 mg/mL, about 98 mg/mL, about 99 mg/mL, or about 100 mg/mL. The compound can be, for example, acetaminophen or pregabalin.

A pharmaceutical formulation described herein can contain, for example, acetaminophen, pregabalin, sodium chloride, and citric acid monohydrate. The pharmaceutical formulation can be at, for example, pH 5, 5.5, or 6. In some embodiments, the pH of the pharmaceutical formulation is 5.5. In some embodiments, the pH of the pharmaceutical formulation is 6. The acetaminophen can be present in the pharmaceutical formulation at a concentration of about 5 mg/mL, about 6 mg/mL, about 7 mg/mL, about 8 mg/mL, about 9 mg/mL, or about 10 mg/mL. In some embodiments, the acetaminophen is present in the pharmaceutical formulation at a concentration of 10 mg/mL. The pregabalin can be present in the pharmaceutical formulation a concentration of about 4 mg/mL, about 4.5 mg/ml, or about 5 mg/mL. In some embodiments, the pregabalin is present in the pharmaceutical formulation at a concentration of 4.5 mg/mL. The sodium chloride can be present in the pharmaceutical formulation at a concentration of about 4 mg/mL, about 4.5 mg/mL, about 5 mg/mL, about 5.5 mg/mL, or about 6 mg/mL. In some embodiments, the sodium chloride is present in the pharmaceutical formulation at a concentration of 5 mg/mL. In some embodiments, the sodium chloride is present in the pharmaceutical formulation at a concentration of 4.5 mg/mL. The citric acid monohydrate can be present in the pharmaceutical formulation at a concentration of about 2 mg/mL, about 2.05 mg/mL, about 2.1 mg/mL, about 2.101 mg/mL, about 2.102 mg/mL, about 2.103 mg/mL, about 2.014 mg/mL, about 2.105 mg/mL, about 2.11 mg/mL, about 2.15 mg/mL, or about 2.2 mg/mL. In some embodiments, the citric acid monohydrate is present in the pharmaceutical formulation at a concentration of 2.101 mg/mL.

A pharmaceutical formulation described herein can contain, for example, acetaminophen, pregabalin, sodium chloride, and acetic acid. The pharmaceutical formulation can be at, for example, pH 5, 5.5, or 6. In some embodiments, the pH of the pharmaceutical formulation is 5.5. The acetaminophen can be present in the pharmaceutical formulation at a concentration of about 5 mg/mL, about 6 mg/mL, about 7 mg/mL, about 8 mg/mL, about 9 mg/mL, or about 10 mg/mL. In some embodiments, the acetaminophen is present in the pharmaceutical formulation at a concentration of 10 mg/mL. The pregabalin can be present in the pharmaceutical formulation a concentration of about 4 mg/mL, about 4.5 mg/ml, or about 5 mg/mL. In some embodiments, the pregabalin is present in the pharmaceutical formulation at a concentration of 4.5 mg/mL. The sodium chloride can be present in the pharmaceutical formulation at a concentration of about 4 mg/mL, about 4.5 mg/mL, about 5 mg/mL, about 5.5 mg/mL, or about 6 mg/mL. In some embodiments, the sodium chloride is present in the pharmaceutical formulation at a concentration of 5 mg/mL. The acetic acid can be present in the pharmaceutical formulation at a concentration of about 0.5 mg/mL, about 0.6 mg/mL, about 0.7 mg/mL, about 0.8 mg/mL, about 0.9 mg/mL, or about 1 mg/mL. In some embodiments, the acetic acid is present in the pharmaceutical formulation at a concentration of 0.6 mg/mL.

A pharmaceutical formulation described herein can contain, for example, acetaminophen, pregabalin, sodium chloride, and sodium dihydrogen phosphate. The pharmaceutical formulation can be at, for example, pH 5, 5.5, or 6. In some embodiments, the pH of the pharmaceutical formulation is 6. The acetaminophen can be present in the pharmaceutical formulation at a concentration of about 5 mg/mL, about 6 mg/mL, about 7 mg/mL, about 8 mg/mL, about 9 mg/mL, or about 10 mg/mL. In some embodiments, the acetaminophen is present in the pharmaceutical formulation at a concentration of 10 mg/mL. The pregabalin can be present in the pharmaceutical formulation a concentration of about 4 mg/mL, about 4.5 mg/ml, or about 5 mg/mL. In some embodiments, the pregabalin is present in the pharmaceutical formulation at a concentration of 4.5 mg/mL. The sodium chloride can be present in the pharmaceutical formulation at a concentration of about 4 mg/mL, about 4.5 mg/mL, about 5 mg/mL, about 5.5 mg/mL, or about 6 mg/mL. In some embodiments, the sodium chloride is present in the pharmaceutical formulation at a concentration of 5.5 mg/mL. The sodium dihydrogen phosphate can be present in the pharmaceutical formulation at a concentration of about 1 mg/mL, about 1.1 mg/mL, about 1.2 mg/mL, about 1.3 mg/mL, about 1.4 mg/mL, about 1.5 mg/mL, about 1.6 mg/mL, about 1.7 mg/mL, about 1.8 mg/mL, about 1.9 mg/mL, or about 2 mg/mL. In some embodiments, the sodium dihydrogen phosphate is present in the pharmaceutical formulation at a concentration of 1.2 mg/mL.

Sodium chloride can be a present in a pharmaceutical formulation described herein at a concentration of about 0.1 mg/mL, about 0.2 mg/mL, about 0.3 mg/mL, about 0.4 mg/mL, about 0.5 mg/mL, about 0.6 mg/mL, about 0.7 mg/mL, about 0.8 mg/mL, about 0.9 mg/mL, about 1 mg/mL, about 1.1 mg/mL, about 1.2 mg/mL, about 1.3 mg/mL, about 1.4 mg/mL, about 1.5 mg/mL, about 1.6 mg/mL, about 1.7 mg/mL, about 1.8 mg/mL, about 1.9 mg/mL, about 2 mg/mL, about 2.1 mg/mL, about 2.2 mg/mL, about 2.3 mg/mL, about 2.4 mg/mL, about 2.5 mg/mL, about 2.6 mg/mL, about 2.7 mg/mL, about 2.8 mg/mL, about 2.9 mg/mL, about 3 mg/mL, about 3.1 mg/mL, about 3.2 mg/mL, about 3.3 mg/mL, about 3.4 mg/mL, about 3.5 mg/mL, about 3.6 mg/mL, about 3.7 mg/mL, about 3.8 mg/mL, about 3.9 mg/mL, about 4 mg/mL, about 4.1 mg/mL, about 4.2 mg/mL, about 4.3 mg/mL, about 4.4 mg/mL, about 4.5 mg/mL, about 4.6 mg/mL, about 4.7 mg/mL, about 4.8 mg/mL, about 4.9 mg/mL, about 5 mg/mL, about 5.1 mg/mL, about 5.2 mg/mL, about 5.3 mg/mL, about 5.4 mg/mL, about 5.5 mg/mL, about 5.6 mg/mL, about 5.7 mg/mL, about 5.8 mg/mL, about 5.9 mg/mL, or about 6 mg/mL. Sodium chloride can be present in a pharmaceutical formulation described herein at a concentration from about 0.1 mg/mL to about 0.5 mg/mL, about 0.2 mg/mL to about 0.6 mg/mL, about 0.3 mg/mL to about 0.7 mg/mL, about 0.4 mg/mL to about 0.8 mg/mL, about 0.5 mg/mL to about 1 mg/mL, about 0.6 mg/mL to about 1.1 mg/mL, about 0.7 mg/mL to about 1.2 mg/mL, about 0.8 mg/mL to about 1.3 mg/mL, about 0.9 mg/mL to about 1.4 mg/mL, about 1 mg/mL to about 1.5 mg/mL, about 1.1 mg/mL to about 1.6 mg/mL, about 1.2 mg/mL to about 1.7 mg/mL, about 1.3 mg/mL to about 1.8 mg/mL, about 1.4 mg/mL to about 1.9 mg/mL, about 1.5 mg/mL to about 2 mg/mL, about 1.6 mg/mL to about 2.1 mg/mL, about 2.2 mg/mL to about 2.7 mg/mL, about 2.3 mg/mL to about 2.8 mg/mL, about 2.4 mg/mL to about 2.9 mg/mL, about 2.5 mg/mL to about 3 mg/mL, about 2.6 mg/mL to about 3.1 mg/mL, about 2.7 mg/mL to about 3.2 mg/mL, about 2.8 mg/mL to about 3.3 mg/mL, about 2.9 mg/mL to about 3.4 mg/mL, about 3 mg/mL to about 3.5 mg/mL, about 3.1 mg/mL to about 3.6 mg/mL, about 3.2 mg/mL to about 3.7 mg/mL, about 3.3 mg/mL to about 3.8 mg/mL, about 3.4 mg/mL to about 3.9 mg/mL, about 3.5 mg/mL to about 4 mg/mL, about 3.6 mg/mL to about 4.1 mg/mL, about 3.7 mg/mL to about 4.2 mg/mL, about 3.8 mg/mL to about 4.3 mg/mL, about 3.9 mg/mL to about 4.4 mg/mL, about 4 mg/mL to about 4.5 mg/mL, about 4.1 mg/mL to about 4.6 mg/mL, about 4.2 mg/mL to about 4.7 mg/mL, about 4.3 mg/mL to about 4.8 mg/mL, about 4.4 mg/mL to about 4.9 mg/mL, about 4.5 mg/mL to about 5 mg/mL, about 4.6 mg/mL to about 5.1 mg/mL, about 4.7 mg/mL to about 5.2 mg/mL, about 4.8 mg/mL to about 5.3 mg/mL, about 4.9 mg/mL to about 5.4 mg/mL, about 5 mg/mL to about 5.5 mg/mL, about 5.1 mg/mL to about 5.6 mg/mL, about 5.2 mg/mL to about 5.7 mg/mL, about 5.3 mg/mL to about 5.8 mg/mL, about 5.4 mg/mL to about 5.9 mg/mL, or about 5.5 mg/mL to about 6 mg/mL.

L-Histidine can be a present in a pharmaceutical formulation described herein at a concentration of about 0.1 mg/mL, about 0.2 mg/mL, about 0.3 mg/mL, about 0.4 mg/mL, about 0.5 mg/mL, about 0.6 mg/mL, about 0.7 mg/mL, about 0.8 mg/mL, about 0.9 mg/mL, about 1 mg/mL, about 1.1 mg/mL, about 1.2 mg/mL, about 1.3 mg/mL, about 1.4 mg/mL, about 1.5 mg/mL, about 1.6 mg/mL, about 1.7 mg/mL, about 1.8 mg/mL, about 1.9 mg/mL, about 2 mg/mL, about 2.1 mg/mL, about 2.2 mg/mL, about 2.3 mg/mL, about 2.4 mg/mL, about 2.5 mg/mL, about 2.6 mg/mL, about 2.7 mg/mL, about 2.8 mg/mL, about 2.9 mg/mL, about 3 mg/mL, about 3.1 mg/mL, about 3.2 mg/mL, about 3.3 mg/mL, about 3.4 mg/mL, about 3.5 mg/mL, about 3.6 mg/mL, about 3.7 mg/mL, about 3.8 mg/mL, about 3.9 mg/mL, about 4 mg/mL, about 4.1 mg/mL, about 4.2 mg/mL, about 4.3 mg/mL, about 4.4 mg/mL, about 4.5 mg/mL, about 4.6 mg/mL, about 4.7 mg/mL, about 4.8 mg/mL, about 4.9 mg/mL, about 5 mg/mL, about 5.1 mg/mL, about 5.2 mg/mL, about 5.3 mg/mL, about 5.4 mg/mL, about 5.5 mg/mL, about 5.6 mg/mL, about 5.7 mg/mL, about 5.8 mg/mL, about 5.9 mg/mL, or about 6 mg/mL. L-Histidine can be present in a pharmaceutical formulation described herein at a concentration from about 0.1 mg/mL to about 0.5 mg/mL, about 0.2 mg/mL to about 0.6 mg/mL, about 0.3 mg/mL to about 0.7 mg/mL, about 0.4 mg/mL to about 0.8 mg/mL, about 0.5 mg/mL to about 1 mg/mL, about 0.6 mg/mL to about 1.1 mg/mL, about 0.7 mg/mL to about 1.2 mg/mL, about 0.8 mg/mL to about 1.3 mg/mL, about 0.9 mg/mL to about 1.4 mg/mL, about 1 mg/mL to about 1.5 mg/mL, about 1.1 mg/mL to about 1.6 mg/mL, about 1.2 mg/mL to about 1.7 mg/mL, about 1.3 mg/mL to about 1.8 mg/mL, about 1.4 mg/mL to about 1.9 mg/mL, about 1.5 mg/mL to about 2 mg/mL, about 1.6 mg/mL to about 2.1 mg/mL, about 2.2 mg/mL to about 2.7 mg/mL, about 2.3 mg/mL to about 2.8 mg/mL, about 2.4 mg/mL to about 2.9 mg/mL, about 2.5 mg/mL to about 3 mg/mL, about 2.6 mg/mL to about 3.1 mg/mL, about 2.7 mg/mL to about 3.2 mg/mL, about 2.8 mg/mL to about 3.3 mg/mL, about 2.9 mg/mL to about 3.4 mg/mL, about 3 mg/mL to about 3.5 mg/mL, about 3.1 mg/mL to about 3.6 mg/mL, about 3.2 mg/mL to about 3.7 mg/mL, about 3.3 mg/mL to about 3.8 mg/mL, about 3.4 mg/mL to about 3.9 mg/mL, about 3.5 mg/mL to about 4 mg/mL, about 3.6 mg/mL to about 4.1 mg/mL, about 3.7 mg/mL to about 4.2 mg/mL, about 3.8 mg/mL to about 4.3 mg/mL, about 3.9 mg/mL to about 4.4 mg/mL, about 4 mg/mL to about 4.5 mg/mL, about 4.1 mg/mL to about 4.6 mg/mL, about 4.2 mg/mL to about 4.7 mg/mL, about 4.3 mg/mL to about 4.8 mg/mL, about 4.4 mg/mL to about 4.9 mg/mL, about 4.5 mg/mL to about 5 mg/mL, about 4.6 mg/mL to about 5.1 mg/mL, about 4.7 mg/mL to about 5.2 mg/mL, about 4.8 mg/mL to about 5.3 mg/mL, about 4.9 mg/mL to about 5.4 mg/mL, about 5 mg/mL to about 5.5 mg/mL, about 5.1 mg/mL to about 5.6 mg/mL, about 5.2 mg/mL to about 5.7 mg/mL, about 5.3 mg/mL to about 5.8 mg/mL, about 5.4 mg/mL to about 5.9 mg/mL, or about 5.5 mg/mL to about 6 mg/mL.

Citric acid monohydrate or sodium dihydrogen phosphate can be a present in a pharmaceutical formulation described herein at a concentration of about 0.1 mg/mL, about 0.2 mg/mL, about 0.3 mg/mL, about 0.4 mg/mL, about 0.5 mg/mL, about 0.6 mg/mL, about 0.7 mg/mL, about 0.8 mg/mL, about 0.9 mg/mL, about 1 mg/mL, about 1.1 mg/mL, about 1.2 mg/mL, about 1.3 mg/mL, about 1.4 mg/mL, about 1.5 mg/mL, about 1.6 mg/mL, about 1.7 mg/mL, about 1.8 mg/mL, about 1.9 mg/mL, about 2 mg/mL, about 2.1 mg/mL, about 2.2 mg/mL, about 2.3 mg/mL, about 2.4 mg/mL, about 2.5 mg/mL, about 2.6 mg/mL, about 2.7 mg/mL, about 2.8 mg/mL, about 2.9 mg/mL, about 3 mg/mL, about 3.1 mg/mL, about 3.2 mg/mL, about 3.3 mg/mL, about 3.4 mg/mL, about 3.5 mg/mL, about 3.6 mg/mL, about 3.7 mg/mL, about 3.8 mg/mL, about 3.9 mg/mL, about 4 mg/mL, about 4.1 mg/mL, about 4.2 mg/mL, about 4.3 mg/mL, about 4.4 mg/mL, about 4.5 mg/mL, about 4.6 mg/mL, about 4.7 mg/mL, about 4.8 mg/mL, about 4.9 mg/mL, about 5 mg/mL, about 5.1 mg/mL, about 5.2 mg/mL, about 5.3 mg/mL, about 5.4 mg/mL, about 5.5 mg/mL, about 5.6 mg/mL, about 5.7 mg/mL, about 5.8 mg/mL, about 5.9 mg/mL, or about 6 mg/mL. Citric acid monohydrate or sodium dihydrogen phosphate can be present in a pharmaceutical formulation described herein at a concentration from about 0.1 mg/mL to about 0.5 mg/mL, about 0.2 mg/mL to about 0.6 mg/mL, about 0.3 mg/mL to about 0.7 mg/mL, about 0.4 mg/mL to about 0.8 mg/mL, about 0.5 mg/mL to about 1 mg/mL, about 0.6 mg/mL to about 1.1 mg/mL, about 0.7 mg/mL to about 1.2 mg/mL, about 0.8 mg/mL to about 1.3 mg/mL, about 0.9 mg/mL to about 1.4 mg/mL, about 1 mg/mL to about 1.5 mg/mL, about 1.1 mg/mL to about 1.6 mg/mL, about 1.2 mg/mL to about 1.7 mg/mL, about 1.3 mg/mL to about 1.8 mg/mL, about 1.4 mg/mL to about 1.9 mg/mL, about 1.5 mg/mL to about 2 mg/mL, about 1.6 mg/mL to about 2.1 mg/mL, about 2.2 mg/mL to about 2.7 mg/mL, about 2.3 mg/mL to about 2.8 mg/mL, about 2.4 mg/mL to about 2.9 mg/mL, about 2.5 mg/mL to about 3 mg/mL, about 2.6 mg/mL, about 3.1 mg/mL, about 2.7 mg/mL to about 3.2 mg/mL, about 2.8 mg/mL to about 3.3 mg/mL, about 2.9 mg/mL to about 3.4 mg/mL, about 3 mg/mL to about 3.5 mg/mL, about 3.1 mg/mL to about 3.6 mg/mL, about 3.2 mg/mL to about 3.7 mg/mL, about 3.3 mg/mL to about 3.8 mg/mL, about 3.4 mg/mL to about 3.9 mg/mL, about 3.5 mg/mL to about 4 mg/mL, about 3.6 mg/mL to about 4.1 mg/mL, about 3.7 mg/mL to about 4.2 mg/mL, about 3.8 mg/mL to about 4.3 mg/mL, about 3.9 mg/mL to about 4.4 mg/mL, about 4 mg/mL to about 4.5 mg/mL, about 4.1 mg/mL to about 4.6 mg/mL, about 4.2 mg/mL to about 4.7 mg/mL, about 4.3 mg/mL to about 4.8 mg/mL, about 4.4 mg/mL to about 4.9 mg/mL, about 4.5 mg/mL to about 5 mg/mL, about 4.6 mg/mL to about 5.1 mg/mL, about 4.7 mg/mL to about 5.2 mg/mL, about 4.8 mg/mL to about 5.3 mg/mL, about 4.9 mg/mL to about 5.4 mg/mL, about 5 mg/mL to about 5.5 mg/mL, about 5.1 mg/mL to about 5.6 mg/mL, about 5.2 mg/mL to about 5.7 mg/mL, about 5.3 mg/mL to about 5.8 mg/mL, about 5.4 mg/mL to about 5.9 mg/mL, or about 5.5 mg/mL to about 6 mg/mL.

Acetic acid can be present in a pharmaceutical formulation described herein at a concentration of about 0.1 mg/mL, about 0.2 mg/mL, about 0.3 mg/mL, about 0.4 mg/mL, about 0.5 mg/mL, about 0.6 mg/mL, about 0.7 mg/mL, about 0.8 mg/mL, about 0.9 mg/mL, about 1 mg/mL, about 1.1 mg/mL, about 1.2 mg/mL, about 1.3 mg/mL, about 1.4 mg/mL, about 1.5 mg/mL, about 1.6 mg/mL, about 1.7 mg/mL, about 1.8 mg/mL, about 1.9 mg/mL, about 2 mg/mL, about 2.1 mg/mL, about 2.2 mg/mL, about 2.3 mg/mL, about 2.4 mg/mL, about 2.5 mg/mL, about 2.6 mg/mL, about 2.7 mg/mL, about 2.8 mg/mL, about 2.9 mg/mL, about 3 mg/mL, about 3.1 mg/mL, about 3.2 mg/mL, about 3.3 mg/mL, about 3.4 mg/mL, about 3.5 mg/mL, about 3.6 mg/mL, about 3.7 mg/mL, about 3.8 mg/mL, about 3.9 mg/mL, about 4 mg/mL, about 4.1 mg/mL, about 4.2 mg/mL, about 4.3 mg/mL, about 4.4 mg/mL, about 4.5 mg/mL, about 4.6 mg/mL, about 4.7 mg/mL, about 4.8 mg/mL, about 4.9 mg/mL, or about 5 mg/mL. Acetic acid can be present in a pharmaceutical formulation described herein at a concentration of about 0.1 mg/mL to about 0.5 mg/mL, about 0.2 mg/mL to about 0.6 mg/mL, about 0.3 mg/mL to about 0.7 mg/mL, about 0.4 mg/mL to about 0.8 mg/mL, about 0.5 mg/mL to about 1 mg/mL, about 0.6 mg/mL to about 1.1 mg/mL, about 0.7 mg/mL to about 1.2 mg/mL, about 0.8 mg/mL to about 1.3 mg/mL, about 0.9 mg/mL to about 1.4 mg/mL, about 1 mg/mL to about 1.5 mg/mL, about 1.1 mg/mL to about 1.6 mg/mL, about 1.2 mg/mL to about 1.7 mg/mL, about 1.3 mg/mL to about 1.8 mg/mL, about 1.4 mg/mL to about 1.9 mg/mL, about 1.5 mg/mL to about 2 mg/mL, about 1.6 mg/mL to about 2.1 mg/mL, about 2.2 mg/mL to about 2.7 mg/mL, about 2.3 mg/mL to about 2.8 mg/mL, about 2.4 mg/mL to about 2.9 mg/mL, about 2.5 mg/mL to about 3 mg/mL, about 2.6 mg/mL, about 3.1 mg/mL, about 2.7 mg/mL to about 3.2 mg/mL, about 2.8 mg/mL to about 3.3 mg/mL, about 2.9 mg/mL to about 3.4 mg/mL, about 3 mg/mL to about 3.5 mg/mL, about 3.1 mg/mL to about 3.6 mg/mL, about 3.2 mg/mL to about 3.7 mg/mL, about 3.3 mg/mL to about 3.8 mg/mL, about 3.4 mg/mL to about 3.9 mg/mL, about 3.5 mg/mL to about 4 mg/mL, about 3.6 mg/mL to about 4.1 mg/mL, about 3.7 mg/mL to about 4.2 mg/mL, about 3.8 mg/mL to about 4.3 mg/mL, about 3.9 mg/mL to about 4.4 mg/mL, about 4 mg/mL to about 4.5 mg/mL, about 4.1 mg/mL to about 4.6 mg/mL, about 4.2 mg/mL to about 4.7 mg/mL, about 4.3 mg/mL to about 4.8 mg/mL, about 4.4 mg/mL to about 4.9 mg/mL, or about 4.5 mg/mL to about 5 mg/mL.

A pharmaceutical agent that is disclosed herein can be made more soluble in a formulation by the addition of an additive or agent. The improvement of solubility of the formulation can increase by about 5%, about 10%, about 15%, about 20%, about 25%, about 30%, about 35%, about 40%, about 45%, about 50%, about 55%, about 60%, about 65%, about 70%, about 75% about 80%, about 85%, about 90%, about 95%, about 100%, about 110%, about 120%, about 130%, about 140%, about 150%, about 160%, about 170%, about 180%, about 190%, about 200%, about 225%, about 250%, about 275%, about 300%, about 325%, about 350%, about 375%, about 400%, about 450%, or about 500%.

A first compound, for example, pregabalin, of a pharmaceutical formulation described herein can be made more soluble by the addition of a second compound, for example, acetaminophen, described herein. The solubility of the first or second compound can increase by about 5%, about 10%, about 15%, about 20%, about 25%, about 30%, about 35%, about 40%, about 45%, about 50%, about 55%, about 60%, about 65%, about 70%, about 75% about 80%, about 85%, about 90%, about 95%, about 100%, about 110%, about 120%, about 130%, about 140%, about 150%, about 160%, about 170%, about 180%, about 190%, about 200%, about 225%, about 250%, about 275%, about 300%, about 325%, about 350%, about 375%, about 400%, about 450%, or about 500% in the presence of the other compound.

The stability of a pharmaceutical formulation described herein can be determined by analyzing the amount of active ingredient remaining over a specific time period at a specific temperature when formulated, for example, at a specific pH. Additionally, the stability of the pharmaceutical formulation can be assessed by determining the amount of impurities present in the pharmaceutical formulation over a specific time period at a specific temperature when formulated, for example, at a specific pH. The amount of active ingredient and impurities can be determined by, for example, high-performance liquid chromatography (HPLC).

A formulation disclosed herein can be stable for about 1 day, about 2 days, about 3 days, about 4 days, about 5 days, about 6 days, about 7 days, about 8 days, about 9 days, about 10 days, about 2 weeks, about 4 weeks, about 6 weeks, about 8 weeks, about 10 weeks, about 12 weeks, about 3 months, about 4 months, about 5 months, about 6 months, about 7 months, about 8 months, about 9 months, about 10 months, about 11 months, or about one year. A formulation disclosed herein can be stable, for example, at about 0° C., about 5° C., about 10° C., about 15° C., about 20° C., about 25° C., about 30° C., about 35° C., about 40° C., about 45° C., about 50° C., about 60° C., about 70° C., or about 80° C. A formulation described herein can be stable for or be stored for, for example, about 1 hour, about 2 hours, about 3 hours, about 4 hours, about 5 hours, about 6 hours, about 7 hours, about 8 hours, about 9 hours, about 10 hours, about 11 hours, about 12 hours, about 13 hours, about 14 hours, about 15 hours, about 16 hours, about 17 hours, about 18 hours, about 19 hours, about 20 hours, about 21 hours, about 22 hours, about 23 hours, about 24 hours, about 30 hours, about 36 hours, about 42 hours, about 48 hours, about 60 hours, about 3 days, about 4 days, about 5 days, about 6 days, about 1 week, about 2 weeks, about 3 weeks, about 4 weeks, about 5 weeks, about 6 weeks, about 7 weeks, about 8 weeks, about 9 weeks, about 10 weeks, about 11 weeks, about 3 months, about 4 months, about 5 months, about 6 months, about 7 months, about 8 months, about 9 months, about 10 months, about 11 months, about 1 year, about 13 months, about 14 months, about 15 months, about 16 months, about 17 months, about 18 months, about 19 months, about 20 months, about 21 months, about 22 months, about 23 months, about 2 years, about 25 months, about 26 months, about 27 months, about 28 months, about 29 months, about 30 months, about 31 months, about 32 months, about 33 months, about 34 months, about 35 months, or about 3 years prior to administration to a subject.

A unit dosage form described herein can be stable for or be stored for, for example, about 1 hour, about 2 hours, about 3 hours, about 4 hours, about 5 hours, about 6 hours, about 7 hours, about 8 hours, about 9 hours, about 10 hours, about 11 hours, about 12 hours, about 13 hours, about 14 hours, about 15 hours, about 16 hours, about 17 hours, about 18 hours, about 19 hours, about 20 hours, about 21 hours, about 22 hours, about 23 hours, about 24 hours, about 30 hours, about 36 hours, about 42 hours, about 48 hours, about 60 hours, about 3 days, about 4 days, about 5 days, about 6 days, about 1 week, about 2 weeks, about 3 weeks, about 4 weeks, about 5 weeks, about 6 weeks, about 7 weeks, about 8 weeks, about 9 weeks, about 10 weeks, about 11 weeks, about 3 months, about 4 months, about 5 months, about 6 months, about 7 months, about 8 months, about 9 months, about 10 months, about 11 months, about 1 year, about 13 months, about 14 months, about 15 months, about 16 months, about 17 months, about 18 months, about 19 months, about 20 months, about 21 months, about 22 months, about 23 months, about 2 years, about 25 months, about 26 months, about 27 months, about 28 months, about 29 months, about 30 months, about 31 months, about 32 months, about 33 months, about 34 months, about 35 months, or about 3 years prior to administration to a subject.

The stability of a formulation described herein can be measured after, for example, about 1 hour, about 2 hours, about 3 hours, about 4 hours, about 5 hours, about 6 hours, about 7 hours, about 8 hours, about 9 hours, about 10 hours, about 11 hours, about 12 hours, about 13 hours, about 14 hours, about 15 hours, about 16 hours, about 17 hours, about 18 hours, about 19 hours, about 20 hours, about 21 hours, about 22 hours, about 23 hours, about 24 hours, about 30 hours, about 36 hours, about 42 hours, about 48 hours, about 60 hours, about 3 days, about 4 days, about 5 days, about 6 days, about 1 week, about 2 weeks, about 3 weeks, about 4 weeks, about 5 weeks, about 6 weeks, about 7 weeks, about 8 weeks, about 9 weeks, about 10 weeks, about 11 weeks, about 3 months, about 4 months, about 5 months, about 6 months, about 7 months, about 8 months, about 9 months, about 10 months, about 11 months, about 1 year, about 13 months, about 14 months, about 15 months, about 16 months, about 17 months, about 18 months, about 19 months, about 20 months, about 21 months, about 22 months, about 23 months, about 2 years, about 25 months, about 26 months, about 27 months, about 28 months, about 29 months, about 30 months, about 31 months, about 32 months, about 33 months, about 34 months, about 35 months, or about 3 years.

Pharmaceutical compositions described herein can be used, stored, tested, analyzed or assayed at any suitable temperature. Non-limiting examples of temperatures include about 0° C., about 1° C., about 2° C., about 3° C., about 4° C., about 5° C., about 6° C., about 7° C., about 8° C., about 9° C., about 10° C., about 11° C., about 12° C., about 13° C., about 14° C., about 15° C., about 16° C., about 17° C., about 18° C., about 19° C., about 20° C., about 21° C., about 22° C., about 23° C., about 24° C., about 25° C., about 26° C., about 27° C., about 28° C., about 29° C., about 30° C., about 31° C., about 32° C., about 33° C., about 34° C., about 35° C., about 36° C., about 37° C., about 38° C., about 39° C., about 40° C., about 41° C., about 42° C., about 43° C., about 44° C., about 45° C., about 46° C., about 47° C., about 48° C., about 49° C., about 50° C., about 51° C., about 52° C., about 53° C., about 54° C., about 55° C., about 56° C., about 57° C., about 58° C., about 59° C., about 60° C., about 61° C., about 62° C., about 63° C., about 64° C., about 65° C., about 66° C., about 67° C., about 68° C., about 69° C., about 70° C., about 71° C., about 72° C., about 73° C., about 74° C., or about 75° C.

Pharmaceutical compositions described herein can be used, stored, tested, analyzed or assayed at room temperature. The room temperature can be, for example, about 20.0° C., about 20.1° C., about 20.2° C., about 20.3° C., about 20.4° C., about 20.5° C., about 20.6° C., about 20.7° C., about 20.8° C., about 20.9° C., about 21.0° C., about 21.1° C., about 21.2° C., about 21.3° C., about 21.4° C., about 21.5° C., about 21.6° C., about 21.7° C., about 21.8° C., about 21.9° C., about 22.0° C., about 22.1° C., about 22.2° C., about 22.3° C., about 22.4° C., about 22.5° C., about 22.6° C., about 22.7° C., about 22.8° C., about 22.9° C., about 23.0° C., about 23.1° C., about 23.2° C., about 23.3° C., about 23.4° C., about 23.5° C., about 23.6° C., about 23.7° C., about 23.8° C., about 23.9° C., about 24.0° C., about 24.1° C., about 24.2° C., about 24.3° C., about 24.4° C., about 24.5° C., about 24.6° C., about 24.7° C., about 24.8° C., about 24.9° C., or about 25.0° C.

A pharmaceutical composition described herein can be supplied, stored, or delivered in a vial, tube, container, bag, or vessel that is, for example, about 0.5 mL, about 1 mL, about 2 mL, about 3 mL, about 4 mL, about 5 mL, about 6 mL, about 7 mL, about 8 mL, about 9 mL, about 10 mL, about 11 mL, about 12 mL, about 13 mL, about 14 mL, about 15 mL, about 16 mL, about 17 mL, about 18 mL, about 19 mL, about 20 mL, about 25 mL, about 30 mL, about 35 mL, about 40 mL, about 45 mL, about 50 mL, about 60 mL, about 70 mL, about 80 mL, about 90 mL, about 100 mL, about 150 mL, or about 200 mL in volume.

A pharmaceutical formulation described herein can be disposed in a container or vessel, which can be sealed. The container or vessel can maintain the sterility of, or reduce the likelihood of contamination of, the pharmaceutical formulation. The pharmaceutical formulation described herein can be disposed in a container or vessel and is formulated as, for example, a single use dosage or a multiple use dosage. The container or vessel can be, for example, a glass vial, an ampoule, or a plastic flexible container. The plastic flexible container can be made of, for example, PVC (polyvinyl chloride), or polypropylene. A container can be a prefilled syringe.

A pharmaceutical formulation described herein can be stored as a liquid in an aliquot having a total volume of between about 1 and about 500 mL, between about 1 and about 250 mL, between about 1 and about 200 mL, between about 1 and about 150 mL, between about 1 and about 125 mL, between about 1 and about 120 mL, between about 1 and about 110 mL, between about 1 and about 100 mL, between about 1 and about 90 mL, between about 1 and about 80 mL, between about 1 and about 70 mL, between about 1 and about 60 mL, between about 1 and about 50 mL, between about 1 and about 40 mL, between about 1 and about 30 mL, between about 1 and about 20 mL, between about 1 and about 10 mL, or between about 1 and about 5 mL.

Dosage Amounts.

In practicing the methods of treatment or use provided herein, therapeutically-effective amounts of the compounds described herein are administered in pharmaceutical compositions to a subject having a disease or condition to be treated. A therapeutically-effective amount can vary widely depending on the severity of the disease, the age and relative health of the subject, the potency of the compounds used, and other factors. Subjects can be, for example, humans, elderly adults, adults, adolescents, pre-adolescents, children, toddlers, infants, or neonates. A subject can be a patient.

Pharmaceutical compositions described herein can be formulated in any suitable volume. The formulation volume can be, for example, about 0.1 mL, about 0.2 mL, about 0.3 mL, about 0.4 mL, about 0.5 mL, about 0.6 mL, about 0.7 mL, about 0.8 mL, about 0.9 mL, about 1 mL, about 1.1 mL, about 1.2 mL, about 1.3 mL, about 1.4 mL, about 1.5 mL, about 1.6 mL, about 1.7 mL, about 1.8 mL, about 1.9 mL, about 2 mL, about 2.1 mL, about 2.2 mL, about 2.3 mL, about 2.4 mL, about 2.5 mL, about 2.6 mL, about 2.7 mL, about 2.8 mL, about 2.9 mL, about 3 mL, about 3.1 mL, about 3.2 mL, about 3.3 mL, about 3.4 mL, about 3.5 mL, about 3.6 mL, about 3.7 mL, about 3.8 mL, about 3.9 mL, about 4 mL, about 4.1 mL, about 4.2 mL, about 4.3 mL, about 4.4 mL, about 4.5 mL, about 4.6 mL, about 4.7 mL, about 4.8 mL, about 4.9 mL, about 5 mL, about 5.1 mL, about 5.2 mL, about 5.3 mL, about 5.4 mL, about 5.5 mL, about 5.6 mL, about 5.7 mL, about 5.8 mL, about 5.9 mL, about 6 mL, about 6.1 mL, about 6.2 mL, about 6.3 mL, about 6.4 mL, about 6.5 mL, about 6.6 mL, about 6.7 mL, about 6.8 mL, about 6.9 mL, about 7 mL, about 7.1 mL, about 7.2 mL, about 7.3 mL, about 7.4 mL, about 7.5 mL, about 7.6 mL, about 7.7 mL, about 7.8 mL, about 7.9 mL, about 8 mL, about 8.1 mL, about 8.2 mL, about 8.3 mL, about 8.4 mL, about 8.5 mL, about 8.6 mL, about 8.7 mL, about 8.8 mL, about 8.9 mL, about 9 mL, about 9.1 mL, about 9.2 mL, about 9.3 mL, about 9.4 mL, about 9.5 mL, about 9.6 mL, about 9.7 mL, about 9.8 mL, about 9.9 mL, about 10 mL, about 11 mL, about 12 mL, about 13 mL, about 14 mL, about 15 mL, about 16 mL, about 17 mL, about 18 mL, about 19 mL, about 20 mL, about 30 mL, about 40 mL, about 50 mL, about 60 mL, about 70 mL, about 80 mL, about 90 mL, about 100 mL, about 150 mL, or about 200 mL. The formulation volume can be, for example, about 0.1 mL to about 200 mL, about 0.1 mL to about 100 mL, about 0.1 mL to about 50 mL, about 0.1 mL to about 25 mL, about 0.1 mL to about 20 mL, about 0.1 mL to about 15 mL, about 0.1 mL to about 10 mL, about 0.1 mL to about 5 mL, about 0.1 mL to about 3 mL, about 0.1 mL to about 2 mL, about 0.1 mL to about 1 mL, about 1 mL to about 10 mL, about 1 mL to about 5 mL, about 1 mL to about 3 mL, or about 1 mL to about 2 mL.

A therapeutically-effective amount of a compound described herein can be present in a composition described herein at a mass of, for example, about 0.01 µg, about 0.05 µg, about 0.1 µg, about 0.15 µg, about 0.2 µg, about 0.25 µg, about 0.3 µg, about 0.35 µg, about 0.4 µg, about 0.5 µg, about 0.6 µg, about 0.7 µg, about 0.8 µg, about 0.9 µg, about 1 µg, about 2 µg, about 3 µg, about 4 µg, about 5 µg, about 10 µg, about 15 µg, about 20 µg, about 25 µg, about 30 µg, about 35 µg, about 40 µg, about 45 µg, about 50 µg, about 60 µg, about 70 µg, about 80 µg, about 90 µg, about 100 µg, about 125 µg, about 150 µg, about 175 µg, about 200 µg, about 250 µg, about 300 µg, about 350 µg, about 400 µg, about 450 µg, about 500 µg, about 600 µg, about 700 µg, about 800 µg, about 900 µg, about 1 mg, about 2 mg, about 3 mg, about 4 mg, about 5 mg, about 6 mg, about 7 mg, about 8 mg, about 9 mg, about 10 mg, about 11 mg, about 12 mg, about 13 mg, about 14 mg, about 15 mg, about 16 mg, about 17 mg, about 18 mg, about 19 mg, or about 20 mg. A therapeutically-effective amount of a compound described herein can be present in a composition described herein at a mass of, for example, about 0.01 µg to about 20 mg, about 0.01 µg to about 1 mg, about 0.01 µg to about 100 µg, about 0.01 µg to about 10 µg, about 0.1 µg to about 10 µg, about 1 µg to about 10 µg, about 500 µg, to about 1 mg, about 1 mg to about 20 mg, about 1 mg to about 10 mg, about 1 mg to about 5 mg, about 1 mg to about 2 mg, about 5 mg to about 20 mg, or about 10 mg to about 20 mg.

A therapeutically-effective amount of a compound described herein can be present in a composition described herein at a concentration of, for example, about 0.001 mg/mL, about 0.002 mg/mL, about 0.003 mg/mL, about 0.004 mg/mL, about 0.005 mg/mL, about 0.006 mg/mL, about 0.007 mg/mL, about 0.008 mg/mL, about 0.009 mg/mL, about 0.01 mg/mL, about 0.02 mg/mL, about 0.03 mg/mL, about 0.04 mg/mL, about 0.05 mg/mL, about 0.06 mg/mL, about 0.07 mg/mL, about 0.08 mg/mL, about 0.09 mg/mL, about 0.1 mg/mL, about 0.2 mg/mL, about 0.25 mg/mL, about 0.3 mg/mL, about 0.4 mg/mL, about 0.5 mg/mL, about 0.6 mg/mL, about 0.7 mg/mL, about 0.8 mg/mL, about 0.9 mg/mL, about 1 mg/mL, about 1.5 mg/mL, about 2 mg/mL, about 2.5 mg/mL, about 3 mg/mL, about 3.5 mg/mL, about 4 mg/mL, about 4.5 mg/mL, about 5 mg/mL, about 6 mg/mL, about 7 mg/mL, about 8 mg/mL, about 9 mg/mL, about 10 mg/mL, about 15 mg/mL, about 20 mg/mL, about 25 mg/mL, about 30 mg/mL, about 35 mg/mL, about 40 mg/mL, about 45 mg/mL, about 50 mg/mL, about 60 mg/mL, about 70 mg/mL, about 80 mg/mL, about 90 mg/mL, or about 100 mg/mL. A therapeutically-effective amount of a compound described herein can be present in a composition described herein at a concentration of, for example, from about 0.1 mg/mL to about 20 mg/mL, from about 0.1 mg/mL to about 50 mg/mL, from about 0.25 mg/mL to about 6 mg/mL, from about 1 mg/mL to about 20 mg/mL, from about 2 mg/mL to about 20 mg/mL, from about 5 mg/mL to about 15 mg/mL, from about 8 mg/mL to about 12 mg/mL, from about 9 mg/mL to about 11 mg/mL, from about 9.5 mg/mL to about 10.5 mg/mL, from about 9.9 mg/mL to about 10.1 mg/mL, from about 3 mg/mL to about 6 mg/mL, from about 3.5 mg/mL to about 5.5 mg/mL, from about 4 mg/mL to about 5 mg/mL, or from about 4.4 mg/mL to about 4.6 mg/mL. A therapeutically-effective amount of a compound described herein can be present in a composition described herein at a concentration of, for example, at least about 0.5 mg/mL, at least about 1 mg/mL, at least about 1.5 mg/mL, at least about 3 mg/mL, or at least about 5 mg/mL. In the same formulation, the therapeutically-effective amount of acetaminophen can be at least about 8 mg/mL, at least about 10 mg/mL, at least about 15 mg/mL, or at least about 20 mg/mL.

A therapeutically-effective amount of a compound described herein can be a dose based on the body mass of the subject, for example, about 0.5 mg/kg, about 1 mg/kg, about 1.25 mg/kg, about 1.5 mg/kg, about 1.75 mg/kg, about 2 mg/kg, about 2.25 mg/kg, about 2.5 mg/kg, about 2.75 mg/kg, about 3 mg/kg, about 3.25 mg/kg, about 3.5 mg/kg, about 3.75 mg/kg, about 4 mg/kg, about 4.25 mg/kg, about 4.5 mg/kg, about 4.75 mg/kg, about 5 mg/kg, about 5.25 mg/kg, about 5.5 mg/kg, about 5.75 mg/kg, about 6 mg/kg, about 6.25 mg/kg, about 6.5 mg/kg, about 6.75 mg/kg, about 7 mg/kg, about 7.25 mg/kg, about 7.5 mg/kg, about 7.75 mg/kg, about 8 mg/kg, about 8.25 mg/kg, about 8.5 mg/kg, about 8.75 mg/kg, about 9 mg/kg, about 9.25 mg/kg, about 9.5 mg/kg, about 9.75 mg/kg, about 10 mg/kg, about 11 mg/kg, about 12 mg/kg, about 13 mg/kg, about 14 mg/kg, about 15 mg/kg, about 16 mg/kg, about 17 mg/kg, about 18 mg/kg, about 19 mg/kg, about 20 mg/kg, about 25 mg/kg, about 30 mg/kg, about 35 mg/kg, about 40 mg/kg, about 45 mg/kg, or about 50 mg/kg. A therapeutically-effective amount of a compound described herein can be a dose based on the body mass of the subject, for example, about 0.5 mg/kg to about 50 mg/kg, about 0.5 mg/kg to about 1 mg/kg, about 1 mg/kg to about 5 mg/kg, about 5 mg/kg to about 10 mg/kg, about 10 mg/kg to about 15 mg/kg, about 15 mg/kg to about 20 mg/kg, about 20 mg/kg to about 25 mg/kg, about 25 mg/kg to about 30 mg/kg, about 30 mg/kg to about 35 mg/kg, about 35 mg/kg to about 40 mg/kg, about 40 mg/kg to about 45 mg/kg, or about 45 mg/kg to about 50 mg/kg.

Pharmaceutical compositions described herein can be formulated at any suitable pH. The pH can be, for example, about 2, about 2.05, about 2.1, about 2.15, about 2.2, about 2.25, about 2.3, about 2.35, about 2.4, about 2.45, about 2.5, about 2.55, about 2.6, about 2.65, about 2.7, about 2.75, about 2.8, about 2.85, about 2.9, about 2.95, about 3, about 3.05, about 3.1, about 3.15, about 3.2, about 3.25, about 3.3, about 3.35, about 3.4, about 3.45, about 3.5, about 3.55, about 3.6, about 3.65, about 3.7, about 3.75, about 3.8, about 3.85, about 3.9, about 3.95, about 4, about 4.05, about 4.1, about 4.15, about 4.2, about 4.25, about 4.3, about 4.35, about 4.4, about 4.45, about 4.5, about 4.55, about 4.6, about 4.65, about 4.7, about 4.75, about 4.8, about 4.85, about 4.9, about 4.95, about 5, about 5.05, about 5.1, about 5.15, about 5.2, about 5.25, about 5.3, about 5.35, about 5.4, about 5.45, about 5.5, about 5.55, about 5.6, about 5.65, about 5.7, about 5.75, about 5.8, about 5.85, about 5.9, about 5.95, about 6, about 6.05, about 6.1, about 6.15, about 6.2, about 6.25, about 6.3, about 6.35, about 6.4, about 6.45, about 6.5, about 6.55, about 6.6, about 6.65, about 6.7, about 6.75, about 6.8, about 6.85, about 6.9, about 6.95, about 7, about 7.05, about 7.1, about 7.15, about 7.2, about 7.25, about 7.3, about 7.35, about 7.4, about 7.45, about 7.5, about 7.55, about 7.6, about 7.65, about 7.7, about 7.75, about 7.8, about 7.85, about 7.9, about 7.95, or about 8.

Pharmaceutical compositions described herein can be formulated at any suitable pH. The pH can be, for example, from about 2 to about 2.2, about 2.05 to about 2.25, about 2.1 to about 2.3, about 2.15 to about 2.35, about 2.2 to about 2.4, about 2.25 to about 2.45, about 2.3 to about 2.5, about 2.35 to about 2.55, about 2.4 to about 2.6, about 2.45 to about 2.65, about 2.5 to about 2.7, about 2.55 to about 2.75, about 2.6 to about 2.8, about 2.65 to about 2.85, about 2.7 to about 2.9, about 2.75 to about 2.95, about 2.8 to about 3, about 2.85 to about 3.05, about 2.9 to about 3.1, about 2.95 to about 3.15, about 3 to about 3.2, about 3.05 to about 3.25, about 3.1 to about 3.3, about 3.15 to about 3.35, about 3.2 to about 3.4, about 3.25 to about 3.45, about 3.3 to about 3.5, about 3.35 to about 3.55, about 3.4 to about 3.6, about 3.45 to about 3.65, about 3.5 to about 3.7, about 3.55 to about 3.75, about 3.6 to about 3.8, about 3.65 to about 3.85, about 3.7 to about 3.9, about 3.7 to about 3.8, about 3.75 to about 3.95, about 3.75 to about 3.8, about 3.8 to about 3.85, about 3.75 to about 3.85, about 3.8 to about 4, about 3.85 to about 4.05, about 3.9 to about 4.1, about 3.95 to about 4.15, about 4 to about 4.2, about 4.05 to about 4.25, about 4.1 to about 4.3, about 4.15 to about 4.35, about 4.2 to about 4.4, about 4.25 to about 4.45, about 4.3 to about 4.5, about 4.35 to about 4.55, about 4.4 to about 4.6, about 4.45 to about 4.65, about 4.5 to about 4.7, about 4.55 to about 4.75, about 4.6 to about 4.8, about 4.65 to about 4.85, about 4.7 to about 4.9, about 4.75 to about 4.95, about 4.8 to about 5, about 4.85 to about 5.05, about 4.9 to about 5.1, about 4.95 to about 5.15, about 5 to about 5.2, about 5.05 to about 5.25, about 5.1 to about 5.3, about 5.15 to about 5.35, about 5.2 to about 5.4, about 5.25 to about 5.45, about 5.3 to about 5.5, about 5.35 to about 5.55, about 5.4 to about 5.6, about 5.45 to about 5.65, about 5.5 to about 5.7, about 5.55 to about 5.75, about 5.6 to about 5.8, about 5.65 to about 5.85, about 5.7 to about 5.9, about 5.75 to about 5.95, about 5.8 to about 6, about 5.85 to about 6.05, about 5.9 to about 6.1, about 5.95 to about 6.15, about 6 to about 6.2, about 6.05 to about 6.25, about 6.1 to about 6.3, about 6.1 to about 6.3, about 6.15 to about 6.35, about 6.2 to about 6.4, about 6.25 to about 6.45, about 6.3 to about 6.5, about 6.35 to about 6.55, about 6.4 to about 6.6, about 6.45 to about 6.65, about 6.5 to about 6.7, about 6.55 to about 6.85, about 6.6 to about 6.8, about 6.65 to about 6.85, about 6.7 to about 6.9, about 6.75 to about 6.95, about 6.8 to about 7, about 6.85 to about 7.05, about 6.9 to about 7.1, about 6.95 to about 7.15, about 7 to about 7.2, about 7.05 to about 7.25, about 7.1 to about 7.3, about 7.15 to about 7.35, about 7.2 to about 7.4, about 7.25 to about 7.45, about 7.3 to about 7.5, about 7.35 to about 7.55, about 7.4 to about 7.6, about 7.45 to about 7.65, about 7.5 to about 7.7, about 7.55 to about 7.75, about 7.6 to about 7.8, about 7.65 to about 7.85, about 7.7 to about 7.9, about 7.75 to about 7.95, about 7.8 to about 8, or about 7.85 to about 8.

In some embodiments, the pH of a pharmaceutical formulation described herein is about 4 to about 7. In some embodiments, the pH of a pharmaceutical formulation described herein is about 4 to about 6. In some embodiments, the pH of a pharmaceutical formulation described herein is about 5 to about 6. In some embodiments, the pH of a pharmaceutical formulation described herein is about 5.5 to about 6. In some embodiments, the pH of a pharmaceutical formulation described herein is 5.5. In some embodiments, the pH of a pharmaceutical formulation described herein is 6.

A pharmaceutical composition of the disclosure can be a combination of any pharmaceutical compounds described herein with other chemical components, such as carriers, stabilizers, diluents, dispersing agents, suspending agents, thickening agents, and/or excipients. The pharmaceutical composition facilitates administration of the compound to an organism. Pharmaceutical compositions can be administered by therapeutically-effective routes, for example, oral, intravenous, subcutaneous, intramuscular, subdermal, transdermal, or parenteral administration. A pharmaceutical formulation described herein can be administered as an intravenous infusion.

Pharmaceutical preparations can be formulated for intravenous administration as injectable formulations. The pharmaceutical formulations can be in a form suitable for parenteral injection as a sterile suspension, solution, or emulsion in oily or aqueous vehicles, and can contain formulation agents such as suspending, stabilizing, and/or dispersing agents. Pharmaceutical formulations for parenteral administration include aqueous solutions of the active compounds in water-soluble form. Suspensions of the active compounds can be prepared as oily injection suspensions. Suitable lipophilic solvents or vehicles include fatty oils such as sesame oil, or synthetic fatty acid esters, such as ethyl oleate or triglycerides, or liposomes. Aqueous injection suspensions can contain substances which increase the viscosity of the suspension, such as sodium carboxymethyl cellulose, sorbitol, or dextran. The suspension can also contain suitable stabilizers or agents which increase the solubility of the compounds to allow for the preparation of highly concentrated solutions. Alternatively, the active ingredient can be in powder form for constitution with a suitable vehicle, for example, sterile pyrogen-free water, before use.

Compositions described herein can be packaged as a kit. In some embodiments, a kit includes written instructions on the administration or use of the composition. The written material can be, for example, a label. The written material can suggest conditions methods of administration. The instructions provide the subject and the supervising physician with the best guidance for achieving the optimal clinical outcome from the administration of the therapy. In some embodiments, the label can be approved by a regulatory agency, for example the U.S. Food and Drug Administration (FDA), the European Medicines Agency (EMA), or other regulatory agencies.

A method of manufacture for a pharmaceutical composition described herein can involve manufacturing in a manufacturing tank. The manufacturing tank can contain water that has been, for example, deoxygenated. The deoxygenation of the water in the manufacturing tank can occur, via, for example, sparging using nitrogen, argon, or helium. The sparging can reduce the amount of oxygen in the water to about 0.01 ppm, about 0.02 ppm, about 0.03 ppm, about 0.04 ppm, about 0.05 ppm, about 0.1 ppm, about 0.15 ppm, about 0.2 ppm, about 0.25 ppm, about 0.3 ppm, about 0.35 ppm, about 0.4 ppm, about 0.45 ppm, about 0.5 ppm, about 0.6 ppm, about 0.7 ppm, about 0.8 ppm, about 0.9 ppm, about 1 ppm, about 1.5 ppm, or about 2 ppm.

Pharmaceutically-Acceptable Excipients.

Non-limiting examples of pharmaceutically-acceptable excipients can be found, for example, in Remington: The Science and Practice of Pharmacy, Nineteenth Ed (Easton, Pa.: Mack Publishing Company, 1995); Hoover, John E., Remington's Pharmaceutical Sciences, Mack Publishing Co., Easton, Pa. 1975; Liberman, H. A. and Lachman, L., Eds., Pharmaceutical Dosage Forms, Marcel Decker, New York, N.Y., 1980; and Pharmaceutical Dosage Forms and Drug Delivery Systems, Seventh Ed. (Lippincott Williams & Wilkins 1999), each of which is incorporated by reference in its entirety.

In some embodiments, the pharmaceutical composition provided herein comprises a buffer as an excipient. Non-limiting examples of buffers include potassium phosphate, sodium phosphate, phosphate buffer, citrate buffer, saline sodium citrate buffer (SSC), acetate, saline, physiological saline, phosphate buffer saline (PBS), 4-2-hydroxyethyl-1-piperazineethanesulfonic acid buffer (HEPES), 3-(N-morpholino)propanesulfonic acid buffer (MOPS), and piperazine-N,N'-bis(2-ethanesulfonic acid) buffer (PIPES), citric acid monohydrate, sodium dihydrogen phosphate, potassium dihydrogen phosphate, or any combination thereof.

In some embodiments, the pharmaceutical composition provided herein comprises an alcohol as an excipient. Non-limiting examples of alcohols include ethanol, propylene glycol, glycerol, polyethylene glycol, chlorobutanol, isopropanol, xylitol, sorbitol, maltitol, erythritol, threitol, arabitol, ribitol, mannitol, galactilol, fucitol, lactitol, or any combination thereof.

Pharmaceutical preparations can be formulated with polyethylene glycol (PEG). PEGs with molecular weights ranging from about 300 g/mol to about 10,000,000 g/mol can be used. Non-limiting examples of PEGs include PEG 200, PEG 300, PEG 400, PEG 540, PEG 550, PEG 600, PEG 1000, PEG 1450, PEG 1500, PEG 2000, PEG 3000, PEG 3350, PEG 4000, PEG 4600, PEG 6000, PEG 8000, PEG 10,000, and PEG 20,000.

Further excipients that can be used in a composition described herein include, for example, benzalkonium chloride, benzethonium chloride, benzyl alcohol, butylated hydroxyanisole, butylated hydroxytoluene, chlorobutanol, dehydroacetic acid, ethylenediamine, ethyl vanillin, glycerin, hypophosphorous acid, phenol, phenylethyl alcohol, phenylmercuric nitrate, potassium benzoate, potassium metabisulfite, potassium sorbate, sodium bisulfite, sodium metabisulfite, sorbic acid, thimerasol, acetic acid, aluminum monostearate, boric acid, calcium hydroxide, calcium stearate, calcium sulfate, calcium tetrachloride, cellulose acetate pthalate, microcrystalline celluose, chloroform, citric acid, edetic acid, and ethylcellulose.

In some embodiments, the pharmaceutical composition provided herein comprises an aprotic solvent as an excipient. Non-limiting examples of aprotic solvents include perfluorohexane, α,α,α-trifluorotoluene, pentane, hexane, cyclohexane, methylcyclohexane, decalin, dioxane, carbon tetrachloride, freon-11, benzene, toluene, carbon disulfide, diisopropyl ether, diethyl ether, t-butyl methyl ether, ethyl acetate, 1,2-dimethoxyethane, 2-methoxyethyl ether, tetrahydrofuran, methylene chloride, pyridine, 2-butanone, acetone, N-methylpyrrolidinone, nitromethane, dimethylformamide, acetonitrile, sulfolane, dimethyl sulfoxide, and propylene carbonate.

The amount of the excipient in a pharmaceutical composition described herein can be about 0.01%, about 0.02%, about 0.03%, about 0.04%, about 0.05%, about 0.06%, about 0.07%, about 0.08%, about 0.09%, about 0.1%, about 0.2%, about 0.3%, about 0.4%, about 0.5%, about 0.6%, about 0.7%, about 0.8%, about 0.9%, about 1%, about 1.5%, about 2%, about 2.5%, about 3%, about 3.5%, about 4%, about 4.5%, about 5%, about 6%, about 7%, about 8%, about 9%, about 10%, about 15%, about 20%, about 25%, about 30%, about 35%, about 40%, about 45%, about 50%, about 60%, about 70%, about 80%, about 90%, about 100%, about 200%, about 300%, about 400%, about 500%, about 600%, about 700%, about 800%, about 900%, or about 1000% by mass of a compound in the pharmaceutical formulation.

The amount of the excipient in a pharmaceutical composition described herein can be about 0.01%, about 0.02%, about 0.03%, about 0.04%, about 0.05%, about 0.06%, about 0.07%, about 0.08%, about 0.09%, about 0.1%, about 0.2%, about 0.3%, about 0.4%, about 0.5%, about 0.6%, about 0.7%, about 0.8%, about 0.9%, about 1%, about 1.5%, about 2%, about 2.5%, about 3%, about 3.5%, about 4%, about 4.5%, about 5%, about 6%, about 7%, about 8%, about 9%, about 10%, about 15%, about 20%, about 25%, about 30%, about 35%, about 40%, about 45%, about 50%, about 55% about 60%, about 65%, about 70%, about 75%, about 80%, about 85%, about 90%, about 95%, about 99%, or about 100% by mass or by volume of the unit dosage form.

In some embodiments, the addition of an excipient can change the viscosity of a pharmaceutical composition described herein. In some embodiments the use of an excipient can increase or decrease the viscosity of a fluid by at least 0.001 Pascal-second (Pa·s), at least 0.001 Pa·s, at least 0.0009 Pa·s, at least 0.0008 Pa·s, at least 0.0007 Pa·s, at least 0.0006 Pa·s, at least 0.0005 Pa·s, at least 0.0004 Pa·s, at least 0.0003 Pa·s, at least 0.0002 Pa·s, at least 0.0001 Pa·s, at least 0.00005 Pa·s, or at least 0.00001 Pa·s.

In some embodiments, the addition of an excipient to a pharmaceutical composition described herein can increase or decrease the viscosity of the composition by at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 99%. In some embodiments, the addition of an excipient to a pharmaceutical composition described herein can increase or decrease the viscosity of the composition by no greater than 5%, no greater than 10%, no greater than 15%, no greater than 20%, no greater than 25%, no greater than 30%, no greater than 35%, no greater than 40%, no greater than 45%, no greater than 50%, no greater than 55%, no greater than 60%, no greater than 65%, no greater than 70%, no greater than 75%, no greater than 80%, no greater than 85%, no greater than 90%, no greater than 95%, or no greater than 99%.

Purity.

A formulation or unit dosage form described herein can exhibit, for example, about 0.1%, about 0.2%, about 0.3%, about 0.4%, about 0.5%, about 0.6%, about 0.7%, about 0.8%, about 0.9% about 1%, about 1.1%, about 1.2%, about 1.3%, about 1.4%, about 1.5%, about 1.6%, about 1.7%, about 1.8%, about 1.9%, about 2%, about 2.1%, about 2.2%, about 2.3%, about 2.4%, about 2.5%, about 2.6%, about 2.7%, about 2.8%, about 2.9%, about 3%, about 3.1%, about 3.2%, about 3.3%, about 3.4%, about 3.5%, about 3.6%, about 3.7%, about 3.8%, about 3.9%, about 4%, about 4.1%, about 4.2%, about 4.3%, about 4.4%, about 4.5%, about 4.6%, about 4.7%, about 4.8%, about 4.9%, about 5%, about 5.5%, about 6%, about 6.5%, about 7%, about 7.5%, about 8%, about 8.5%, about 9%, about 9.5%, or about 10% degradation over a specified period of time. The degradation of a formulation or a unit dosage form disclosed herein can be assessed after about 24 hours, about 36 hours, about 72 hours, about 96 hours, about 1 week, about 2 weeks, about 3 weeks, about 4 weeks, about 5 weeks, about 6 weeks, about 2 months, about 3 months, about 4 months, about 5 months, about 6 months, about 8 months, about 10 months, about 1 year, about 13 months, about 14 months, about 15 months, about 16 months, about 17 months, about 18 months, about 19 months, about 20 months, about 21 months, about 22 months, about 23 months, about 2 years, about 25 months, about 26 months, about 27 months, about 28 months, about 29 months, about 30 months, about 31 months, about 32 months, about 33 months, about 34 months, about 35 months, or about 3 years of storage. The degradation of a formulation or a unit dosage form disclosed herein can be assessed at a temperature of, for example, about 0° C., about 1° C., about 2° C., about 3° C., about 4° C., about 5° C., about 6° C., about 7° C., about 8° C., about 9° C., about 10° C., about 11° C., about 12° C., about 13° C., about 14° C., about 15° C., about 16° C., about 17° C., about 18° C., about 19° C., about 20° C., about 21° C., about 22° C., about 23° C., about 24° C., about 25° C., about 26° C., about 27° C., about 28° C., about 29° C., about 30° C., about 31° C., about 32° C., about 33° C., about 34° C., about 35° C., about 36° C., about 37° C., about 38° C., about 39° C., about 40° C., about 41° C., about 42° C., about 43° C., about 44° C., about 45° C., about 46° C., about 47° C., about 48° C., about 49° C., about 50° C., about 55° C., about 60° C., or about 0° C. to about 5° C., about 1° C. to about 6° C., about 2° C. to about 7° C., about 2° C. to about 8° C., about 3° C. to about 8° C., about 4° C. to about 9° C., about 5° C. to about 10° C., about 6° C. to about 11° C., about 7° C. to about 12° C., about 8° C. to about 13° C., about 9° C. to about 14° C., about 10° C. to about 15° C., about 11° C. to about 16° C., about 12° C. to about 17° C., about 13° C. to about 18° C., about 14° C. to about 19° C., about 15° C. to about 20° C., about 16° C. to about 21° C., about 17° C. to about 22° C., about 18° C. to about 23° C., about 19° C. to about 24° C., about 20° C. to about 25° C., about 21° C. to about 26° C., about 22° C. to about 27° C., about 23° C. to about 28° C., about 24° C. to about 29° C., about 25° C. to about 30° C., about 26° C. to about 31° C., about 27° C. to about 32° C., about 28° C. to about 33° C., about 29° C. to about 34° C., about 30° C. to about 35° C., about 31° C. to about 36° C., about 32° C. to about 37° C., about 33° C. to about 38° C., about 34° C. to about 39° C., about 35° C. to about 40° C., about 36° C. to about 41° C., about 37° C. to about 42° C., about 38° C. to about 43° C., about 39° C. to about 44° C., about 40° C. to about 45° C., about 41° C. to about 46° C., about 42° C. to about 47° C., about 43° C. to about 48° C., about 44° C. to about 49° C., about 45° C. to about 50° C., or about 55° C. to about 60° C.

The purity of a pharmaceutical formulation described herein can be determined by analyzing the amount of active ingredient remaining over a specific time period at a specific temperature, when formulated, for example, at a specific pH. Additionally, the purity of the pharmaceutical formulation can be assessed by determining the amount of impurities present in the pharmaceutical formulation over a specific time period at a specific temperature, when formulated, for example, at a specific pH. The amount of active ingredient and impurities can be determined by, for example, HPLC.

Any compound herein can be purified. A compound can be at least 1% pure, at least 2% pure, at least 3% pure, at least 4% pure, at least 5% pure, at least 6% pure, at least 7% pure, at least 8% pure, at least 9% pure, at least 10% pure, at least 11% pure, at least 12% pure, at least 13% pure, at least 14% pure, at least 15% pure, at least 16% pure, at least 17% pure, at least 18% pure, at least 19% pure, at least 20% pure, at least 21% pure, at least 22% pure, at least 23% pure, at least 24% pure, at least 25% pure, at least 26% pure, at least 27% pure, at least 28% pure, at least 29% pure, at least 30% pure, at least 31% pure, at least 32% pure, at least 33% pure, at least 34% pure, at least 35% pure, at least 36% pure, at least 37% pure, at least 38% pure, at least 39% pure, at least 40% pure, at least 41% pure, at least 42% pure, at least 43% pure, at least 44% pure, at least 45% pure, at least 46% pure, at least 47% pure, at least 48% pure, at least 49% pure, at least 50% pure, at least 51% pure, at least 52% pure, at least 53% pure, at least 54% pure, at least 55% pure, at least 56% pure, at least 57% pure, at least 58% pure, at least 59% pure, at least 60% pure, at least 61% pure, at least 62% pure, at least 63% pure, at least 64% pure, at least 65% pure, at least 66% pure, at least 67% pure, at least 68% pure, at least 69% pure, at least 70% pure, at least 71% pure, at least 72% pure, at least 73% pure, at least 74% pure, at least 75% pure, at least 76% pure, at least 77% pure, at least 78% pure, at least 79% pure, at least 80% pure, at least 81% pure, at least 82% pure, at least 83% pure, at least 84% pure, at least 85% pure, at least 86% pure, at least 87% pure, at least 88% pure, at least 89% pure, at least 90% pure, at least 91% pure, at least 92% pure, at least 93% pure, at least 94% pure, at least 95% pure, at least 96% pure, at least 97% pure, at least 98% pure, at least 99% pure, at least 99.1% pure, at least 99.2% pure, at least 99.3% pure, at least 99.4% pure, at least 99.5% pure, at least 99.6% pure, at least 99.7% pure, at least 99.8% pure, or at least 99.9% pure.

The amount of impurity in a composition described herein can be, for example, about 0.01%, about 0.02%, about 0.03%, about 0.04%, about 0.05%, about 0.06%, about 0.07%, about 0.08%, about 0.09%, about 0.1%, about 0.2%, about 0.3%, about 0.4%, about 0.5%, about 0.6%, about 0.7%, about 0.8%, about 0.9%, about 1%, about 1.1%, about 1.2%, about 1.3%, about 1.4%, about 1.5%, about 1.6%, about 1.7%, about 1.8%, about 1.9%, about 2%, about 2.1%, about 2.2%, about 2.3%, about 2.4%, about 2.5%, about 2.6%, about 2.7%, about 2.8%, about 2.9%, about 3%, about 3.1%, about 3.2%, about 3.3%, about 3.4%, about 3.5%, about 3.6%, about 3.7%, about 3.8%, about 3.9%, about 4%, about 4.1%, about 4.2%, about 4.3%, about 4.4%, about 4.5%, about 4.6%, about 4.7%, about 4.8%, about 4.9%, about 5%, about 5.5%, about 6%, about 6.5%, about 7%, about 7.5%, about 8%, about 8.5%, about 9%, about 9.5%, about 10%, about 11%, about 12%, about 13%, about 14%, about 15%, about 16%, about 17%, about 18%, about 19%, about 20%, about 25%, about 30%, about 35%, about 40%, about 45%, about 50%, about 55%, about 60%, about 65%, about 70%, about 75%, about 80%, about 85%, about 90%, about 95%, or about 100% by mass of a compound present in the composition.

The amount of degradation of one or both of the non-opioid analgesics present in a formulation described herein can be maintained to be below about 10%, about 5%, or about 2% when the formulation is stored as a liquid formulation for over at least about one week, at least about two weeks, at least about three weeks, or at least about one month at a temperature of less than about 60° C.

The impurities in a pharmaceutical formulation described herein can include, for example, 4-aminophenol (para-aminophenol), 4-(2-methylpropyl)pyrrolidin-2-one (MPP; pregabalin lactam), or any unknown impurity.

Non-limiting examples of methods that can be used to identify impurities and the amount of active ingredient in a formulation described herein include HPLC, reversed-phase HPLC (RP-HPLC), mass spectrometry (MS), Matrix Assisted Laser Desorption Ionization Time-of-Flight (MALDI-TOF), electrospray ionization Time-of-flight (ESI-TOF), gas chromatography-mass spectrometry (GC-MS), liquid chromatography-mass spectrometry (LC-MS), and two-dimensional gel electrophoresis.

HPLC can be used to identify impurities using high pressure to separate components of a mixture through a packed column of solid adsorbent material, denoted the stationary phase. The sample components can interact differently with the column based upon the pressure applied to the column, material used in stationary phase, size of particles used in the stationary phase, the composition of the solvent used in the column, and the temperature of the column. The interaction between the sample components and the stationary phase can affect the time required for a component of the sample to move through the column. The time required for component to travel through the column from injection point to elution is known as the retention time.

Upon elution from the column, the eluted component can be detected using a UV detector attached to the column. The wavelength of light at which the component is detected, in combination with the component's retention time, can be used to identify the component. Further, the peak displayed by the detector can be used to determine the quantity of the component present in the initial sample. Wavelengths of light that can be used to detect sample components include, for example, about 200 nM, about 225 nm, about 250 nm, about 275 nm, about 300 nm, about 325 nm, about 350 nm, about 375 nm, and about 400 nm.

Mass spectrometry (MS) can also be used to identify impurities in a formulation described herein. The samples can be injected into a mass spectrometer. Upon injection, the sample can be ionized and detected as ions on a spectrum according to the mass to charge ratio created upon ionization. The mass to charge ratio can then be used to determine the impurities present in the sample.

Pharmacokinetics and Pharmacodynamics.

A dose can be modulated to achieve a desired pharmacokinetic or pharmacodynamics profile, such as a desired or effective blood profile, as described herein.

Pharmacokinetic and pharmacodynamic data can be obtained by various experimental techniques. Appropriate pharmacokinetic and pharmacodynamic profile components describing a particular composition can vary due to variations in drug metabolism in human subjects. Pharmacokinetic and pharmacodynamic profiles can be based on the determination of the mean parameters of a group of subjects. The group of subjects includes any reasonable number of subjects suitable for determining a representative mean, for example, 5 subjects, 10 subjects, 15 subjects, 20 subjects, 25 subjects, 30 subjects, 35 subjects, or more. The mean is determined, for example, by calculating the average of all subject's measurements for each parameter measured. A dose can be modulated to achieve a desired pharmacokinetic or pharmacodynamics profile, such as a desired or effective blood profile, as described herein.

The pharmacodynamic parameters can be any parameters suitable for describing compositions described herein. For example, the pharmacodynamic profile can be obtained at a time after dosing of, for example, about zero minutes, about 1 minute, about 2 minutes, about 3 minutes, about 4 minutes, about 5 minutes, about 6 minutes, about 7 minutes, about 8 minutes, about 9 minutes, about 10 minutes, about 11 minutes, about 12 minutes, about 13 minutes, about 14 minutes, about 15 minutes, about 16 minutes, about 17 minutes, about 18 minutes, about 19 minutes, about 20 minutes, about 21 minutes, about 22 minutes, about 23 minutes, about 24 minutes, about 25 minutes, about 26 minutes, about 27 minutes, about 28 minutes, about 29 minutes, about 30 minutes, about 31 minutes, about 32 minutes, about 33 minutes, about 34 minutes, about 35 minutes, about 36 minutes, about 37 minutes, about 38 minutes, about 39 minutes, about 40 minutes, about 41 minutes, about 42 minutes, about 43 minutes, about 44 minutes, about 45 minutes, about 46 minutes, about 47 minutes, about 48 minutes, about 49 minutes, about 50 minutes, about 51 minutes, about 52 minutes, about 53 minutes, about 54 minutes, about 55 minutes, about 56 minutes, about 57 minutes, about 58 minutes, about 59 minutes, about 60 minutes, about zero hours, about 0.5 hours, about 1 hour, about 1.5 hours, about 2 hours, about 2.5 hours, about 3 hours, about 3.5 hours, about 4 hours, about 4.5 hours, about 5 hours, about 5.5 hours, about 6 hours, about 6.5 hours, about 7 hours, about 7.5 hours, about 8 hours, about 8.5 hours, about 9 hours, about 9.5 hours, about 10 hours, about 10.5 hours, about 11 hours, about 11.5 hours, about 12 hours, about 12.5 hours, about 13 hours, about 13.5 hours, about 14 hours, about 14.5 hours, about 15 hours, about 15.5 hours, about 16 hours, about 16.5 hours, about 17 hours, about 17.5 hours, about 18 hours, about 18.5 hours, about 19 hours, about 19.5 hours, about 20 hours, about 20.5 hours, about 21 hours, about 21.5 hours, about 22 hours, about 22.5 hours, about 23 hours, about 23.5 hours, or about 24 hours.

The pharmacokinetic parameters can be any parameters suitable for describing a compound disclosed herein. The $C_{max}$ can be, for example, not less than about 1 ng/mL; not less than about 5 ng/mL; not less than about 10 ng/mL; not less than about 15 ng/mL; not less than about 20 ng/mL; not less than about 25 ng/mL; not less than about 50 ng/mL; not less than about 75 ng/mL; not less than about 100 ng/mL; not less than about 200 ng/mL; not less than about 300 ng/mL; not less than about 400 ng/mL; not less than about 500 ng/mL; not less than about 600 ng/mL; not less than about 700 ng/mL; not less than about 800 ng/mL; not less than about 900 ng/mL; not less than about 1000 ng/mL; not less than about 1250 ng/mL; not less than about 1500 ng/mL; not less than about 1750 ng/mL; not less than about 2000 ng/mL; not less than about 5000 mg/mL; not less than about 10,000 ng/mL; not less than about 15,000 ng/mL; not less than about 20,000 ng/mL; not less than about 30,000 ng/mL; not less than about 40,000 n g/mL; or any other $C_{max}$ appropriate for describing a pharmacokinetic profile of a compound described herein. The $C_{max}$ can be, for example, about 1 ng/mL to about 5,000 ng/mL; about 1 ng/mL to about 4,500 ng/mL; about 1 ng/mL to about 4,000 ng/mL; about 1 ng/mL to about 3,500 ng/mL; about 1 ng/mL to about 3,000 ng/mL; about 1 ng/mL to about 2,500 ng/mL; about 1 ng/mL to about 2,000 ng/mL; about 1 ng/mL to about 1,500 ng/mL; about 1 ng/mL to about 1,000 ng/mL; about 1 ng/mL to about 900 ng/mL; about 1 ng/mL to about 800 ng/mL; about 1 ng/mL to about 700 ng/mL; about 1 ng/mL to about 600 ng/mL; about 1 ng/mL to about 500 ng/mL; about 1 ng/mL to about 450 ng/mL; about 1 ng/mL to about 400 ng/mL; about 1 ng/mL to about 350 ng/mL; about 1 ng/mL to about 300 ng/mL; about 1 ng/mL to about 250 ng/mL; about 1 ng/mL to about 200 ng/mL; about 1 ng/mL to about 150 ng/mL; about 1 ng/mL to about 125 ng/mL; about 1 ng/mL to about 100 ng/mL; about 1 ng/mL to about 90 ng/mL; about 1 ng/mL to about 80 ng/mL; about 1 ng/mL to about 70 ng/mL; about 1 ng/mL to about 60 ng/mL; about 1 ng/mL to about 50 ng/mL; about 1 ng/mL to about 40 ng/mL; about 1 ng/mL to about 30 ng/mL; about 1 ng/mL to about 20 ng/mL; about 1 ng/mL to about 10 ng/mL; about 1 ng/mL to about 5 ng/mL; about 10 ng/mL to about 4,000 ng/mL; about 10 ng/mL to about 3,000 ng/mL; about 10 ng/mL to about 2,000 ng/mL; about 10 ng/mL to about 1,500 ng/mL; about 10 ng/mL to about 1,000 ng/mL; about 10 ng/mL to about 900 ng/mL; about 10 ng/mL to about 800 ng/mL; about 10 ng/mL to about 700 ng/mL; about 10 ng/mL to about 600 ng/mL; about 10 ng/mL to about 500 ng/mL; about 10 ng/mL to about 400 ng/mL; about 10 ng/mL to about 300 ng/mL; about 10 ng/mL to about 200 ng/mL; about 10 ng/mL to about 100 ng/mL; about 10 ng/mL to about 50 ng/mL; about 25 ng/mL to about 500 ng/mL; about 25 ng/mL to about 100 ng/mL; about 50 ng/mL to about 500 ng/mL; about 50 ng/mL to about 100 ng/mL; about 100 ng/mL to about 500 ng/mL; about 100 ng/mL to about 400 ng/mL; about 100 ng/mL to about 300 ng/mL; or about 100 ng/mL to about 200 ng/mL.

The $T_{max}$ of a compound described herein can be, for example, not greater than about 0.5 hours, not greater than about 1 hours, not greater than about 1.5 hours, not greater than about 2 hours, not greater than about 2.5 hours, not greater than about 3 hours, not greater than about 3.5 hours, not greater than about 4 hours, not greater than about 4.5 hours, not greater than about 5 hours, or any other $T_{max}$ appropriate for describing a pharmacokinetic profile of a compound described herein. The $T_{max}$ can be, for example, about 0.1 hours to about 24 hours; about 0.1 hours to about 0.5 hours; about 0.5 hours to about 1 hour; about 1 hour to about 1.5 hours; about 1.5 hours to about 2 hour; about 2 hours to about 2.5 hours; about 2.5 hours to about 3 hours; about 3 hours to about 3.5 hours; about 3.5 hours to about 4 hours; about 4 hours to about 4.5 hours; about 4.5 hours to about 5 hours; about 5 hours to about 5.5 hours; about 5.5 hours to about 6 hours; about 6 hours to about 6.5 hours; about 6.5 hours to about 7 hours; about 7 hours to about 7.5 hours; about 7.5 hours to about 8 hours; about 8 hours to about 8.5 hours; about 8.5 hours to about 9 hours; about 9 hours to about 9.5 hours; about 9.5 hours to about 10 hours; about 10 hours to about 10.5 hours; about 10.5 hours to about 11 hours; about 11 hours to about 11.5 hours; about 11.5 hours to about 12 hours; about 12 hours to about 12.5 hours; about 12.5 hours to about 13 hours; about 13 hours to about 13.5 hours; about 13.5 hours to about 14 hours; about 14 hours to about 14.5 hours; about 14.5 hours to about 15 hours; about 15 hours to about 15.5 hours; about 15.5 hours to about 16 hours; about 16 hours to about 16.5 hours; about 16.5 hours to about 17 hours; about 17 hours to about 17.5 hours; about 17.5 hours to about 18 hours; about 18 hours to about 18.5 hours; about 18.5 hours to about 19 hours; about 19 hours to about 19.5 hours; about 19.5 hours to about 20 hours; about 20 hours to about 20.5 hours; about 20.5 hours to about 21 hours; about 21 hours to about 21.5 hours; about 21.5 hours to about 22 hours; about 22 hours to about 22.5 hours; about 22.5 hours to about 23 hours; about 23 hours to about 23.5 hours; or about 23.5 hours to about 24 hours.

The $AUC_{(0-inf)}$ or $AUC_{(last)}$ of a compound described herein can be, for example, not less than about 1 ng·hr/mL, not less than about 5 ng·hr/mL, not less than about 10 ng·hr/mL, not less than about 20 ng·hr/mL, not less than about 30 ng·hr/mL, not less than about 40 ng·hr/mL, not less than about 50 ng·hr/mL, not less than about 100 ng·hr/mL, not less than about 150 ng·hr/mL, not less than about 200 ng·hr/mL, not less than about 250 ng·hr/mL, not less than about 300 ng·hr/mL, not less than about 350 ng·hr/mL, not less than about 400 ng·hr/mL, not less than about 450 ng·hr/mL, not less than about 500 ng·hr/mL, not less than about 600 ng·hr/mL, not less than about 700 ng·hr/mL, not less than about 800 ng·hr/mL, not less than about 900 ng·hr/mL, not less than about 1000 ng·hr/mL, not less than about 1250 ng·hr/mL, not less than about 1500 ng·hr/mL, not less than about 1750 ng·hr/mL, not less than about 2000 ng·hr/mL, not less than about 2500 ng·hr/mL, not less than about 3000 ng·hr/mL, not less than about 3500 ng·hr/mL, not less than about 4000 ng·hr/mL, not less than about 5000 ng·hr/mL, not less than about 6000 ng·hr/mL, not less than about 7000 ng·hr/mL, not less than about 8000 ng·hr/mL, not less than about 9000 ng·hr/mL, not less than about 10,000 ng·hr/mL, not less than about 15,000 ng·hr/mL, not less than about 20,000 ng·hr/mL, not less than about 25,000 ng·hr/mL, not less than about 30,000 ng·hr/mL, not less than about 40,000 ng·hr/mL, not less than about 50,000 ng·hr/mL, or any other $AUC_{(0-inf)}$ appropriate for describing a pharmacokinetic profile of a compound described herein. The $AUC_{(0-inf)}$ of a compound can be, for example, about 1 ng·hr/mL to about 10,000 ng·hr/mL; about 1 ng·hr/mL to about 10 ng·hr/mL; about 10 ng·hr/mL to about 25 ng·hr/mL; about 25 ng·hr/mL to about 50 ng·hr/mL; about 50 ng·hr/mL to about 100 ng·hr/mL; about 100 ng·hr/mL to about 200 ng·hr/mL; about 200 ng·hr/mL to about 300 ng·hr/mL; about 300 ng·hr/mL to about 400 ng·hr/mL; about 400 ng·hr/mL to about 500 ng·hr/mL; about 500 ng·hr/mL to about 600 ng·hr/mL; about 600 ng·hr/mL to about 700 ng·hr/mL; about 700 ng·hr/mL to about 800 ng·hr/mL; about 800 ng·hr/mL to about 900 ng·hr/mL; about 900 ng·hr/mL to about 1,000 ng·hr/mL; about 1,000 ng·hr/mL to about 1,250 ng·hr/mL; about 1,250 ng·hr/mL to about 1,500 ng·hr/mL; about 1,500 ng·hr/mL to about 1,750 ng·hr/mL; about 1,750 ng·hr/mL to about 2,000 ng·hr/mL; about 2,000 ng·hr/mL to about 2,500 ng·hr/mL; about 2,500 ng·hr/mL to about 3,000 ng·hr/mL; about 3,000 ng·hr/mL to about 3,500 ng·hr/mL; about 3,500 ng·hr/mL to about 4,000 ng·hr/mL; about 4,000 ng·hr/mL to about 4,500 ng·hr/mL; about 4,500 ng·hr/mL to about 5,000 ng·hr/mL; about 5,000 ng·hr/mL to about 5,500 ng·hr/mL; about 5,500 ng·hr/mL to about 6,000 ng·hr/mL; about 6,000 ng·hr/mL to about 6,500 ng·hr/mL; about 6,500 ng·hr/mL to about 7,000 ng·hr/mL; about 7,000 ng·hr/mL to about 7,500 ng·hr/mL; about 7,500 ng·hr/mL to about 8,000 ng·hr/mL; about 8,000 ng·hr/mL to about 8,500 ng·hr/mL; about 8,500 ng·hr/mL to about 9,000 ng·hr/mL; about 9,000 ng·hr/mL to about 9,500 ng·hr/mL; or about 9,500 ng·hr/mL to about 10,000 ng·hr/mL.

The plasma concentration of a compound described herein can be, for example, not less than about 1 ng/mL, not less than about 5 ng/mL, not less than about 10 ng/mL, not less than about 15 ng/mL, not less than about 20 ng/mL, not less than about 25 ng/mL, not less than about 50 ng/mL, not less than about 75 ng/mL, not less than about 100 ng/mL, not less than about 150 ng/mL, not less than about 200 ng/mL, not less than about 300 ng/mL, not less than about 400 ng/mL, not less than about 500 ng/mL, not less than about 600 ng/mL, not less than about 700 ng/mL, not less than about 800 ng/mL, not less than about 900 ng/mL, not less than about 1000 ng/mL, not less than about 1200 ng/mL, or any other plasma concentration of a compound described herein. The plasma concentration can be, for example, 1 ng/mL to about 2,000 ng/mL; about 1 ng/mL to about 5 ng/mL; about 5 ng/mL to about 10 ng/mL; about 10 ng/mL to about 25 ng/mL; about 25 ng/mL to about 50 ng/mL; about 50 ng/mL to about 75 ng/mL; about 75 ng/mL to about 100 ng/mL; about 100 ng/mL to about 150 ng/mL; about 150 ng/mL to about 200 ng/mL; about 200 ng/mL to about 250 ng/mL; about 250 ng/mL to about 300 ng/mL; about 300 ng/mL to about 350 ng/mL; about 350 ng/mL to about 400 ng/mL; about 400 ng/mL to about 450 ng/mL; about 450 ng/mL to about 500 ng/mL; about 500 ng/mL to about 600 ng/mL; about 600 ng/mL to about 700 ng/mL; about 700 ng/mL to about 800 ng/mL; about 800 ng/mL to about 900 ng/mL; about 900 ng/mL to about 1,000 ng/mL; about 1,000 ng/mL to about 1,100 ng/mL; about 1,100 ng/mL to about 1,200 ng/mL; about 1,200 ng/mL to about 1,300 ng/mL; about 1,300 ng/mL to about 1,400 ng/mL; about 1,400 ng/mL to about 1,500 ng/mL; about 1,500 ng/mL to about 1,600 ng/mL; about 1,600 ng/mL to about 1,700 ng/mL; about 1,700 ng/mL to about 1,800 ng/mL; about 1,800 ng/mL to about 1,900 ng/mL; or about 1,900 ng/mL to about 2,000 ng/mL.

The pharmacodynamic parameters can be any parameters suitable for describing compositions of the disclosure. For example, the pharmacodynamic profile can demonstrate an increased pain tolerance in a subject who has been administered a pharmaceutical formulation described herein.

Non-limiting examples of pharmacodynamic and pharmacokinetic parameters that can be calculated for a compound that is administered with the methods described herein include: a) the amount of drug administered, which can be represented as a dose D; b) the dosing interval, which can be represented as $\tau$; c) the apparent volume in which a drug is distributed, which can be represented as a volume of distribution $V_d$, where $V_d=D/C_0$; d) the amount of drug in a given volume of plasma, which can be represented as concentration $C_0$ or $C_{ss}$, where $C_0$ or $C_{ss}=D/Vd$ and can be represented as a mean plasma concentration over a plurality of samples; e) the half-life of a drug $t_{1/2}$, where $t_{1/2}=\ln(2)/k_e$; f) the rate at which a drug is removed from the body $k_e$, where $k_e=\ln(2)/t_{1/2}=CL/V_d$; g) the rate of infusion required to balance the equation $K_{in}$, where $K_{in}=C_{ss}$, CL; h) the integral of the concentration-time curve after administration of a single dose, which can be represented as $AUC_{0-\infty}$, wherein $\int_0^\infty C\,dt$, or in steady-state, which can be represented as $AUC\tau_{ss}$, wherein $\int_t^{t+\tau} C\,dt$; i) the volume of plasma cleared of the drug per unit time, which can be represented as CL (clearance), wherein $CL=V_d k_e=D/AUC$; j) the systemically available fraction of a drug, which can be represented as f, where $$f = \frac{AUCpo.Div}{AUCiv.Dpo}; k)$$

the peak plasma concentration of a drug after administration $C_{max}$; l) the time taken by a drug to reach $C_{max}$, $t_{max}$; m) the lowest concentration that a drug reaches before the next dose is administered $C_{max}$; and n) the peak trough fluctuation within one dosing interval at steady state, which can be represented as % PTF=100.

$$\frac{(Cmax, ss - Cmin, ss)}{Cav, ss}$$

where $$C_{av,ss} = \frac{AUC\tau, ss}{\tau}.$$

When administered via intravenous injection, a pharmaceutical composition described herein can exert an effect at a level of at least about 50%, at least about 70%, at least about 80%, or at least about 90% within less than about, for example, one hour or two hours of the administration. A pharmaceutical composition described herein can remain effective at a level of at least about 50%, at least about 70%, at least about 80%, or at least about 90% for at least about 1 hour, at least about 2 hours, at least about 3 hours, or at least about 6 hours after the administration.

A pharmaceutical formulation described herein can be administered to a subject about 1 minute, about 2 minutes, about 3 minutes, about 4 minutes, about 5 minutes, about 6 minutes, about 7 minutes, about 8 minutes, about 9 minutes, about 10 minutes, about 11 minutes, about 12 minutes, about 13 minutes, about 14 minutes, about 15 minutes, about 16 minutes, about 17 minutes, about 18 minutes, about 19 minutes, about 20 minutes, about 25 minutes, about 30 minutes, about 35 minutes, about 40 minutes, about 45 minutes, about 50 minutes, about 55 minutes, about 1 hour, about 1.5 hours, about 2 hours, about 2.5 hours, about 3 hours, about 3.5 hours, about 4 hours, about 4.5 hours, about 5 hours, about 5.5 hours, about 6 hours, about 6.5 hours, about 7 hours, about 7.5 hours, about 8 hours, about 8.5 hours, about 9 hours, about 9.5 hours, about 10 hours, about 10.5 hours, about 11 hours, about 11.5 hours, about 12 hours, about 18 hours, about 24 hours, about 30 hours, about 36 hours, about 42 hours, or about 48 hours prior to, or after, surgery. A pharmaceutical formulation described herein can be administered to a patient at the same time as when the surgery begins. A pharmaceutical formulation described herein can be administered to a patient during a surgery. A pharmaceutical formulation described herein can be administered to a patient right after a surgery is ended. A pharmaceutical formulation described herein can be administered one or more times prior to, during, or after, surgery for a patient. For example, a pharmaceutical formulation described herein can be administered to a patient one time a day, two times a day, three times a day, four times a day, five times a day, six times a day, seven times a day, eight times a day, nine times a day, or ten times a day. A pharmaceutical formulation described herein can be administered to a patient every 1 hours, every 2 hours, every 3 hours, every 4 hours, every 5 hours, every 6 hours, every 7 hours, every 8 hours, every 9 hours, every 10 hours, every 11 hours, or every 12 hours.

The present disclosure provides several embodiments of pharmaceutical formulations that provide advantages in stability, administration, efficacy, and modulation of formulation viscosity. Any embodiments disclosed herein can be used in conjunction or individually. For example, any pharmaceutically-acceptable excipient, method, technique, solvent, or compound disclosed herein can be used together with any other pharmaceutically-acceptable excipient, method, technique, solvent, or compound disclosed herein to achieve any therapeutic result. Compounds, excipients, and other formulation components can be present at any amount, ratio, or percentage disclosed herein in any such formulation, and any such combination can be used therapeutically for any purpose described herein and to provide any viscosity described herein.

Experimental Methods Used Herein.

Rotarod/Accelerod Test: The rotarod/accelerod test can be used to assess neuromuscular coordination and motor function in rodents. An animal is placed on an apparatus consisting of a horizontally-oriented circular rod, usually with a ridged surface to enhance grip. The rod is then rotated about the long axis, with the speed of rotation remaining constant (rotarod) or increasing over time (accelerod). The animal attempts to remain on the rotating rod, and the latency to fall is recorded.

The rotarod/accelerod test can be used to screen drugs or drug combinations for effects on motor function or neuromuscular coordination. Baseline results can be compared to results after treatment, or a control group can be compared to a treatment group. Decreased latency to fall is considered evidence of impaired neuromuscular coordination or motor function, and this can be observed in animal models of neurodegeneration and central nervous system injury. Benzodiazepines such as diazepam can impair performance in the rotarod/accelerod test and can serve as positive controls.

Hot Plate Test: The hot plate test is a test that can be used to assess pain sensitivity in rodents. The test is based on the principle that rodents placed on a hot surface can demonstrate aversion to the noxious stimulus by paw licking and/or jumping. In the test, an animal is placed in a confined cylindrical space to restrict locomotion. The floor surface of the space is maintained at a temperature sufficiently hot to elicit an aversive response, but not so hot that tissue damage is induced, typically 50-56° C. The animal is monitored, and latency to paw licking or jumping is recorded. This test can be used to screen novel drugs or drug combinations for effects on pain detection threshold; substances with an analgesic effect can increase latency to licking/jumping, while substances with a hyperalgesic effect can decrease latency.

In Vitro Hemolysis Test: The in vitro hemolysis test can be used to determine whether a treatment of interest exhibits erythrocyte (red blood cell)-lysing activity. Drug candidates can be tested to assess the potential of the active compound, metabolites thereof, or excipients in the formulation to cause toxic hemolysis, which in vivo can result in neutropenia, thrombocytopenia, hemolytic anemia, aplastic anemia, or macrocytic anemia.

The compound of interest is serially-diluted and applied to erythrocytes suspended in either plasma or isotonic buffer. As a positive control, erythrocytes are treated with a known hemolytic agent (for example, sodium dodecyl sulfate), and as a negative control erythrocytes are treated with a vehicle lacking the test compound (for example, dimethyl sulfoxide). The samples are then incubated at 37° C., centrifuged to remove intact cells and large particulate matter, and the supernatant absorbance measured via spectrophotometry. The absorbance can increase proportionally with hemolysis due to the presence of hemoglobin in the supernatant. Percent hemolysis in each sample can then be calculated using a formula similar to:

$$\text{percent hemolysis} = 100 \times \frac{(\text{absorbance of sample} - \text{absorbance of negative control})}{(\text{absorbance of positive control} - \text{absorbance of negative control})}.$$

EXAMPLES

Example 1: The Effect of pH on the Solubility of Pregabalin and Acetaminophen

The solubility of pregabalin (PGB) and acetaminophen (APAP) was determined at room temperature in water at different pH values. The samples were prepared by adding acetaminophen in water at a concentration of 50 mg/mL, and pregabalin at a concentration of 100 mg/mL. The pH was then adjusted to the required range. The concentration of the active ingredients was determined by HPLC-UV.

As can be seen from TABLE 1, no significant difference in the solubility of acetaminophen was observed in the pH range from 4-7.

The solubility of pregabalin was higher at pH 4 and was found to be about 31 mg/mL at the pH range of 5-7, as shown in TABLE 2.

TABLE 1

| Sample | Acetaminophen (mg/mL) |
| --- | --- |
| pH 4 | 13.8 |
| pH 5 | 13.9 |
| pH 6 | 13.8 |
| pH 7 | 13.9 |

TABLE 2

| Sample | Pregabalin (mg/mL) |
|---|---|
| pH 4 | 54.4 |
| pH 5 | 32.4 |
| pH 6 | 31.0 |
| pH 7 | 30.6 |

The concentration of pregabalin and acetaminophen in an aqueous carrier can be increased when the pregabalin and acetaminophen are co-dissolved in the aqueous carrier. Solubility samples were prepared by adding acetaminophen and pregabalin in water at 50 mg/mL and 100 mg/mL concentration, respectively, and adjusting the pH to the required range.

As can be seen from TABLE 3, the solubility of acetaminophen was increased to about 21 mg/mL in presence of pregabalin, which was more than 1.5 times the solubility obtained for acetaminophen alone at pH 4. Also, the increase in the solubility of pregabalin in the presence of acetaminophen was observed within the pH range of 5-7 in comparison to solubility values obtained in the same pH range for pregabalin alone.

TABLE 3

| Sample | Acetaminophen (mg/mL) | Pregabalin (mg/mL) |
|---|---|---|
| pH 4 | 20.8 | 54.4 |
| pH 5 | 18.7 | 36.8 |
| pH 6 | 17.9 | 35.0 |
| pH 7 | 17.9 | 35.0 |

Example 2: Stability of Acetaminophen and Pregabalin Formulations

To determine the stability of acetaminophen and pregabalin co-formulations, citrate buffer (10 mM), acetate buffer (10 mM), and phosphate buffer (10 mM) were disposed in four separate manufacturing tanks as shown in TABLE 4. Pregabalin, acetaminophen, and other excipients were added to each of the tanks, and filled with the required quantities of water (water for injection) to obtain a concentration of 4.5 and 10 mg/mL, respectively.

Then, the pH of each of the tanks was readjusted using HCl or NaOH. The volume of the tanks can be made up with deoxygenated water.

The bulk solutions were filled into 100 mL polypropylene bags with a target fill volume of 100 mL and were then stoppered and sealed. The bags were then further packaged in aluminum bags along with an oxygen scavenger, and were sealed.

The samples were tested for assay and impurities. TABLE 4 shows the four different formulations of pregabalin and acetaminophen in two different buffers in two different pH conditions, respectively.

TABLE 4

| Composition (mg/mL) | I Citrate Buffer (pH 5.5) mg/mL | J Citrate Buffer (pH 6) mg/mL | K Acetate Buffer (pH 5.5) mg/mL | L Phosphate Buffer (pH 6) mg/mL |
|---|---|---|---|---|
| Acetaminophen | 10 | 10 | 10 | 10 |
| Pregabalin | 4.5 | 4.5 | 4.5 | 4.5 |
| Sodium Chloride | 5 | 4.5 | 5 | 5.5 |
| Citric Acid Monohydrate | 2.101 | 2.101 | — | — |
| Acetic Acid | — | — | 0.6 | — |
| Sodium Dihydrogen Phosphate | — | — | — | 1.2 |
| HCl/NaOH 5N | q.s. 5.5 | q.s. 6 | q.s. 5.5 | q.s. 6 |
| Water for Injection (WFI) | q.s 1 mL | q.s 1 mL | q.s 1 mL | q.s 1 mL |

TABLES 5 and 6 provide assay values of pregabalin or acetaminophen, reflecting the remaining effectiveness of the pregabalin or acetaminophen in each solution described in TABLE 4.

In each tested solution, assay values of pregabalin or acetaminophen remained at least 98% or above after 2 weeks at 60° C. or after a month at 40° C. or 25° C.

TABLE 5

| | PREGABALIN Assay | | | | |
|---|---|---|---|---|---|
| | 60° C. | | | 40° C. | 25° C. |
| Buffers | T0 | 1 Week | 2 Week | 1 Month | 1 Month |
| Citrate Buffer pH 5.5 | 99.9 | 99 | 98.8 | 100.9 | 100.1 |
| Citrate Buffer pH 6 | 100.6 | 99.8 | 104.1 | 101.3 | 101 |
| Acetate Buffer pH 5.5 | 101 | 97.7 | 102.1 | 100.8 | 101.1 |
| Phosphate Buffer pH 6 | 99 | 99.9 | 101.4 | 101.9 | 100 |

TABLE 6

| | ACETAMINOPHEN Assay | | | | |
|---|---|---|---|---|---|
| | 60° C. | | | 40° C. | 25° C. |
| Buffers | T0 | 1 Week | 2 Week | 1 Month | 1 Month |
| Citrate Buffer pH 5.5 | 100.2 | 107.1 | 103.6 | 101.2 | 100.7 |
| Citrate Buffer pH 6 | 99.8 | 101 | 105 | 101.3 | 99.9 |
| Acetate Buffer pH 5.5 | 100.4 | 101.3 | 103.3 | 102.3 | 100.5 |
| Phosphate Buffer pH 6 | 99.7 | 100.4 | 103.4 | 101.3 | 101.2 |

Determination of acetaminophen and pregabalin in the combined dosage was performed using RP-HPLC with UV detection at 205 nm. Separation of APAP and PGB from each other and impurities and degradants that were present in the drug product was achieved by using a Thermo Scientific Hypersil GOLD aQ column.

The chromatographic conditions utilized in this procedure were as follows:

| | |
|---|---|
| System | Waters Alliance 2487 |
| Column | Thermo Scientific Hypersil GOLD aQ column, 5 μm, 4.6 × 250 mm |
| Column Temperature | 30 ± 3° C. |
| Sample Temperature | 5° C. |
| Injection Volume | 10 μL |

-continued

| | | | |
|---|---|---|---|
| Flow Rate | 1.5 mL/min | | |
| Detection | PDA/UV | | |
| Run Time | 34 Min | | |
| Gradient Elution | Time (min) | A (%) | B (%) |
| | 0 | 100 | 0 |
| | 25.00 | 0 | 100 |
| | 28.00 | 0 | 100 |
| | 28.01 | 100 | 0 |
| | 34.00 | 100 | 0 |
| Mobile Phase A | 98% 0.01M Potassium Dihydrogen Phosphate in Water pH 7 Buffer: 2% Acetonitrile | | |
| Mobile Phase B | 40% 0.01M Potassium Dihydrogen Phosphate in Water pH 7 Buffer: 60% Acetonitrile | | |

As shown in TABLES 7-9, the impurity levels were below detectable quantities when the solutions were stored at 40° C. (accelerated storage condition) or lower temperatures. When the solutions were stored at 60° C., the carrier solutions at pH 6 produced fewer impurities than the same conditions at pH 5.5.

For example, after one month, all of the tested samples were clear and colorless and showed no signs of precipitation at 25 and 40° C. In the one-month samples at 25 and 40° C., acetaminophen and pregabalin assay values were about 100% and no 4-aminophenol and MPP levels were observed.

As can be further seen from TABLES 10 and 11, negligible amounts of known impurities 4-aminophenol and 4-(2-methylpropyl)pyrrolidin-2-one (MPP, also referred to as pregabalin lactam) and unknown impurities were detected in the one-month month stability samples at 25 and 40° C.

TABLE 7

Related Substances (%)/RRT
60° C.

| | T0 | | | | | | 1 week | | | |
|---|---|---|---|---|---|---|---|---|---|---|
| Buffers | 4-Amino-phenol (0.64) | MPP (2.34) | Unknown (0.75) | Unknown (1.223) | Unknown (1.712) | Unknown (1.936) | 4-Amino-phenol (0.64) | MPP (2.34) | Unknown (0.75) | Unknown (1.223) |
| Citrate pH 5.5 | ND | ND | ND | ND | ND | ND | 0.38 | 3.20 | ND | ND |
| Citrate pH 6 | ND | ND | ND | ND | ND | ND | ND | 0.27 | ND | ND |
| Acetate pH 5.5 | ND | ND | ND | ND | ND | ND | ND | 1.69 | ND | 0.16 |
| Phosphate pH 6 | ND | ND | ND | 0.05 | ND | ND | ND | 0.47 | ND | 0.08 |

Related Substances (%)/RRT
60° C.

| | 1 week | | 2 week | | | | | |
|---|---|---|---|---|---|---|---|---|
| Buffers | Unknown (1.712) | Unknown (1.936) | 4-Amino-phenol (0.64) | MPP (2.34) | Unknown (0.75) | Unknown (1.223) | Unknown (1.712) | Unknown (1.936) |
| Citrate pH 5.5 | ND | ND | 0.07 | 3.99 | 0.39 | ND | ND | ND |
| Citrate pH 6 | ND | ND | ND | 1.35 | 0.06 | ND | ND | ND |
| Acetate pH 5.5 | 0.06 | 0.06 | ND | 1.68 | ND | ND | ND | ND |
| Phosphate pH 6 | ND | ND | ND | 1.13 | ND | 0.07 | ND | 0.05 |

ND—Not Detected

TABLE 8

Related Substances (%)/RRT
40° C.

| | T0 | | | | | | 1 month | | | | | |
|---|---|---|---|---|---|---|---|---|---|---|---|---|
| Buffers | 4-Amino-phenol (0.64) | MPP (2.34) | Unknown (0.75) | Unknown (1.223) | Unknown (1.712) | Unknown (1.936) | 4-Amino-phenol (0.64) | MPP (2.34) | Unknown (0.75) | Unknown (1.223) | Unknown (1.712) | Unknown (1.936) |
| Citrate pH 5.5 | ND | ND | ND | ND | ND | ND | ND | ND | ND | ND | ND | ND |
| Citrate pH 6 | ND | ND | ND | ND | ND | ND | ND | ND | ND | ND | ND | ND |
| Acetate pH 5.5 | ND | ND | ND | ND | ND | ND | ND | ND | ND | ND | ND | ND |

TABLE 8-continued

| | Related Substances (%)/RRT 40° C. | | | | | | | | | | | |
|---|---|---|---|---|---|---|---|---|---|---|---|---|
| | T0 | | | | | | 1 month | | | | | |
| Buffers | 4-Amino-phenol (0.64) | MPP (2.34) | Unknown (0.75) | Unknown (1.223) | Unknown (1.712) | Unknown (1.936) | 4-Amino-phenol (0.64) | MPP (2.34) | Unknown (0.75) | Unknown (1.223) | Unknown (1.712) | Unknown (1.936) |
| Phosphate pH 6 | ND | ND | ND | 0.05 | ND | ND | ND | ND | ND | ND | ND | ND |

ND—Not detected.

TABLE 9

| | Related Substances (%)/RRT 25° C. | | | | | | | | | | | |
|---|---|---|---|---|---|---|---|---|---|---|---|---|
| | T0 | | | | | | 1 month | | | | | |
| Buffers | 4-Amino-phenol (0.64) | MPP (2.34) | Unknown (0.75) | Unknown (1.223) | Unknown (1.712) | Unknown (1.936) | 4-Amino-phenol (0.64) | MPP (2.34) | Unknown (0.75) | Unknown (1.223) | Unknown (1.712) | Unknown (1.936) |
| Citrate pH 5.5 | ND | ND | ND | ND | ND | ND | ND | ND | ND | ND | ND | ND |
| Citrate pH 6 | ND | ND | ND | ND | ND | ND | ND | ND | ND | ND | ND | ND |
| Acetate pH 5.5 | ND | ND | ND | ND | ND | ND | ND | ND | ND | ND | ND | ND |
| Phosphate pH 6 | ND | ND | ND | 0.05 | ND | ND | ND | ND | ND | ND | ND | ND |

ND—Not detected.

Example 3: Pharmacokinetic Parameters of Acetaminophen-Pregabalin Combination Formulations Formulations for testing were prepared by weighing pregabalin and/or acetaminophen as indicated in TABLE 10 in a glass vial. The active ingredients were dissolved in 0.9% saline (20 mL) to achieve the desired concentration. The saline and vial constituents were mixed with by gentle swirling until a clear solution was obtained. The obtained clear solution was filtered through a sterile 0.45 μm PVDF membrane syringe filter and then used for further studies.

TABLE 10

| | Drug/vial (mg) | |
|---|---|---|
| Group | Acetaminophen | Pregabalin |
| Acetaminophen (10 mg/mL) | 200 | — |
| Pregabalin (0.75 mg/mL) | — | 15 |
| Pregabalin (3 mg/mL) | — | 60 |
| Acetaminophen (10 mg/mL) & Pregabalin (0.75 mg/mL) | 200 | 15 |
| Acetaminophen (10 mg/mL) & Pregabalin (3 mg/mL) | 200 | 60 |

Pharmacokinetic parameters were analyzed after 15 min infusion of acetaminophen, pregabalin, and acetaminophen and pregabalin combination formulations in rats over a 24 h period (TABLE 11, FIG. 1—Acetaminophen; TABLE 12, FIG. 2—Pregabalin).

Figure 2:
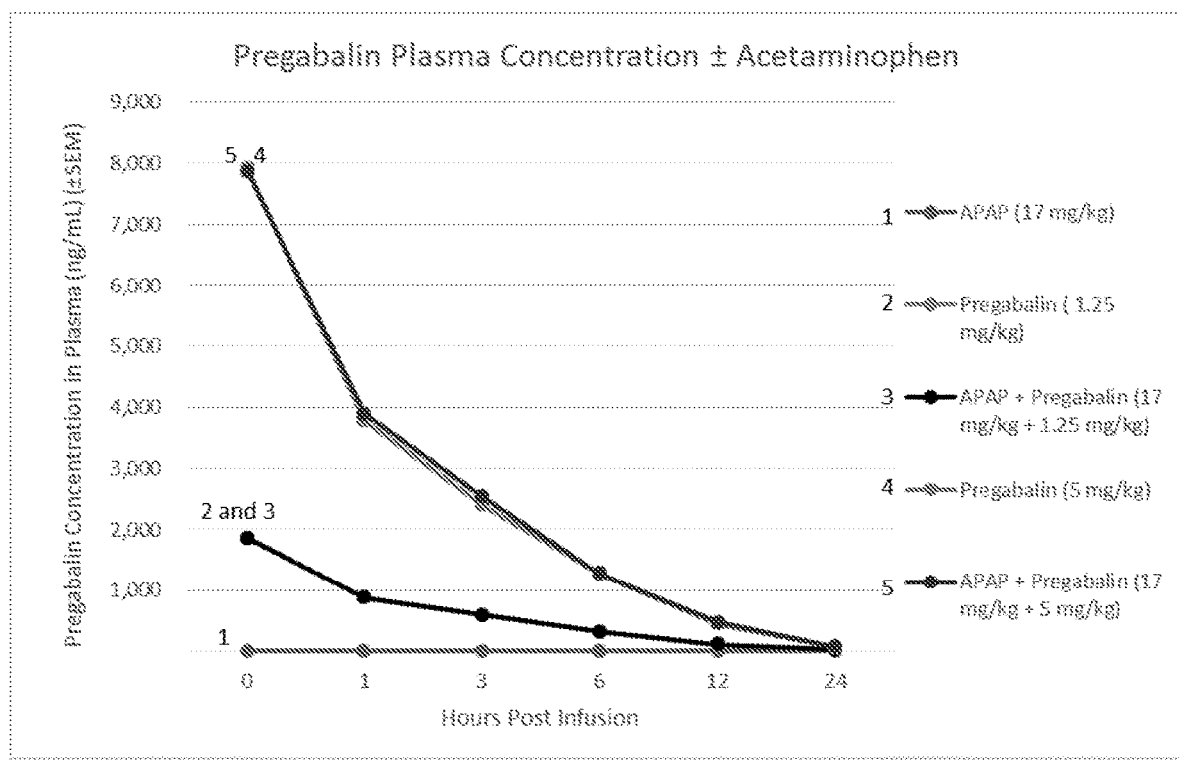
FIG. 2 shows a graph of plasma concentration of pregabalin either administered alone or in combination with acetaminophen after intravenous administration.

The presence or absence of pregabalin did not affect the pharmacokinetics of acetaminophen in rats (TABLE 11; FIG. 1). No change in the pharmacokinetic profile of pregabalin was observed in the presence or absence of acetaminophen (TABLE 12; FIG. 2).

When the general range for equivalence (80% to 125%) was determined, both parameters ($C_{max}$ and AUC) were within the equivalence ranges. This finding further supported the lack of effect of either drug on the pharmacokinetic profile of the other drug. Therefore, the combination of acetaminophen and pregabalin did not alter the Maximal Blood Concentration ($C_{max}$), nor the total exposure (AUC) compared to either drug given alone.

TABLE 11

| | | | Equivalence (80%-125%) | |
|---|---|---|---|---|
| Group | $C_{max}$ (ng/mL) | $AUC_{0-\infty}$ (ng · h/mL) | $C_{max}$ (ng/mL) | $AUC_{0-\infty}$ (ng · h/mL) |
| APAP (17 mg/kg) | 18,633 | 11,482 | 14,906-23,291 | 9,186-14,353 |
| Pregabalin (1.25 mg/kg) | 0 | 0 | | |
| Pregabalin (5 mg/kg) | 0 | 0 | | |
| APAP (17 mg/kg) + Pregabalin (1.25 mg/kg) | 16,533 | 9,829 | | |
| APAP (17 mg/kg) + Pregabalin (5 mg/kg) | 18,500 | 10,928 | | |

TABLE 12

| Group | Equivalence (80%-125%) | | | |
|---|---|---|---|---|
| | $C_{max}$ (ng/mL) | $AUC_{0-\infty}$ (ng·h/mL) | $C_{max}$ (ng/mL) | $AUC_{0-\infty}$ (ng·h/mL) |
| APAP (17 mg/kg) | 0 | 0 | | |
| Pregabalin (1.25 mg/kg) | 2,063 | 6,754 | 1,650-2,579 | 5,403-8,443 |
| Pregabalin (5 mg/kg) | 7,908 | 26,126 | 6,326-9,885 | 20,901-32,658 |
| APAP (17 mg/kg) + Pregabalin (1.25 mg/kg) | 1,858 | 6,455 | | |
| APAP (17 mg/kg) + Pregabalin (5 mg/kg) | 7,863 | 23,717 | | |

To evaluate the pharmacokinetic and toxicological profiles of the combination formulations, rats were administered a 15 minute intravenous infusion of acetaminophen (10 mg/mL), pregabalin (0.75 mg/mL), pregabalin (3 mg/mL), acetaminophen (10 mg/mL)+pregabalin (0.75 mg/mL), acetaminophen (10 mg/mL)+pregabalin (3 mg/mL), or a vehicle control. Blood samples were collected over a 24 h period, at which time the rats were exsanguinated, and the blood was collected for clinical pathology evaluation (chemistry, hematology, and coagulation). Finally, all the animals were necropsied (all exterior and interior cavities and organs were examined), and the site of infusion in the jugular vein, lung, liver, and kidney underwent histopathologic evaluation.

Results from this study demonstrated that under the conditions of this study, the combination formulation of acetaminophen and pregabalin did not alter clinical pathology parameters (hematology—TABLE 13, coagulation—TABLE 14, clinical chemistry—TABLE 15). Further, no changes were observed in the histopathology in any tissue sampled compared to the vehicle control (as shown for lung in TABLE 16).

TABLE 13

| Hematology parameter | | Saline | APAP (17 mg/kg) | PGB (1.25 mg/kg) | PGB (5 mg/kg) | APAP (17 mg/kg) + PGB (1.25 mg/kg) | APAP (17 mg/kg) + PGB (5 mg/kg) |
|---|---|---|---|---|---|---|---|
| WBC [$\times 10^3/\mu L$] | Mean | 13.13 | 11.62 | 11.74 | 13.28 | 13.07 | 12.61 |
| | S.D. | 1.86 | 2.62 | 1.62 | 1.65 | 3.41 | 1.4 |
| Neutrophils [$\times 10^3/\mu L$] | Mean | 1.44 | 1.69 | 1.4 | 1.52 | 1.45 | 1.64 |
| | S.D. | 0.61 | 0.82 | 0.55 | 0.34 | 0.45 | 0.76 |
| Lymphocytes [$\times 10^3/\mu L$] | Mean | 10.79 | 9.18 | 9.4 | 10.81 | 10.6 | 10.18 |
| | S.D. | 1.55 | 1.58 | 1.08 | 1.53 | 3.08 | 0.85 |
| Monocytes [$\times 10^3/\mu L$] | Mean | 0.45 | 0.3 | 0.5 | 0.45 | 0.46 | 0.42 |
| | S.D. | 0.17 | 0.12 | 0.31 | 0.12 | 0.19 | 0.14 |
| Eosinophils [$\times 10^3/\mu L$] | Mean | 0.31 | 0.32 | 0.28 | 0.35 | 0.38 | 0.23 |
| | S.D. | 0.06 | 0.16 | 0.11 | 0.19 | 0.09 | 0.12 |
| Basophils [$\times 10^3/\mu L$] | Mean | 0.08 | 0.07 | 0.08 | 0.08 | 0.09 | 0.07 |
| | S.D. | 0.02 | 0.03 | 0.05 | 0.02 | 0.02 | 0.02 |
| LGLUCLE [$\times 10^3/\mu L$] | Mean | 0.07 | 0.06 | 0.10 | 0.08 | 0.1 | 0.07 |
| | S.D. | 0.02 | 0.02 | 0.09 | 0.02 | 0.05 | 0.02 |
| RBC [$\times 10^6/\mu L$] | Mean | 8.31 | 8.29 | 7.93 | 7.9 | 7.89 | 8.19 |
| | S.D. | 0.49 | 0.6 | 0.18 | 0.18 | 0.31 | 0.59 |
| Hemoglobin [g/dL] | Mean | 15.2 | 15.1 | 14.2 | 14.4 | 14.3 | 15.1 |
| | S.D. | 0.9 | 0.8 | 0.3 | 0.5 | 0.8 | 0.7 |
| Hematocrit [%] | Mean | 48.6 | 47.7 | 44.2 | 45.1 | 44.5 | 47.8 |
| | S.D. | 3.7 | 3.4 | 1 | 2.2 | 3 | 2.7 |
| MCV [fL] | Mean | 58.5 | 57.6 | 55.8 | 57.1 | 56.3 | 58.4 |
| | S.D. | 1.8 | 1.5 | 1 | 2.2 | 1.9 | 1.4 |
| MCH [pg] | Mean | 18.3 | 18.2 | 17.8 | 18.3 | 18.1 | 18.5 |
| | S.D. | 0.3 | 0.5 | 0.2 | 0.5 | 0.4 | 0.7 |
| MCHC [g/dL] | Mean | 31.2 | 31.6 | 32 | 32.1 | 32.1 | 31.6 |
| | S.D. | 0.7 | 0.6 | 0.5 | 0.5 | 0.4 | 0.4 |
| Platelets [$\times 10^3/\mu L$] | Mean | 885 | 883 | 908 | 933 | 992 | 964 |
| | S.D. | 135 | 98 | 80 | 38 | 152 | 293 |
| Reticulocytes [%] | Mean | 5.02 | 4.37 | 4.11 * | 4.7 | 4.27 | 5.04 |
| | S.D. | 0.16 | 0.74 | 0.51 | 0.4 | 0.22 | 0.54 |

WBC—white blood cell, LGLUCLE—large unstained cell, RBC—red blood cell, MCV—mean cell volume, MCH—mean cell hemoglobin, MCHC—mean cell hemoglobin concentration.
Saline: n = 5 per group, all others:
n = 6 per group.
* = $p < 0.05$ by ANOVA.

TABLE 14

| Coagulation parameter | | Saline | APAP (17 mg/kg) | PGB (1.25 mg/kg) | PGB (5 mg/kg) | APAP (17 mg/kg) + PGB (1.25 mg/kg) | APAP (17 mg/kg) + PGB (5 mg/kg) |
|---|---|---|---|---|---|---|---|
| Prothrombin time [seconds] | Mean | 16.6 | 16.6 | 16.8 | 16.6 | 17 | 16.5 |
| | S.D. | 0.6 | 0.9 | 0.7 | 0.7 | 0.7 | 0.5 |

TABLE 14-continued

| Coagulation parameter | | Saline | APAP (17 mg/kg) | PGB (1.25 mg/kg) | PGB (5 mg/kg) | APAP (17 mg/kg) + PGB (1.25 mg/kg) | APAP (17 mg/kg) + PGB (5 mg/kg) |
|---|---|---|---|---|---|---|---|
| APPT [seconds] | Mean | 13 | 13.3 | 12.9 | 12.4 | 12.4 | 12 |
|  | S.D. | 0.5 | 1.2 | 1 | 1.6 | 0.4 | 1.6 |

APPT—Activated partial thromboplastin time.
Saline: n = 5 per group, all others: n = 6 per group.

TABLE 15

| Clinical Chemistry Parameter | | Saline | APAP (17 mg/kg) | PGB (1.25 mg/kg) | PGB (5 mg/kg) | APAP (17 mg/kg) + PGB (1.25 mg/kg) | APAP (17 mg/kg) + PGB (5 mg/kg) |
|---|---|---|---|---|---|---|---|
| Sodium [mEq/L] | Mean | 146 | 146 | 148 * | 147 | 148 * | 147 |
|  | S.D. | 2 | 1 | 1 | 1 | 2 | 1 |
| Potassium [mEq/L] | Mean | 8.6 | 8.4 | 7.3 | 6.9 * | 7.0 * | 7.9 |
|  | S.D. | 1.3 | 0.9 | 0.3 | 0.2 | 0.6 | 1.4 |
| Chloride [mEq/L] | Mean | 102 | 102 | 102 | 101 | 102 | 101 |
|  | S.D. | 1 | 1 | 1 | 1 | 1 | 1 |
| Albumin [g/dL] | Mean | 3.9 | 3.9 | 4.0 | 3.9 | 3.9 | 4.0 |
|  | S.D. | 0.1 | 0.1 | 0.2 | 0.1 | 0.1 | 0.1 |
| ALP [U/L] | Mean | 106 | 95 | 99 | 97 | 99 | 98 |
|  | S.D. | 24 | 11 | 11 | 5 | 10 | 14 |
| ALT [U/L] | Mean | 59 | 48 | 45 | 51 | 48 | 50 |
|  | S.D. | 16 | 10 | 5 | 6 | 9 | 6 |
| AST [U/L] | Mean | 133 | 102 * | 93 ** | 107 | 105 * | 104 * |
|  | S.D. | 34 | 14 | 8 | 10 | 13 | 9 |
| UREAN [mg/dL] | Mean | 20 | 21 | 19 | 19 | 21 | 18 |
|  | S.D. | 3 | 3 | 2 | 1 | 2 | 2 |
| Calcium [mg/dL] | Mean | 11.9 | 11.5 | 11.4 | 11.5 | 11.3 | 11.9 |
|  | S.D. | 0.5 | 0.5 | 0.4 | 0.1 | 0.3 | 0.7 |
| Cholesterol [mg/dL] | Mean | 91 | 88 | 94 | 93 | 80 | 90 |
|  | S.D. | 8 | 13 | 18 | 5 | 14 | 14 |
| Creatinine [mg/dL] | Mean | 0.48 | 0.44 | 0.47 | 0.44 | 0.43 | 0.44 |
|  | S.D. | 0.07 | 0.03 | 0.02 | 0.02 | 0.06 | 0.03 |
| Glucose [mg/dL] | Mean | 147 | 147 | 166 | 150 | 143 | 131 |
|  | S.D. | 24 | 25 | 27 | 16 | 22 | 34 |
| PHOS [mg/dL] | Mean | 12.5 | 11 | 10.6 | 10 ** | 10.5 * | 11.9 |
|  | S.D. | 1.4 | 1.6 | 0.4 | 0.3 | 0.7 | 2.1 |
| Bilirubin [mg/dL] | Mean | 0.02 | 0.02 | 0.02 | 0.02 | 0.02 | 0.02 |
|  | S.D. | 0 | 0 | 0 | 0.01 | 0 | 0.01 |
| Protein [g/dL] | Mean | 6.8 | 6.7 | 6.7 | 6.7 | 6.7 | 6.9 |
|  | S.D. | 0.2 | 0.2 | 0.3 | 0.2 | 0.1 | 0.2 |
| Triglycerides [mg/dL] | Mean | 32 | 32 | 33 | 30 | 28 | 30 |
|  | S.D. | 9 | 9 | 10 | 6 | 6 | 5 |
| GLOBUL [g/dL] | Mean | 2.8 | 2.8 | 2.8 | 2.8 | 2.8 | 2.9 |
|  | S.D. | 0.1 | 0.2 | 0.1 | 0.1 | 0.1 | 0.2 |
| ALBGLOB | Mean | 1.4 | 1.4 | 1.4 | 1.4 | 1.4 | 1.4 |
|  | S.D. | 0.1 | 0.1 | 0.1 | 0.1 | 0 | 0.1 |

ALP—alkaline phosphatase, ALT—alanine aminotransferase, AST—aspartate aminotransferase, UREAN—blood urea nitrogen, PHOS—inorganic phosphorus, GLOBUL—globulin (calculated), ALBGLOB—albumin/globulin ratio (calculated).
n = 6 per group.
* = p < 0.05,
** = p < 0.01 by ANOVA-DUNNETT.

TABLE 16

| Necropsy Observation | | Saline | APAP (17 mg/kg) | PGB (1.25 mg/kg) | PGB (5 mg/kg) | APAP (17 mg/kg) + PGB (1.25 mg/kg) | APAP (17 mg/kg) + PGB (5 mg/kg) |
|---|---|---|---|---|---|---|---|
| Lung | Discolored | 0 | 0 | 1 | 0 | 0 | 0 |
|  | Focus | 1 | 1 | 1 | 2 | 0 | 0 | n = 6 per group.

Example 4: Analysis of Drug-Induced Autoimmune Hemolytic Anemia by Combination Formulation Acetaminophen and pregabalin, alone or in combination, were evaluated using an in vitro hemolysis test with four biologic matrices (mouse, rat, dog, and human whole unclotted blood) to determine the hemolytic potential for each compound on red blood cells.

The blood was mixed with either acetaminophen (5, 7.5, 10 mg/mL); pregabalin (0.75, 1.5, and 3 mg/mL); acetaminophen (10 mg/mL)+pregabalin (0.75, 1.5 and 3 mg/mL); a saline control; or a positive control (2% SDS), and incubated for 15 min at 37° C.

Based on the results of this study (TABLES 17 and 18), the combination of acetaminophen and pregabalin did not cause hemolysis in the blood from mice, rats, dogs, or humans under the tested conditions.

TABLE 17

| Species | % Hemolysis | | |
|---|---|---|---|
| | APAP (5 mg/mL) | APAP (7.5 mg/mL) | APAP (10 mg/mL) |
| Test Formulation 1 | | | |
| Mouse Blood | 5 | 5 | 4 |
| Rat Blood | 6 | 0 | 2 |
| Dog Blood | 0 | 0 | 0 |
| Human Blood | 2 | 0 | 6 |

| Species | % Hemolysis | | |
|---|---|---|---|
| | PGB (0.75 mg/mL) | PGB (1.5 mg/mL) | PGB (3 mg/mL) |
| Test Formulation 2 | | | |
| Mouse Blood | 0 | 4 | 0 |
| Rat Blood | 2 | 0 | 2 |
| Dog Blood | 0 | 0 | 1 |
| Human Blood | 0 | 7 | 1 |

| Species | % Hemolysis | | |
|---|---|---|---|
| | APAP (10 mg/mL) + PGB (0.75 mg/mL) | APAP (10 mg/mL) + PGB (1.5 mg/mL) | APAP (10 mg/mL) + PGB (3 mg/mL) |
| Test Formulation 3 | | | |
| Mouse Blood | 3 | 1 | 2 |
| Rat Blood | 8 | 8 | 0 |
| Dog Blood | 0 | 0 | 0 |
| Human Blood | 3 | 4 | 0 |

TABLE 18

| Criteria for Determination of Hemolysis | |
|---|---|
| Percent Hemolysis | Interpretation |
| <10% | Not Hemolytic |
| 10%-25% | Relative Boundary (Possibly Hemolytic) |
| >25% | Hemolytic |

Example 5: Pharmacodynamic Parameters of Combination Formulation

To determine the pharmacodynamic parameters of the combination formulation, acetaminophen, pregabalin, or the combination, were administered to rats. The effect of the compounds on the rats was assessed by the rotarod test.

To test the effect of pregabalin alone, different doses of pregabalin (5, 10, 20, 40, 60, 80 and 100 mg/kg), were administered to the rats as a 15 minute infusion. The effect of pregabalin on the motor control of the rats was assessed in groups of 5 male Sprague-Dawley rats. Vehicle and test agents were administered by intravenous infusion (IV-CI) over 15 minutes starting 30 minutes before time 0 (15 minutes post-infusion). Chlorpromazine (30 mg/kg) was administered via oral gavage (PO) as a positive control 60 minutes before Time 0 to a group of rats that served as a positive control for the experiment.

At Time 0 and 1 hour after Time 0, the rats were placed on the accelerating rotarod, and the time (seconds) the rats remained on the rotarod was recorded.

Figure 3:
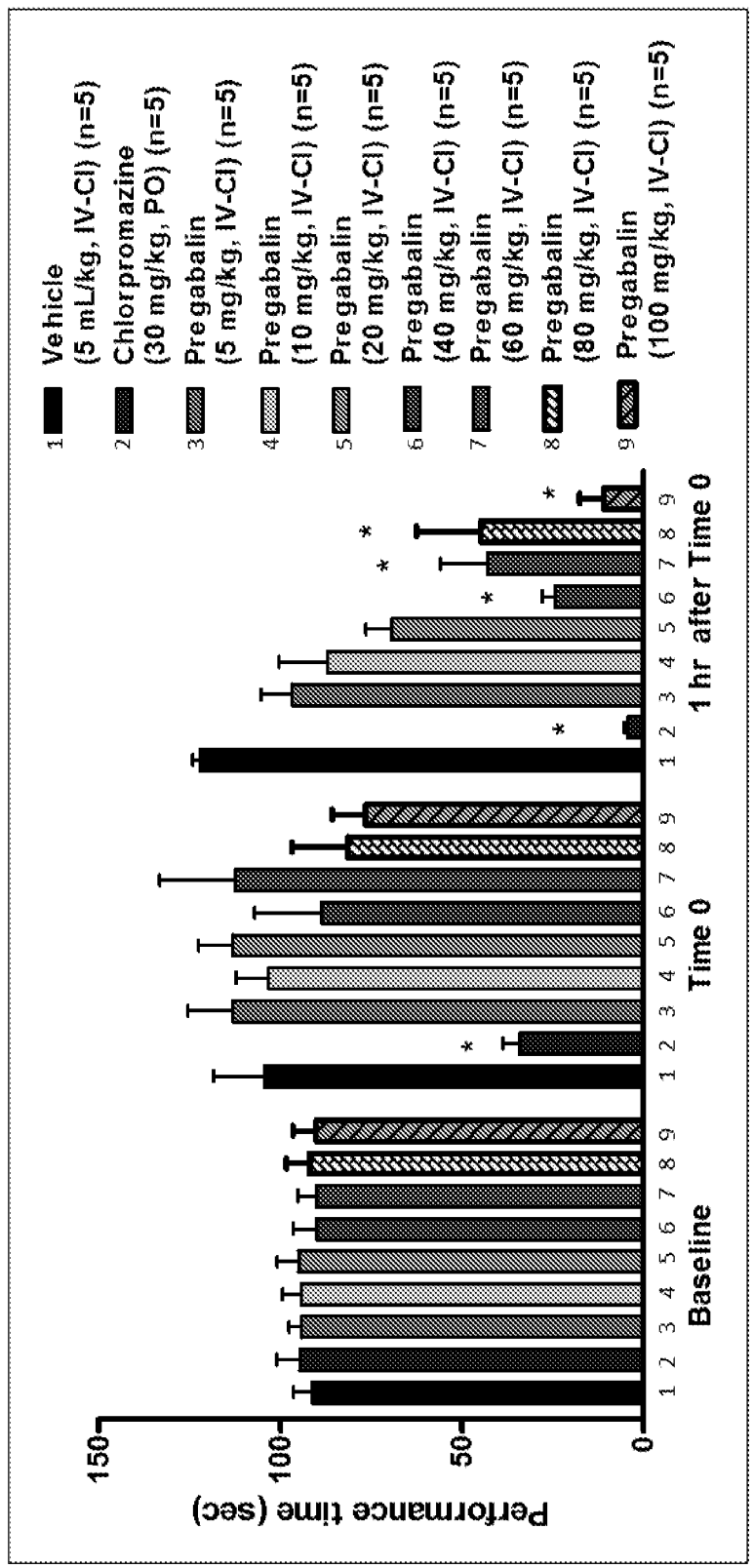
FIG. 3 shows a graph of the effects of increasing pregabalin doses on motor control in a rat model after oral administration of pregabalin.

The results were analyzed by a one-way ANOVA followed by Dunnett's test for comparison between vehicle control and test article/positive control groups. A p-value of less than 0.05, as shown with asterisk in FIG. 3, was considered to indicate a statistically significant inhibition of motor coordination. The inhibition of motor control indicated marked somnolence/dizziness due to the effects of the test agent.

Further, the effect of pregabalin was tested with or without acetaminophen to see whether the combination of acetaminophen and pregabalin affected the pharmacodynamics of pregabalin.

Different doses of pregabalin (10, 20, or 40 mg/kg) with or without acetaminophen (50 mg/kg) were administered to the rats as a 15 minute infusion, and the effect of pregabalin on the motor control of the rats was assessed in groups of 5 male Sprague-Dawley rats. Vehicle and test agents were administered by intravenous infusion (IV-CI) over 15 minutes starting 30 minutes before Time 0 (15 minutes post infusion). Chlorpromazine (30 mg/kg) was administered via oral gavage (PO) 60 minutes before Time 0 to a group of rats that served as a positive control for the experiment. At Time 0 and 1 hour after Time 0, the rats were placed on the accelerating rotarod, and the time (seconds) the rat remained on the rotarod was recorded.

Figure 4:
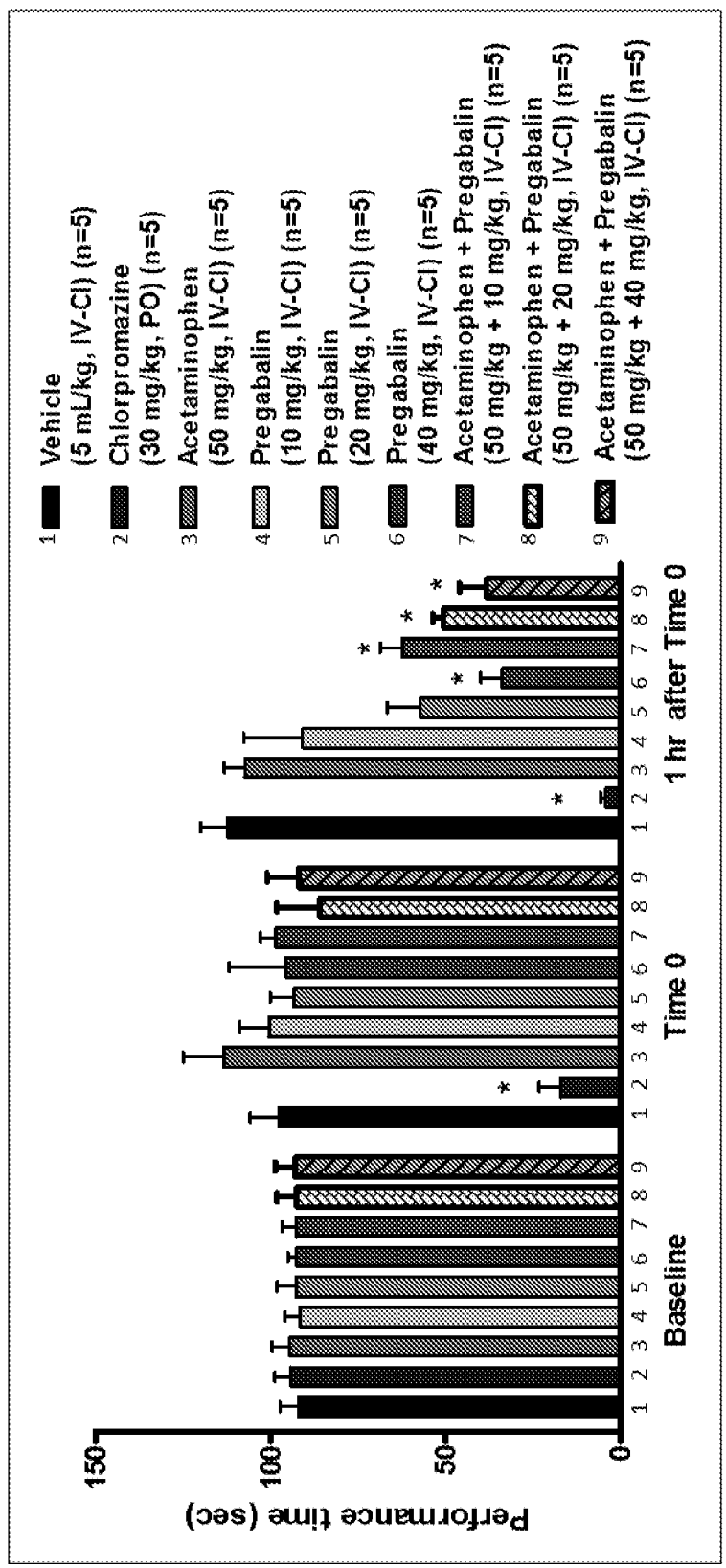
FIG. 4 shows a graph of effects of pregabalin in the presence or absence of acetaminophen on motor control in a rat model after intravenous administration of pregabalin.

Results were analyzed by a one-way ANOVA followed by Dunnett's test for comparison between vehicle control and test article/positive control groups. A p-value of less than 0.05, as shown with asterisk in FIG. 4, was considered to indicate a statistically significant inhibition of motor coordination. The inhibition of motor control indicated marked somnolence/dizziness due to the effects of the test agent.

Example 6: Analysis of the Effect on Somatic Pain of Combination Formulation The hot plate test was used to assess the effect on somatic pain after administration of pregabalin, acetaminophen, or a combination formulation. Different doses of pregabalin (10, 20, or 40 mg/kg) with or without acetaminophen (50 mg/kg) were administered as a 15 minute infusion. The effect on somatic pain was tested in groups of 8 Male Sprague-Dawley rats.

Vehicle and test agents were administered by intravenous infusion (IV-CI) over 15 minutes starting 30 minutes before Time 0 (15 minutes post infusion). Morphine was used as a positive control, and was administered (3 mg/kg) by subcutaneous administration 60 minutes before Time 0. At Time 0 and 1 hour after Time 0, the rats were placed on a strong thermal stimulus at 52° C. (hot plate). The pain threshold of the rats was assessed based on the time (seconds) required to elicit a paw withdrawal response (latency).

Figure 5:
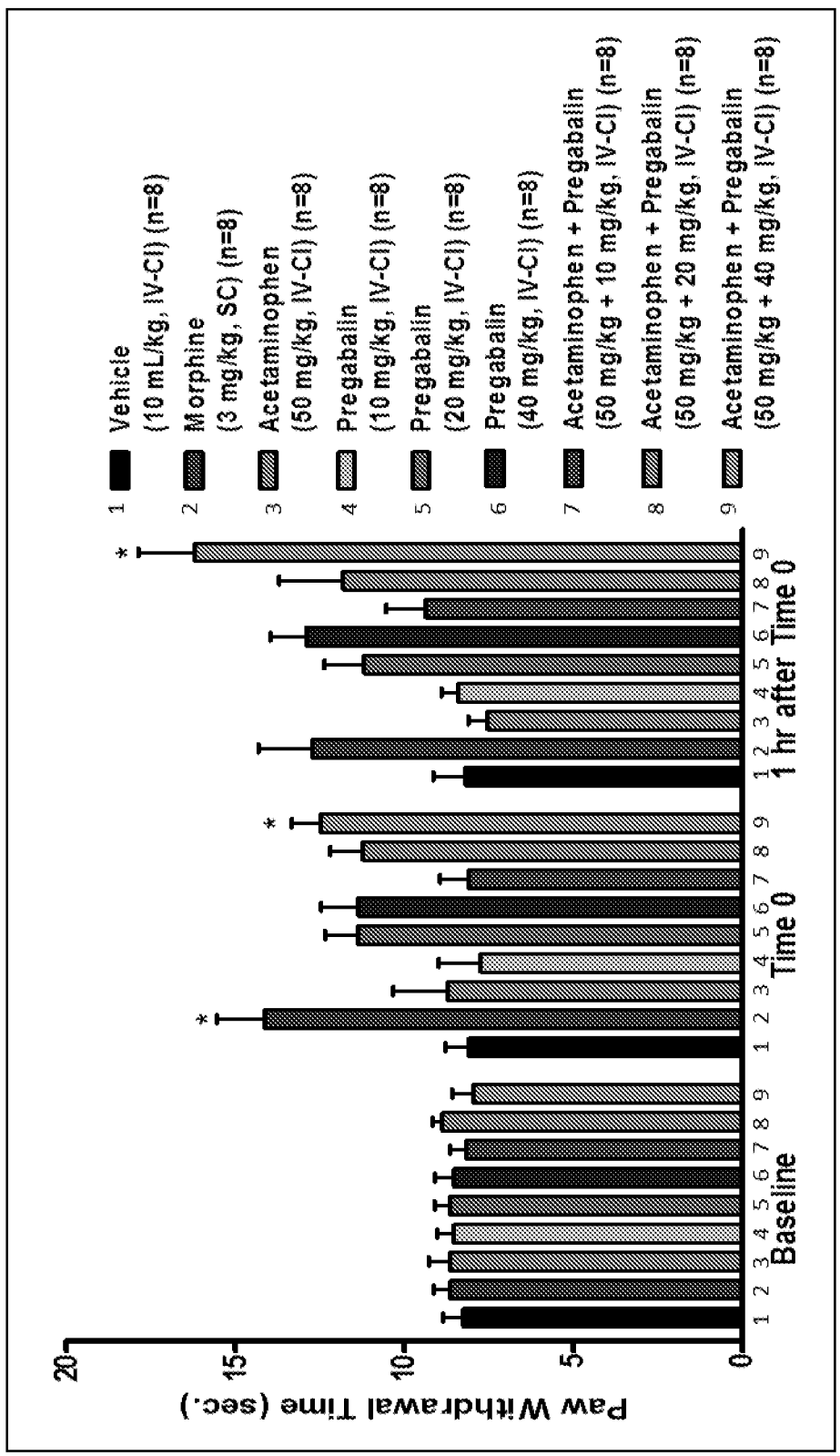
FIG. 5 shows a graph of effects of pregabalin in the presence or absence of acetaminophen on somatic pain in a rat model after intravenous administration.

The results are shown in FIG. 5. The data were analyzed by a one-way ANOVA followed by Dunnett's test for comparison between vehicle control and test article/positive control groups. A p-value of less than 0.05 indicated a statistically significant inhibition of the rats' ability to detect somatic pain from an external source. This result indicated that the combination of pregabalin and acetaminophen inhibited somatic pain.

As can be seen from FIG. 5, the onset of the analgesic effect was (as expected) near immediate for morphine. The onset for at least one combination (50 mg/kg APAP; 40 mg/kg pregabalin) was relatively quick. FIG. 5 shows that the 50 mg/kg acetaminophen; 40 mg/kg pregabalin formulation increased the latency to about 16 seconds versus the initial latency of about 8 seconds at baseline. Moreover, at least one combination (50 mg/kg APAP; 40 mg/kg pregabalin) had a synergistic analgesic effect that exceeded the effect and duration of analgesia provided by morphine.

Example 7: Analysis of Impurity Levels in Combination Formulation Using Different Buffers and pH Several formulations of acetaminophen and pregabalin were tested, in which the buffer and the pH were varied to determine the impurity level in the formulations.

TABLE 19-25 show different combination formulations (A-G) of acetaminophen and pregabalin that were tested in various buffers at pH 5.5 or 6. TABLES 26-32 provide the impurities that were detected for both pregabalin and acetaminophen. The number underneath each impurity in TABLES 26-32 indicates the relative retention time of the impurities.

TABLE 19 (A)

| Composition | mg/mL |
|---|---|
| Acetaminophen | 10 |
| Pregabalin | 20 |
| Sodium Chloride | 5.5 |
| Sodium Dihydrogen Phosphate | 1.87 |
| NaOH 5N | q.s. to pH 6 |
| Water for Injection | q.s. to 1 mL |

TABLE 20 (B)

| Composition | mg/mL |
|---|---|
| Acetaminophen | 10 |
| Pregabalin | 20 |
| Sodium Chloride | 2.25 |
| Citric Acid Monohydrate | 2.101 |
| NaOH 5N | q.s. to pH 6 |
| Water for Injection | q.s. to 1 mL |

TABLE 21 (C)

| Composition | mg/mL |
|---|---|
| Acetaminophen | 10 |
| Pregabalin | 20 |
| Sodium Chloride | 2.25 |
| L-Histidine | 1.55 |
| NaOH 5N | q.s. to pH 6 |
| Water for Injection | q.s. to 1 mL |

TABLE 22 (D)

| Composition | mg/mL |
|---|---|
| Acetaminophen | 10 |
| Pregabalin | 4.5 |
| Sodium Chloride | 5 |
| Citric Acid Monohydrate | 2.101 |
| NaOH 5N | q.s. to pH 5.5 |
| Water for Injection | q.s. to 1 mL |

TABLE 23 (E)

| Composition | mg/mL |
|---|---|
| Acetaminophen | 10 |
| Pregabalin | 4.5 |
| Sodium Chloride | 5 |
| Citric Acid Monohydrate | 2.101 |
| NaOH 5N | q.s. to pH 6 |
| Water for Injection | q.s. to 1 mL |

TABLE 24 (F)

| Composition | mg/mL |
|---|---|
| Acetaminophen | 10 |
| Pregabalin | 4.5 |
| Sodium Chloride | 5 |
| Acetic Acid | 0.6 |
| NaOH 5N | q.s. to pH 5.5 |
| Water for Injection | q.s. to 1 mL |

TABLE 25 (G)

| Composition | mg/mL |
|---|---|
| Acetaminophen | 10 |
| Pregabalin | 4.5 |
| Sodium Chloride | 5.5 |
| Sodium Dihydrogen Phosphate | 1.2 |
| NaOH 5N | q.s. to pH 6 |
| Water for Injection | q.s. to 1 mL |

TABLE 26 (A)

| | | | | | | Results | | | | | | |
|---|---|---|---|---|---|---|---|---|---|---|---|---|
| | | | | | | | Related Substances (%)/RRT | | | | | |
| | | | | | | | APAP | | | | | PGB |
| Interval | Appearance | pH | Osmolality (mOsm) | PGB (%) | APAP (%) | 4-Amino-phenol 0.64 | Unk 0.7 | Unk 1.1 | Unk 1.11 | Unk 1.38 | Unk 2.69 | MPP 2.34 |
| 0 time | Clear, colorless liquid | 6 | 392 | 97 | 98.1 | ND | ND | ND | ND | ND | ND | ND |
| 1 Month: 25° C. | Clear, colorless liquid | 6.04 | N/A | 99.7 | 99.5 | ND | ND | ND | ND | ND | ND | ND |
| 1 Month: 40° C. | Clear, colorless liquid | 6.03 | N/A | 99.8 | 100.4 | ND | ND | ND | ND | ND | ND | ND |
| 2 Months: 25° C. | Clear, colorless liquid | 6.07 | N/A | 100.7 | 100.5 | ND | ND | ND | ND | ND | ND | ND |
| 2 Months: 40° C. | Clear, colorless liquid | 6.12 | N/A | 100.5 | 102 | ND | ND | ND | ND | ND | ND | ND |
| 3 Months: 25° C. | Clear, colorless liquid | 6.06 | N/A | 99 | 102 | ND | ND | ND | ND | ND | ND | ND |
| 3 Months: 40° C. | Clear, colorless liquid | 6.06 | N/A | 99.9 | 99.8 | ND | ND | ND | ND | ND | ND | 0.1 |
| 6 Months: 25° C. | Clear, colorless liquid | 6.07 | N/A | 98.2 | 102 | ND | ND | ND | ND | ND | ND | ND |
| 6 Months: 40° C. | Clear, colorless liquid | 6.05 | N/A | 100.2 | 104.3 | ND | ND | ND | ND | ND | ND | 0.29 |

TABLE 27 (B)

| | | | | | | Results | | | | | | |
|---|---|---|---|---|---|---|---|---|---|---|---|---|
| | | | | | APAP (%) | | Related Substances (%)/RRT | | | | | |
| | | | | | | | APAP | | | | | PGB |
| Interval | Appearance | pH | Osmolality (mOsm) | PGB (%) | | 4-Amino-phenol 0.64 | Unk 0.7 | Unk 1.1 | Unk 1.11 | Unk 1.38 | Unk 2.69 | MPP 2.34 |
| 0 time | Clear, colorless liquid | 6 | 299 | 97.5 | 96.8 | ND | 0.14 | ND | ND | ND | ND | ND |
| 1 Month: 25° C. | Clear, colorless liquid | 6 | N/A | 99.4 | 99.3 | ND | ND | ND | ND | ND | ND | ND |
| 1 Month: 40° C. | Clear, colorless liquid | 6.04 | N/A | 99.7 | 100.8 | ND | ND | ND | ND | ND | ND | ND |
| 2 Months: 25° C. | Clear, colorless liquid | 6.07 | N/A | 99 | 100.3 | ND | ND | ND | ND | ND | ND | ND |
| 2 Months: 40° C. | Clear, colorless liquid | 6.08 | N/A | 100.7 | 101.2 | ND | ND | ND | ND | ND | ND | ND |
| 3 Months: 25° C. | Clear, colorless liquid | 6.05 | N/A | 99.3 | 100.5 | ND | ND | ND | ND | ND | ND | ND |
| 3 Months: 40° C. | Clear, colorless liquid | 6.06 | N/A | 100 | 101.2 | ND | ND | ND | ND | ND | ND | 0.07 |
| 6 Months: 25° C. | Clear, colorless liquid | 6.05 | N/A | 98.6 | 102.6 | ND | ND | ND | ND | ND | ND | ND |
| 6 Months: 40° C. | Clear, colorless liquid | 6.07 | N/A | 100.4 | 104.6 | ND | ND | ND | ND | ND | ND | 0.24 |

TABLE 28 (C)

| | | | | | Results | | | | | | |
|---|---|---|---|---|---|---|---|---|---|---|---|
| | | | | | APAP (%) | Related Substances (%)/RRT | | | | | |
| | | | | | | APAP | | | | | PGB |
| Interval | Appearance | pH | Osmolality (mOsm) | PGB (%) | 4-Amino-phenol 0.64 | Unk 0.7 | Unk 1.1 | Unk 1.11 | Unk 1.38 | Unk 2.69 | MPP 2.34 |
| 0 time | Clear, colorless liquid | 6.02 | 284 | 97.2  98.4 | ND | ND | ND | ND | ND | ND | ND |
| 1 Month: 25° C. | Clear, colorless liquid | 6.01 | N/A | 99.8  100 | ND | ND | ND | ND | ND | ND | ND |
| 1 Month: 40° C. | Clear, colorless liquid | 6.02 | N/A | 99.8  100.6 | ND | ND | ND | ND | ND | ND | ND |
| 2 Months: 25° C. | Clear, colorless liquid | 6.1 | N/A | 99.4  99.9 | ND | ND | ND | ND | ND | ND | ND |
| 2 Months: 40° C. | Clear, yellow colored liquid | 6.1 | N/A | 99.8  100.8 | ND | ND | ND | ND | ND | ND | ND |
| 3 Months: 25° C. | Clear, colorless liquid | 6.09 | N/A | 99.3  101.5 | ND | ND | ND | ND | ND | ND | ND |
| 3 Months: 40° C. | Pale yellow colored liquid | 6.09 | N/A | 100  100.2 | ND | ND | ND | ND | ND | ND | 0.06 |
| 6 Months: 25° C. | Clear, colorless liquid | 6.09 | N/A | 98.6  102.5 | ND | ND | ND | ND | ND | ND | ND |
| 6 Months: 40° C. | Clear, colorless liquid | 6.08 | N/A | 100.6  103.8 | ND | ND | ND | ND | ND | ND | 0.23 |

TABLE 29 (D)

| | | | | | Results | | | | | | |
|---|---|---|---|---|---|---|---|---|---|---|---|
| | | | | | APAP (%) | Related Substances (%)/RRT | | | | | |
| | | | | | | APAP | | | | | PGB |
| Interval | Appearance | pH | Osmolality (mOsm/Kg) | PGB (%) | 4-Amino-phenol 0.64 | Unk 0.75 | Unk 1.22 | Unk 1.38 | Unk 1.71 | Unk 1.94 | MPP 2.34 |
| 0 time | Clear, colorless liquid | 5.5 | 282 | 99.9  100.2 | ND | ND | ND | ND | ND | ND | ND |
| 1 Month: 25° C. | Clear, colorless liquid | 5.52 | N/A | 100.1  100.7 | ND | ND | ND | ND | ND | ND | ND |
| 1 Month: 40° C. | Clear, colorless liquid | 5.52 | N/A | 100.9  101.2 | ND | ND | ND | ND | ND | ND | ND |
| 2 Months: 25° C. | Clear, colorless liquid | 5.52 | N/A | 99.9  97.8 | ND | ND | ND | ND | ND | ND | ND |
| 2 Months: 40° C. | Clear, colorless liquid | 5.55 | N/A | 99.9  98.4 | ND | ND | ND | ND | ND | ND | ND |
| 3 Months: 25° C. | Clear, colorless liquid | 5.54 | N/A | 101.7  99.4 | ND | ND | ND | ND | ND | ND | ND |
| 3 Months: 40° C. | Clear, colorless liquid | 5.52 | N/A | 100.4  99.6 | ND | ND | ND | ND | ND | ND | 0.19 |
| 1 Month: 25° C. | Clear, colorless liquid | 6.02 | N/A | 101  99.9 | ND | ND | ND | ND | ND | ND | ND |
| 1 Month: 40° C. | Clear, colorless liquid | 6.02 | N/A | 101.3  101.3 | ND | ND | ND | ND | ND | ND | ND |

TABLE 29 (D)-continued

| | | | | | Results | | | | | | |
|---|---|---|---|---|---|---|---|---|---|---|---|
| | | | | | | APAP (%) | Related Substances (%)/RRT | | | | |
| | | | | | | | APAP | | | | | PGB |
| Interval | Appearance | pH | Osmolality (mOsm/Kg) | PGB (%) | | 4-Amino-phenol 0.64 | Unk 0.75 | Unk 1.22 | Unk 1.38 | Unk 1.71 | Unk 1.94 | MPP 2.34 |
| 2 Months: 25° C. | Clear, colorless liquid | 6.05 | N/A | 99.8 | 98.3 | ND | ND | ND | ND | ND | ND | ND |
| 2 Months: 40° C. | Clear, colorless liquid | 6.01 | N/A | 99.6 | 99.3 | ND | ND | ND | 0.13 | ND | ND | 0.17 |
| 3 Months: 25° C. | Clear, colorless liquid | 6.02 | N/A | 101.4 | 98.9 | ND | ND | ND | ND | ND | ND | ND |
| 3 Months: 40° C. | Clear, colorless liquid | 6.04 | N/A | 99.9 | 99.3 | ND | ND | ND | ND | ND | ND | 0.09 |

TABLE 30 (E)

| | | | | | Results | | | | | | |
|---|---|---|---|---|---|---|---|---|---|---|---|
| | | | | | | APAP (%) | Related Substances (%)/RRT | | | | |
| | | | | | | | APAP | | | | | PGB |
| Interval | Appearance | pH | Osmolality (mOsm/Kg) | PGB (%) | | 4-Amino-phenol 0.64 | Unk 0.75 | Unk 1.22 | Unk 1.38 | Unk 1.71 | Unk 1.94 | MPP 2.34 |
| 0 time | Clear, colorless liquid | 6 | 268 | 100.6 | 99.8 | ND | ND | ND | ND | ND | ND | ND |
| 1 Month: 25° C. | Clear, colorless liquid | 6.02 | N/A | 101 | 99.9 | ND | ND | ND | ND | ND | ND | ND |
| 1 Month: 40° C. | Clear, colorless liquid | 6.02 | N/A | 101.3 | 101.3 | ND | ND | ND | ND | ND | ND | ND |
| 2 Months: 25° C. | Clear, colorless liquid | 6.05 | N/A | 99.8 | 98.3 | ND | ND | ND | ND | ND | ND | ND |
| 2 Months: 40° C. | Clear, colorless liquid | 6.01 | N/A | 99.6 | 99.3 | ND | ND | ND | 0.13 | ND | ND | 0.17 |
| 3 Months: 25° C. | Clear, colorless liquid | 6.02 | N/A | 101.4 | 98.9 | ND | ND | ND | ND | ND | ND | ND |
| 3 Months: 40° C. | Clear, colorless liquid | 6.04 | N/A | 99.9 | 99.3 | ND | ND | ND | ND | ND | ND | 0.09 |

TABLE 31 (F)

| | | | | | Results | | | | | | |
|---|---|---|---|---|---|---|---|---|---|---|---|
| | | | | | | APAP (%) | Related Substances (%)/RRT | | | | |
| | | | | | | | APAP | | | | | PGB |
| Interval | Appearance | pH | Osmolality (mOsm/Kg) | PGB (%) | | 4-Amino-phenol 0.64 | Unk 0.75 | Unk 1.22 | Unk 1.38 | Unk 1.71 | Unk 1.94 | MPP 2.34 |
| 0 time | Clear, colorless liquid | 5.52 | 273 | 101 | 100.4 | ND | ND | ND | ND | ND | ND | ND |
| 1 Month: 25° C. | Clear, colorless liquid | 5.52 | N/A | 101.1 | 100.5 | ND | ND | ND | ND | ND | ND | ND |

TABLE 31 (F)-continued

Results

| | | | | | APAP (%) | Related Substances (%)/RRT | | | | | |
| | | | | | | APAP | | | | | PGB |
| Interval | Appearance | pH | Osmolality (mOsm/Kg) | PGB (%) | | 4-Amino-phenol 0.64 | Unk 0.75 | Unk 1.22 | Unk 1.38 | Unk 1.71 | Unk 1.94 | MPP 2.34 |
|---|---|---|---|---|---|---|---|---|---|---|---|---|
| 1 Month: 40° C. | Clear, colorless liquid | 5.51 | N/A | 100.8 | 102.3 | ND | ND | ND | ND | ND | ND | ND |
| 2 Months: 25° C. | Clear, colorless liquid | 5.5 | N/A | 98.9 | 98.6 | ND | ND | ND | ND | ND | ND | ND |
| 2 Months: 40° C. | Clear, colorless liquid | 5.5 | N/A | 99.8 | 98.7 | ND | ND | ND | 0.13 | ND | ND | 0.19 |
| 3 Months: 25° C. | Clear, colorless liquid | 5.54 | N/A | 100.4 | 99.1 | ND | ND | ND | ND | ND | ND | ND |
| 3 Months: 40° C. | Clear, colorless liquid | 5.54 | N/A | 98.9 | 99.5 | ND | ND | ND | ND | ND | ND | 0.15 |

TABLE 32 (B)

Results

| | | | | | APAP (%) | Related Substances (%)/RRT | | | | | |
| | | | | | | APAP | | | | | PGB |
| Interval | Appearance | pH | Osmolality (mOsm/Kg) | PGB (%) | | 4-Amino-phenol 0.64 | Unk 0.75 | Unk 1.22 | Unk 1.38 | Unk 1.71 | Unk 1.94 | MPP 2.34 |
|---|---|---|---|---|---|---|---|---|---|---|---|---|
| 0 time | Clear, colorless liquid | 6.02 | 292 | 99 | 99.7 | ND | ND | 0.05 | ND | ND | ND | ND |
| 1 Month: 25° C. | Clear, colorless liquid | 6.03 | N/A | 100 | 101.2 | ND | ND | ND | ND | ND | ND | ND |
| 1 Month: 40° C. | Clear, colorless liquid | 6.03 | N/A | 101.9 | 101.3 | ND | ND | ND | ND | ND | ND | ND |
| 2 Months: 25° C. | Clear, colorless liquid | 6.05 | N/A | 98.2 | 98.8 | ND | ND | ND | ND | ND | ND | ND |
| 2 Months: 40° C. | Clear, colorless liquid | 6.04 | N/A | 98.4 | 97 | ND | ND | ND | ND | ND | ND | ND |
| 3 Months: 25° C. | Clear, colorless liquid | 6.04 | N/A | 101.2 | 98.2 | ND | ND | ND | ND | ND | ND | ND |
| 3 Months: 40° C. | Clear, colorless liquid | 6.04 | N/A | 101.4 | 100 | ND | ND | 0.05 | ND | ND | ND | 0.08 |

The results above indicate that all of the formulations remained as clear, colorless liquids after 3 or 6 months at the accelerated degradation condition of 40° C. The results also indicated that the tested samples demonstrated minimal fluctuation in pH over the experimental time periods, nor was there a significant increase in impurities over the experimental time period.

EMBODIMENTS

The following non-limiting embodiments provide illustrative examples of the invention, but do not limit the scope of the invention.

Embodiment 1. A pharmaceutical composition comprising, in a liquid unit dosage form: a) a gabapentinoid; b) acetaminophen; c) a pH-adjusting agent; and d) water.

Embodiment 2. The pharmaceutical composition of embodiment 1, wherein the gabapentinoid is gabapentin, or a pharmaceutically acceptable salt thereof.

Embodiment 3. The pharmaceutical composition of embodiment 1, wherein the gabapentinoid is pregabalin, or a pharmaceutically acceptable salt thereof.

Embodiment 4. The pharmaceutical composition of any one of embodiments 1-3, wherein the liquid unit dosage form further comprises an acid, a conjugate base of the acid, or both the acid and the conjugate base of the acid.

Embodiment 5. The pharmaceutical composition of embodiment 4, wherein the acid is citric acid.

Embodiment 6. The pharmaceutical composition of embodiment 4, wherein the acid is acetic acid.

Embodiment 7. The pharmaceutical composition of embodiment 4, wherein the acid is phosphoric acid.

Embodiment 8. The pharmaceutical composition of any one of embodiments 1-7, wherein the liquid unit dosage form further comprises an isotonicity inducing agent.

Embodiment 9. The pharmaceutical composition of embodiment 8, wherein the isotonicity inducing agent is sodium chloride.

Embodiment 10. The pharmaceutical composition of embodiment 8, wherein the isotonicity inducing agent is mannitol.

Embodiment 11. The pharmaceutical composition of any one of embodiments 1-10, wherein the pH-adjusting agent is sodium hydroxide.

Embodiment 12. The pharmaceutical composition of any one of embodiments 1-10, wherein the pH-adjusting agent is hydrochloric acid.

Embodiment 13. The pharmaceutical composition of any one of embodiments 1-12, wherein the gabapentinoid is present in the liquid unit dosage form in an amount from about 0.1 mg/mL to about 50 mg/mL.

Embodiment 14. The pharmaceutical composition of any one of embodiments 1-13, wherein the acetaminophen is present in the liquid unit dosage form in an amount from about 2 mg/mL to about 20 mg/mL.

Embodiment 15. The pharmaceutical composition of any one of embodiments 1-14, wherein the liquid unit dosage form further comprises a decomposition product of the gabapentinoid at a level of no more than about 5%.

Embodiment 16. The pharmaceutical composition of embodiment 15, wherein the decomposition product of the gabapentinoid is 4-(2-methylpropyl)pyrrolidin-2-one.

Embodiment 17. The pharmaceutical composition of any one of embodiments 1-16, wherein the liquid unit dosage form further comprises a decomposition product of the acetaminophen at a level of no more than about 0.5%.

Embodiment 18. The pharmaceutical composition of embodiment 17, wherein the decomposition product of the acetaminophen is 4-aminophenol.

Embodiment 19. The pharmaceutical composition of any one of embodiments 1-18, wherein the liquid unit dosage form has a pH of about 4 to about 7.

Embodiment 20. The pharmaceutical composition of embodiment 19, wherein the pH of the liquid unit dosage form is about 5.

Embodiment 21. The pharmaceutical composition of embodiment 19, wherein the pH of the liquid unit dosage form is about 5.5

Embodiment 22. The pharmaceutical composition of embodiment 19, wherein the pH of the liquid unit dosage form is about 6.

Embodiment 23. The pharmaceutical composition of embodiment 1, wherein the liquid unit dosage form further comprises: e) an acid, a conjugate base of the acid, or both the acid and the conjugate base of the acid; f) sodium chloride; g) a decomposition product of the gabapentinoid; and h) a decomposition product of the acetaminophen.

Embodiment 24. The pharmaceutical composition of embodiment 1, wherein the liquid unit dosage form comprises: a) the gabapentinoid, wherein the gabapentinoid is pregabalin, or a pharmaceutically acceptable salt thereof, wherein the pregabalin is present in the liquid unit dosage form in an amount of about 0.1 to about 20 mg/mL; b) the acetaminophen, wherein the acetaminophen is present in the liquid unit dosage form in an amount of about 10 mg/mL; c) the pH-adjusting agent, wherein the pH-adjusting agent is sodium hydroxide; d) about 1.87 mg/mL sodium dihydrogen phosphate; e) about 5.5 mg/mL sodium chloride; and f) water, wherein the liquid unit dosage form has a pH of about 5 to about 7.

Embodiment 25. The pharmaceutical composition of embodiment 24, wherein the pH of the liquid unit dosage form is about 6.

Embodiment 26. The pharmaceutical composition of embodiment 1, wherein the liquid unit dosage form comprises: a) the gabapentinoid, wherein the gabapentinoid is pregabalin, or a pharmaceutically acceptable salt thereof, wherein the pregabalin is present in the liquid unit dosage form in an amount of about 0.1 to about 20 mg/mL; b) the acetaminophen, wherein the acetaminophen is present in the liquid unit dosage form in an amount of about 10 mg/mL; c) the pH-adjusting agent, wherein the pH-adjusting agent is sodium hydroxide; d) about 2.101 mg/mL citric acid monohydrate; e) about 2.25 mg/mL sodium chloride; and f) water, wherein the liquid unit dosage form has a pH of about 5 to about 7.

Embodiment 27. The pharmaceutical composition of embodiment 26, wherein the pH of the liquid unit dosage is about 6.

Embodiment 28. The pharmaceutical composition of embodiment 1, wherein the liquid unit dosage form comprises: a) the gabapentinoid, wherein the gabapentinoid is pregabalin, or a pharmaceutically acceptable salt thereof, wherein the pregabalin is present in the liquid unit dosage form in an amount of about 0.1 to about 20 mg/mL; b) the acetaminophen, wherein the acetaminophen is present in the liquid unit dosage form in an amount of about 10 mg/mL; c) the pH-adjusting agent, wherein the pH-adjusting agent is sodium hydroxide; d) about 1.55 mg/mL L-Histidine; e) about 2.25 mg/mL sodium chloride; and f) water, wherein the liquid unit dosage form has a pH of about 5 to about 7.

Embodiment 29. The pharmaceutical composition of embodiment 28, wherein the pH of the liquid unit dosage form is about 6.

Embodiment 30. The pharmaceutical composition of embodiment 1, wherein the liquid unit dosage form comprises: a) the gabapentinoid, wherein the gabapentinoid is pregabalin, or a pharmaceutically acceptable salt thereof, wherein the pregabalin is present in the liquid unit dosage form in an amount of about 0.1 to about 20 mg/mL; b) the acetaminophen, wherein the acetaminophen is present in the liquid unit dosage form in an amount of about 10 mg/mL; c) the pH-adjusting agent, wherein the pH-adjusting agent is sodium hydroxide; d) about 2.101 mg/mL citric acid monohydrate; e) about 5 mg/mL sodium chloride; and f) water, wherein the liquid unit dosage form has a pH of about 5 to about 7.

Embodiment 31. The pharmaceutical composition of embodiment 30, wherein the pH of the liquid unit dosage form is about 5.5.

Embodiment 32. The pharmaceutical composition of embodiment 1, wherein the liquid unit dosage form comprises: a) the gabapentinoid, wherein the gabapentinoid is pregabalin, or a pharmaceutically acceptable salt thereof, wherein the pregabalin is present in the liquid unit dosage form in an amount of about 0.1 to about 20 mg/mL; b) the acetaminophen, wherein the acetaminophen is present in the liquid unit dosage form in an amount of about 10 mg/mL; c) the pH-adjusting agent, wherein the pH-adjusting agent is sodium hydroxide; d) about 0.6 mg/mL acetic acid; e) about 5 mg/mL sodium chloride; and f) water, wherein the liquid unit dosage form has a pH of about 5 to about 7.

Embodiment 33. The pharmaceutical composition of embodiment 32, wherein the pH of the liquid unit dosage form is about 5.5.

Embodiment 34. The pharmaceutical composition of embodiment 1, wherein the liquid unit dosage form comprises: a) the gabapentinoid, wherein the gabapentinoid is pregabalin, or a pharmaceutically acceptable salt thereof, wherein the pregabalin is present in the liquid unit dosage form in an amount of about 0.1 to about 20 mg/mL; b) the acetaminophen, wherein the acetaminophen is present in the liquid unit dosage form in an amount of about 10 mg/mL; c) the pH-adjusting agent, wherein the pH-adjusting agent is sodium hydroxide; d) about 1.2 mg/mL sodium dihydrogen phosphate; e) about 5.5 mg/mL sodium chloride; and f) water, wherein the liquid unit dosage form has a pH of about 5 to about 7.

Embodiment 35. The pharmaceutical composition of embodiment 34, wherein the pH of the liquid unit dosage form is about 6.

Embodiment 36. The pharmaceutical composition of embodiment 1, wherein the liquid unit dosage form further comprises an impurity, wherein the impurity is determined based on: (a) injecting the liquid unit dosage form into a high performance liquid chromatography apparatus, wherein the apparatus comprises: (i) a chromatography column containing adsorbent particles as a stationary phase; (ii) a first mobile phase passing through the chromatography column, wherein the first mobile phase is aqueous potassium dihydrogen phosphate at pH 7 with 2% acetonitrile; and (iii) a second mobile phase passing through the chromatography column, wherein the second mobile phase is aqueous potassium dihydrogen phosphate at pH 7 with 60% acetonitrile; (b) running the liquid unit dosage form through the chromatography column for 34 minutes; (c) eluting the impurity from the chromatography column using a gradient of the first mobile phase, and a gradient of the second mobile phase, wherein each of the first mobile phase and second mobile phase are run at a flow rate of 1.5 mL/min through the chromatography column; (d) passing the impurity through a UV detector to generate a UV spectrum of the eluted unit dosage form and the impurity; (e) identifying the impurity based on a retention time of the impurity relative to a standard; and (f) calculating an amount of the impurity based on an integration of a peak obtained for the impurity from the UV spectrum.

Embodiment 37. The pharmaceutical composition of any one of embodiments 1-35, wherein the pharmaceutical composition is formulated for packaging in a bag, a glass vial, or a prefilled syringe.

Embodiment 38. The pharmaceutical composition of embodiment 37, wherein the pharmaceutical composition is formulated for packaging in a bag, wherein the bag is a polymer bag.

Embodiment 39. The pharmaceutical composition of embodiment 38, wherein the polymer bag is a polypropylene bag, and the polypropylene bag is further packaged in an aluminum over-pouch.

Embodiment 40. The pharmaceutical composition of embodiment 39, wherein the aluminum over-pouch contains an oxygen scavenger.

Embodiment 41. A method of treating pain in a subject in need thereof, the method comprising administering to the subject a therapeutically-effective amount of a liquid unit dosage form, wherein the liquid unit dosage form comprises: a) a gabapentinoid; b) acetaminophen; c) a pH-adjusting agent; and d) water.

Embodiment 42. The method of embodiment 41, wherein the gabapentinoid is gabapentin, or a pharmaceutically acceptable salt thereof.

Embodiment 43. The method of embodiment 41, wherein the gabapentinoid is pregabalin, or a pharmaceutically acceptable salt thereof.

Embodiment 44. The method of any one of embodiments 41-43, wherein the liquid unit dosage form further comprises an acid, a conjugate base of the acid, or both the acid and the conjugate base of the acid.

Embodiment 45. The method of embodiment 44, wherein the acid is citric acid.

Embodiment 46. The method of embodiment 44, wherein the acid is acetic acid.

Embodiment 47. The method of embodiment 44, wherein the acid is phosphoric acid.

Embodiment 48. The method of any one of embodiments 41-47, wherein the liquid unit dosage form further comprises an isotonicity inducing agent.

Embodiment 49. The method of embodiment 48, wherein the isotonicity inducing agent is sodium chloride.

Embodiment 50. The method of embodiment 48, wherein the isotonicity inducing agent is mannitol.

Embodiment 51. The method of any one of embodiments 41-50, wherein the pH-adjusting agent is sodium hydroxide.

Embodiment 52. The method of any one of embodiments 41-50, wherein the pH-adjusting agent is hydrochloric acid.

Embodiment 53. The method of any one of embodiments 41-52, wherein the gabapentinoid is present in the liquid unit dosage form in an amount from about 0.1 mg/mL to about 50 mg/mL.

Embodiment 54. The method of any one of embodiments 41-52, wherein the acetaminophen in present in the liquid unit dosage form in an amount from about 2 mg/mL to about 20 mg/mL.

Embodiment 55. The method of any one of embodiments 41-54, wherein the liquid unit dosage form further comprises a decomposition product of the gabapentinoid at a level of no more than about 5%.

Embodiment 56. The method of embodiment 55, wherein the decomposition product of the gabapentinoid is 4-(2-methylpropyl)pyrrolidin-2-one.

Embodiment 57. The method of any one embodiments 41-56, wherein the liquid unit dosage form further comprises a decomposition product of the acetaminophen at a level of no more than 0.5%.

Embodiment 58. The method of embodiment 57, wherein the decomposition product of the acetaminophen is 4-aminophenol.

Embodiment 59. The method of any one of embodiments 41-58, wherein the liquid unit dosage form has a pH of about 4 to about 7.

Embodiment 60. The method of embodiment 59, wherein the pH of the liquid unit dosage form is about 5.

Embodiment 61. The method of embodiment 59, wherein the pH of the liquid unit dosage form is about 5.5.

Embodiment 62. The method of embodiment 59, wherein the pH of the liquid unit dosage form is about 6.

Embodiment 63. The method of any one of embodiments 41-62, wherein the pain is postoperative pain.

Embodiment 64. The method of any one of embodiments 41-63, wherein the liquid unit dosage form is administered to the subject within 24 hours prior to the subject undergoing a surgical procedure.

Embodiment 65. The method of any one of embodiments 41-63, wherein the liquid unit dosage form is administered to the subject simultaneously with the subject undergoing a surgical procedure.

Embodiment 66. The method of any one of embodiments 41-63, wherein the liquid unit dosage form is administered to the subject within 24 hours after the subject has undergone a surgical procedure.

Embodiment 67. The method of any one of embodiments 41-66, wherein the administration is intravenous administration.

Embodiment 68. The method of any one of embodiments 41-66, wherein the administration is intramuscular administration.

Embodiment 69. The method of any one of embodiments 41-66, wherein the administration is subcutaneous administration.

Embodiment 70. A method of manufacturing a pharmaceutical formulation, the method comprising: a) adding water to a manufacturing tank; b) deoxygenating the water in the manufacturing tank by sparging nitrogen to achieve a dissolved oxygen level of less than about 1 ppm; c) adding a buffer to the water in the manufacturing tank to provide a mixture; d) adding a pH-adjusting agent to the mixture in the manufacturing tank, wherein the adding the pH-adjusting agent to the mixture in the manufacturing tank adjusts a pH of the mixture to about pH 4 to about pH 7; e) disposing a gabapentinoid into the mixture in the manufacturing tank; and f) disposing acetaminophen into the mixture in the manufacturing tank.

Embodiment 71. The method of embodiment 70, further comprising removing a portion of the mixture from the manufacturing tank and packaging the portion of the mixture that was removed from the manufacturing tank in a container.

Embodiment 72. The method of embodiment 71, wherein the container is a polymer bag.

Embodiment 73. The method of embodiment 71, wherein the container is a glass vial or a prefilled syringe.

Embodiment 74. The method of embodiment 72, wherein the polymer bag is a polypropylene bag, and the polypropylene bag is further packaged in an aluminum over-pouch.

Embodiment 75. The method of embodiment 74, wherein the aluminum over-pouch contains an oxygen scavenger.

Embodiment 76. The method of any one of embodiments 70-75, wherein the gabapentinoid is gabapentin, or a pharmaceutically acceptable salt thereof.

Embodiment 77. The method of any one of embodiments 70-75, wherein the gabapentinoid is pregabalin, or a pharmaceutically acceptable salt thereof.

Embodiment 78. The method of any one of embodiments 70-77, wherein the pH-adjusting agent is sodium hydroxide.

Embodiment 79. The method of any one of embodiments 70-77, wherein the pH-adjusting agent is hydrochloric acid.

Embodiment 80. The method of embodiment 72, 74, or 75, wherein the gabapentinoid is present in the polymer bag in an amount from about 0.1 mg/mL to about 50 mg/mL.

Embodiment 81. The method of embodiment 73, wherein the gabapentinoid is present in the glass vial in an amount from about 0.1 mg/mL to about 50 mg/mL.

Embodiment 82. The method of embodiment 72, 74, or 75, wherein the acetaminophen in present in the polymer bag in an amount from about 2 mg/mL to about 20 mg/mL.

Embodiment 83. The method of embodiment 73, wherein the acetaminophen in present in the glass vial in an amount from about 2 mg/mL to about 20 mg/mL.

Embodiment 100. A pharmaceutical composition, comprising in a liquid unit dosage form: a) a gabapentinoid, or a pharmaceutically acceptable salt thereof; b) acetaminophen; c) a pH-adjusting agent; and d) water, wherein the liquid unit dosage form has a pH of about 4.5, and wherein upon storage of the liquid unit dosage form at about 60° C. for at least about two weeks, the liquid unit dosage form exhibits less than about 2% degradation.

Embodiment 101. A pharmaceutical composition, comprising in a liquid unit dosage form: a) a gabapentinoid, or a pharmaceutically acceptable salt thereof; b) acetaminophen; c) a pH-adjusting agent; and d) water, wherein the liquid unit dosage form has a pH of about 4.5, and wherein upon storage of the liquid unit dosage form at about 40° C. for at least about one month, the liquid unit dosage form exhibits less than about 2% degradation.

Embodiment 102. A pharmaceutical composition, comprising in a liquid unit dosage form: a) a gabapentinoid, or a pharmaceutically acceptable salt thereof; b) acetaminophen; c) a pH-adjusting agent; and d) water, wherein the liquid unit dosage form has a pH of about 4.5, and wherein upon storage of the liquid unit dosage form at about 25° C. for at least about one month, the liquid unit dosage form exhibits less than about 2% degradation.

Embodiment 103. A pharmaceutical composition, comprising in a liquid unit dosage form: a) a gabapentinoid, or a pharmaceutically acceptable salt thereof; b) acetaminophen; c) a pH-adjusting agent; and d) water, wherein the liquid unit dosage form has a pH of about 5 to about 6, and wherein upon storage of the liquid unit dosage form at about 60° C. for at least about two weeks, the liquid unit dosage form comprises no more than about 5% of 4-(2-methylpropyl)pyrrolidin-2-one.

Embodiment 104. A pharmaceutical composition, comprising in a liquid unit dosage form: a) a gabapentinoid, or a pharmaceutically acceptable salt thereof; b) acetaminophen; c) a pH-adjusting agent; and d) water, wherein the liquid unit dosage form has a pH of about 6, and wherein upon storage of the liquid unit dosage form at about 60° C. for at least about two weeks, the liquid unit dosage form comprises no more than about 1% of 4-aminophenol.

Embodiment 105. A pharmaceutical composition, comprising in a liquid unit dosage form: a) a gabapentinoid, or a pharmaceutically acceptable salt thereof; b) acetaminophen; c) a pH-adjusting agent; and d) water, wherein the liquid unit dosage form has a pH of about 5 to about 6, and wherein upon storage of the liquid unit dosage form at about 60° C. for at least about two weeks, the liquid unit dosage form comprises no more than about 0.5% of 4-aminophenol.

Embodiment 106. A pharmaceutical composition, comprising in a liquid unit dosage form: a) a gabapentinoid, or a pharmaceutically acceptable salt thereof; b) acetaminophen; c) a pH-adjusting agent; and d) water, wherein the liquid unit dosage form has a pH of about 6, and wherein upon storage of the liquid unit dosage form at about 60° C. for at least about two weeks, the liquid unit dosage form comprises no more than about 2% of 4-(2-methylpropyl)pyrrolidin-2-one.

Embodiment 107. A pharmaceutical composition, comprising in a liquid unit dosage form: a) a gabapentinoid, or a pharmaceutically acceptable salt thereof; b) acetaminophen; c) a pH-adjusting agent; and d) water, wherein the liquid unit dosage form has a pH of about 6, and wherein upon storage of the liquid unit dosage form at about 40° C. for at least about six months, the liquid unit dosage form comprises no more than about 0.5% of 4-(2-methylpropyl)pyrrolidin-2-one.

Embodiment 108. A pharmaceutical composition, comprising in a liquid unit dosage form: a) a gabapentinoid, or a pharmaceutically acceptable salt thereof; b) acetaminophen; c) citric acid monohydrate; and d) water, wherein the liquid unit dosage form has a pH of about 6, and wherein upon storage of the liquid unit dosage form at about 60° C. for at least about two weeks, the liquid unit dosage form comprises no more than about 7% of 4-(2-methylpropyl) pyrrolidin-2-one.

Embodiment 109. A pharmaceutical composition, comprising in a liquid unit dosage form: a) a gabapentinoid, or a pharmaceutically acceptable salt thereof; b) acetaminophen; c) L-Histidine; and d) water, wherein the liquid unit dosage form has a pH of about 6, and wherein upon storage of the liquid unit dosage form at about 60° C. for at least about two weeks, the liquid unit dosage form comprises no more than about 3% of 4-(2-methylpropyl)pyrrolidin-2-one.

Embodiment 110. A pharmaceutical composition, comprising in a liquid unit dosage form: a) a gabapentinoid, or a pharmaceutically acceptable salt thereof; b) acetaminophen; c) a pH-adjusting agent; and d) water, wherein the liquid unit dosage form has a pH of about 5.5, and wherein upon storage of the liquid unit dosage form at about 60° C. for at least about two weeks, the liquid unit dosage form comprises no more than about 0.5% of 4-aminophenol.

Embodiment 111. A pharmaceutical composition, comprising in a liquid unit dosage form: a) a gabapentinoid, or a pharmaceutically acceptable salt thereof; b) acetaminophen; c) a pH-adjusting agent; and d) water, wherein the liquid unit dosage form has a pH of about 5.5, and wherein upon storage of the liquid unit dosage form at about 60° C. for at least about two weeks, the liquid unit dosage form comprises no more than about 4% of 4-(2-methylpropyl) pyrrolidin-2-one.

Embodiment 112. A pharmaceutical composition, comprising in a liquid unit dosage form: a) a gabapentinoid, or a pharmaceutically acceptable salt thereof; b) acetaminophen; c) a pH-adjusting agent; and d) water, wherein the liquid unit dosage form has a pH of about 5.5, and wherein upon storage of the liquid unit dosage form at about 40° C. for at least about six months, the liquid unit dosage form comprises no more than about 0.5% of 4-(2-methylpropyl) pyrrolidin-2-one.

Embodiment 113. A pharmaceutical composition, comprising in a liquid unit dosage form: a) a gabapentinoid, or a pharmaceutically acceptable salt thereof; b) acetaminophen; c) acetic acid; and d) water, wherein the liquid unit dosage form has a pH of about 5.5, and wherein upon storage of the liquid unit dosage form at about 60° C. for at least about two weeks, the liquid unit dosage form comprises no more than about 2% of 4-(2-methylpropyl)pyrrolidin-2-one.

What is claimed is:

1. A pharmaceutical composition comprising, in a liquid unit dosage form:
   a) a gabapentinoid, wherein the gabapentinoid is pregabalin, or a pharmaceutically acceptable salt thereof;
   b) acetaminophen;
   c) a pH-adjusting agent; and
   d) water;
   wherein the liquid unit dosage form has a pH of between 5 and 7;
   wherein the gabapentinoid is present in the liquid unit dosage form in an amount from about 0.1 mg/mL to about 50 mg/mL; and
   wherein the acetaminophen is present in the liquid unit dosage form in an amount from about 2 mg/mL to about 20 mg/mL.

2. The pharmaceutical composition of claim 1, wherein the gabapentinoid is the pharmaceutically acceptable salt of pregabalin.

3. The pharmaceutical composition of claim 1, wherein the liquid unit dosage form further comprises an acid, a conjugate base of the acid, or both the acid and the conjugate base of the acid.

4. The pharmaceutical composition of claim 3, wherein the acid is citric acid.

5. The pharmaceutical composition of claim 3, wherein the acid is acetic acid.

6. The pharmaceutical composition of claim 3, wherein the acid is phosphoric acid.

7. The pharmaceutical composition of claim 1, wherein the liquid unit dosage form further comprises an isotonicity inducing agent.

8. The pharmaceutical composition of claim 7, wherein the isotonicity inducing agent is sodium chloride.

9. The pharmaceutical composition of claim 7, wherein the isotonicity inducing agent is mannitol.

10. The pharmaceutical composition of claim 1, wherein the pH-adjusting agent is sodium hydroxide.

11. The pharmaceutical composition of claim 1, wherein the pH-adjusting agent is hydrochloric acid.

12. The pharmaceutical composition of claim 1, wherein the liquid unit dosage form further comprises a decomposition product of the gabapentinoid at a level of no more than about 5%.

13. The pharmaceutical composition of claim 12, wherein the decomposition product of the gabapentinoid is 4-(2-methylpropyl)pyrrolidin-2-one.

14. The pharmaceutical composition of claim 1, wherein the liquid unit dosage form further comprises a decomposition product of the acetaminophen at a level of no more than about 0.5%.

15. The pharmaceutical composition of claim 14, wherein the decomposition product of the acetaminophen is 4-aminophenol.

16. The pharmaceutical composition of claim 1, wherein the pH of the liquid unit dosage form is 5.

17. The pharmaceutical composition of claim 1, wherein the pH of the liquid unit dosage form is about 5.5.

18. The pharmaceutical composition of claim 1, wherein the pH of the liquid unit dosage form is about 6.

19. The pharmaceutical composition of claim 1, wherein the liquid unit dosage form further comprises:
   e) an acid, a conjugate base of the acid, or both the acid and the conjugate base of the acid;
   f) sodium chloride;
   g) a decomposition product of the gabapentinoid; and
   h) a decomposition product of the acetaminophen.

20. The pharmaceutical composition of claim 1, wherein the liquid unit dosage form comprises:
   a) the gabapentinoid, wherein the gabapentinoid is pregabalin, or a pharmaceutically acceptable salt thereof, wherein the pregabalin is present in the liquid unit dosage form in an amount of about 0.1 to about 20 mg/mL;
   b) the acetaminophen, wherein the acetaminophen is present in the liquid unit dosage form in an amount of about 10 mg/mL;
   c) the pH-adjusting agent, wherein the pH-adjusting agent is sodium hydroxide;
   d) about 1.87 mg/mL sodium dihydrogen phosphate;

e) about 5.5 mg/mL sodium chloride; and
f) water.

21. The pharmaceutical composition of claim 20, wherein the pH of the liquid unit dosage form is about 6.

22. The pharmaceutical composition of claim 1, wherein the liquid unit dosage form comprises:
   a) the gabapentinoid, wherein the gabapentinoid is pregabalin, or a pharmaceutically acceptable salt thereof, wherein the pregabalin is present in the liquid unit dosage form in an amount of about 0.1 to about 20 mg/mL;
   b) the acetaminophen, wherein the acetaminophen is present in the liquid unit dosage form in an amount of about 10 mg/mL;
   c) the pH-adjusting agent, wherein the pH-adjusting agent is sodium hydroxide;
   d) equal or less than 0.5 mg/mL citric acid monohydrate;
   e) equal or less than 6.0 mg/mL sodium chloride; and
   f) water.

23. The pharmaceutical composition of claim 22, wherein the pH of the liquid unit dosage is about 6.

24. The pharmaceutical composition of claim 1, wherein the liquid unit dosage form comprises:
   a) the gabapentinoid, wherein the gabapentinoid is pregabalin, or a pharmaceutically acceptable salt thereof, wherein the pregabalin is present in the liquid unit dosage form in an amount of about 0.1 to about 20 mg/mL;
   b) the acetaminophen, wherein the acetaminophen is present in the liquid unit dosage form in an amount of about 10 mg/mL;
   c) the pH-adjusting agent, wherein the pH-adjusting agent is sodium hydroxide;
   d) about 1.55 mg/mL L-Histidine;
   e) about 2.25 mg/mL sodium chloride; and
   f) water.

25. The pharmaceutical composition of claim 24, wherein the pH of the liquid unit dosage form is about 6.

26. The pharmaceutical composition of claim 1, wherein the liquid unit dosage form comprises:
   a) the gabapentinoid, wherein the gabapentinoid is pregabalin, or a pharmaceutically acceptable salt thereof, wherein the pregabalin is present in the liquid unit dosage form in an amount of about 0.1 to about 20 mg/mL;
   b) the acetaminophen, wherein the acetaminophen is present in the liquid unit dosage form in an amount of about 10 mg/mL;
   c) the pH-adjusting agent, wherein the pH-adjusting agent is sodium hydroxide;
   d) between 0.2 mg/mL and 0.6 mg/mL citric acid monohydrate;
   e) between 1.5 mg/mL and about 6 mg/mL sodium chloride; and
   f) water.

27. The pharmaceutical composition of claim 26, wherein the pH of the liquid unit dosage form is about 5.5.

28. The pharmaceutical composition of claim 1, wherein the liquid unit dosage form comprises:
   a) the gabapentinoid, wherein the gabapentinoid is pregabalin, or a pharmaceutically acceptable salt thereof, wherein the pregabalin is present in the liquid unit dosage form in an amount of about 0.1 to about 20 mg/mL;
   b) the acetaminophen, wherein the acetaminophen is present in the liquid unit dosage form in an amount of about 10 mg/mL;
   c) the pH-adjusting agent, wherein the pH-adjusting agent is sodium hydroxide;
   d) about 0.6 mg/mL acetic acid;
   e) about 5 mg/mL sodium chloride; and
   f) water.

29. The pharmaceutical composition of claim 28, wherein the pH of the liquid unit dosage form is about 5.5.

30. The pharmaceutical composition of claim 1, wherein the liquid unit dosage form comprises:
   a) the gabapentinoid, wherein the gabapentinoid is pregabalin, or a pharmaceutically acceptable salt thereof, wherein the pregabalin is present in the liquid unit dosage form in an amount of about 0.1 to about 20 mg/mL;
   b) the acetaminophen, wherein the acetaminophen is present in the liquid unit dosage form in an amount of about 10 mg/mL;
   c) the pH-adjusting agent, wherein the pH-adjusting agent is sodium hydroxide;
   d) about 1.2 mg/mL sodium dihydrogen phosphate;
   e) about 5.5 mg/mL sodium chloride; and
   f) water.

31. The pharmaceutical composition of claim 30, wherein the pH of the liquid unit dosage form is about 6.

32. The pharmaceutical composition of claim 1, wherein the liquid unit dosage form further comprises an impurity, wherein the impurity is determined based on:
   (a) injecting the liquid unit dosage form into a high performance liquid chromatography apparatus, wherein the apparatus comprises:
      (i) a chromatography column containing adsorbent particles as a stationary phase;
      (ii) a first mobile phase passing through the chromatography column, wherein the first mobile phase is aqueous potassium dihydrogen phosphate at pH 7 with 2% acetonitrile; and
      (iii) a second mobile phase passing through the chromatography column, wherein the second mobile phase is aqueous potassium dihydrogen phosphate at pH 7 with 60% acetonitrile;
   (b) running the liquid unit dosage form through the chromatography column for 34 minutes;
   (c) eluting the impurity from the chromatography column using a gradient of the first mobile phase, and a gradient of the second mobile phase, wherein each of the first mobile phase and second mobile phase are run at a flow rate of 1.5 mL/min through the chromatography column;
   (d) passing the impurity through a UV detector to generate a UV spectrum of the eluted unit dosage form and the impurity;
   (e) identifying the impurity based on a retention time of the impurity relative to a standard; and
   (f) calculating an amount of the impurity based on an integration of a peak obtained for the impurity from the UV spectrum.

33. The pharmaceutical composition of claim 1, wherein the pharmaceutical composition is formulated for packaging in a bag, a glass vial, or a prefilled syringe.

34. The pharmaceutical composition of claim 33, wherein the pharmaceutical composition is formulated for packaging in a bag, wherein the bag is a polymer bag.

35. The pharmaceutical composition of claim 34, wherein the polymer bag is a polypropylene bag, and the polypropylene bag is further packaged in an aluminum over-pouch.

36. The pharmaceutical composition of claim 35, wherein the aluminum over-pouch contains an oxygen scavenger.

\* \* \* \* \*